(12) United States Patent
Travassos

(10) Patent No.: US 9,896,512 B2
(45) Date of Patent: Feb. 20, 2018

(54) ANTITUMOR PEPTIDE DERIVED FROM A COMPLEMENTARITY DETERMINING REGION OF A HUMANIZED MONOCLONAL ANTIBODY TO NAP12B TRANSPORTER

(71) Applicant: Recepta Biopharma S.A., Sao Paulo (BR)

(72) Inventor: Luiz Rodolpho Raja Gabaglia Travassos, Sao Paulo (BR)

(73) Assignee: Recepta Biopharma S.A. (BR)

( * ) Notice: Subject to any disclaimer, the term of this patent is extended or adjusted under 35 U.S.C. 154(b) by 80 days.

(21) Appl. No.: 14/924,003

(22) Filed: Oct. 27, 2015

(65) Prior Publication Data

US 2016/0108132 A1  Apr. 21, 2016

Related U.S. Application Data

(62) Division of application No. 13/991,688, filed as application No. PCT/IB2011/003053 on Dec. 14, 2011, now Pat. No. 9,193,797.

(60) Provisional application No. 61/422,856, filed on Dec. 14, 2010.

(51) Int. Cl.
*C07K 16/30* (2006.01)
*A61K 36/10* (2006.01)
*C07K 9/00* (2006.01)
*A61K 39/00* (2006.01)

(52) U.S. Cl.
CPC .......... *C07K 16/3069* (2013.01); *A61K 36/10* (2013.01); *C07K 16/30* (2013.01); *C07K 16/3061* (2013.01); *A61K 2039/505* (2013.01); *C07K 9/00* (2013.01); *C07K 2317/24* (2013.01); *C07K 2317/565* (2013.01); *C07K 2317/73* (2013.01); *C07K 2317/734* (2013.01)

(58) Field of Classification Search
None
See application file for complete search history.

(56) References Cited

U.S. PATENT DOCUMENTS 5,827,498 A   10/1998   Seki et al.
6,174,691 B1   1/2001   Courtenay-Luck
6,689,753 B1   2/2004   Soto-Jara

FOREIGN PATENT DOCUMENTS

WO   2005040219 A1   5/2005
WO   2009097128 A1   8/2009

OTHER PUBLICATIONS

Adessi et al., "Converting a Peptide into a Drug: Strategies to Improve Stability and Bioavailability", Current Medical Chemistry, 9, pp. 963-978, 2002.
Arap et al., "Cancer Treatment by Targeted Drug Delivery to Tumor Vasculature in a Mouse Model", Science 279, pp. 377-380, 1998.
Chemotherapy Service, ed., M.C. Perry, Williams & Wilkins, Baltimore, MD (1992), TOC, Index, p. 2 only.
Dobroff et al., "Differential Antitumor Effects of IgG and IgM Monoclonal Antibodies and Their Sythetic Complementarity-Determining Regions Directed to New Targets of B16F10-Nex2 Melanoma Cells" Translational Oncology, vol. 3, No. 4, pp. 204-217, Aug. 2010.
Dobroff et al., "Protective, Anti-Tumor Monoclonal Antibody Recognizes a Conformational Epitope Similar to Melibiose a the Surface of Invasive Murine Melanoma Cells", Hybridoma and Hybridomics, vol. 21, No. 5, pp. 321-331, 2002.
Elgqvist et al., "Therapeutic Efficacy and Tumor Dose Estimations in Radioimmunotherapy of Intraperitoneally Growing OVCAR-3 Cells in Nude Mice with 211 At-Labeled Monoclonal Antibody MX35", The Journal of Nuclear Medicine, vol. 46, No. 11, pp. 1907-1915, Nov. 2005.
Finstad et al., "Distribution of Radiolabeled Monoclonal Antibody MX35 F(ab')2 in Tissue Samples by Storage Phosphor Screen Image Analysis: Evaluation of Antibody Localization to Micrometastatic Disease in Epithelial Ovarian Cancer", Clinical Cancer Research, vol. 3 (8), pp. 1433-1442, Aug. 1997.
Freireich et al., "Quantitative Comparison of Toxicity of Anticancer Agents in Mouse, Rat, Hamster, Dog, Monkey, and Man", Cancer Chemotherapy Reports, 1966, vol. 50, pp. 219-244.
Goldenberg, "Introduction to the Eleventh Conference on Cancer Therapy with Antibodies and Immunoconjugates", Clin Cancer Res 2008: 13 (18 Suppl.), 5499-5500, Sep. 15, 2007.
Hultborn et al., "Patent Audrey Conference 2006", Cancer Biother Radiopharm 21: 373-381, 2006.
Hultborn et al., Pharmacokinetics and Dosimetry of 211At-MX35 F(ab)2 in Therapy of Ovarian Cancer—Preliminary Results from an Ongoing Phase I Study, 395 (Oral Presentation 39) 2006, 17 pages.
Kabat et al., "Sequences of proteins of immunological interest", 5th edition, Public Health Service, N.I.H., Washington, DC., 1991, available at <http://www.kilibro.com/book/preview/107832_sequences-of-proteins-of-immunological-interest-5th-ed-6-vols>, TOC ony—3 pages.
Litman et al., "Reconstructiong Immune Phylogeny: New Perspectives", Nature Reviews Immunol, vol. 5, pp. 866-879, Nov. 2005.
Magliani et al., "Antibodies as Crypts of Antiinfective and Antitumor Peptides", Current Medicinal Chemistry, vol. 16, No. 8, pp. 2305-2323, 2009.
Mattes et al., "Mouse Monoclonal Antibodies to Human Epithelial Differentiation Antigens Expressed on the Surface of Ovarian Carcinoma Ascites Cells", Cancer Research, 47, pp. 6741-6750, Dec. 15, 1987.
McFarland et al., "Imaging Tumors with an Albumin-Binding Fab, a Novel Tumor-Targeting Agent" Cancer Res. 67(1): pp. 254-261, Jan. 1, 2007.
Mordenti, J. and Chappell, W. "The use of interspecies scaling in toxicokinetics" in Toxicokinetics and New Drug Development, Yacobi et al., eds., Pergamon Press, New York 1989, pp. 42-96.
Morea et al. "Conformations of the Third Hypervariable Region in the VH Domain of Immunoglobulins", J. Mol. Biol., 275: pp. 269-294, 1998.

(Continued)

*Primary Examiner* — Amber D Steele
(74) *Attorney, Agent, or Firm* — Lerner, David, Littenberg, Krumholz & Mentilik, LLP

(57) ABSTRACT

Described herein is novel isolated or synthetic peptides derived from a complementarity determining region hypervariable domain amino acid sequence of a humanized monoclonal antibody to NaPi2B transporter, as well as derivatives thereof, and a pharmaceutical composition and a method for inhibiting tumor growth or treating a tumor or cancer treating using the antitumor peptides and derivatives thereof.

5 Claims, 41 Drawing Sheets

(56) References Cited

OTHER PUBLICATIONS

Pasqualini and Ruoslahti, "Integrins as receptors for tumor targeting by circulating ligands" Nature Biotechnology, vol. 15 pp. 542-546, Jun. 1997.
Pasqualini and Ruoslahti, "Organ targeting in vivo using phage display peptide libraries" Letters toNature, vol. 380, pp. 364-366, Mar. 28, 1996.
Polonelli et al., "Antibody Complementarity-Determining Regions (CDRs) Can Display Differential Antimicrobial, Antiviral and Antitumor Activities", PLoS One, vol. 3, Issue 6, e2371, pp. 1-9, Jun. 2008.
Scientific Tables, Geigy Pharmaceuticals, Ardley, New York, 1970, pp. 537, Body Surface Area of Adults.
The Molecular Basis of Cancer, Mendelsohn and Israel, eds., Chapter 1, entitled "Cell cycle regulation, oncogens, and antineoplastic drugs" by Murakami et al., (WB Saunders: Philadelphia, 1995), Chapter 1—15 pages only.

RB9/MELANOMA B16F10-Nex2.1

RB10/MELANOMA B16F10 Nex2.1

RB9- GLIOBLASTOMA U87MG

RB10- GLIOBLASTOMA U87MG

RB9- BREAST CANCER SKBR3

RB10- BREAST CANCER SKBR3

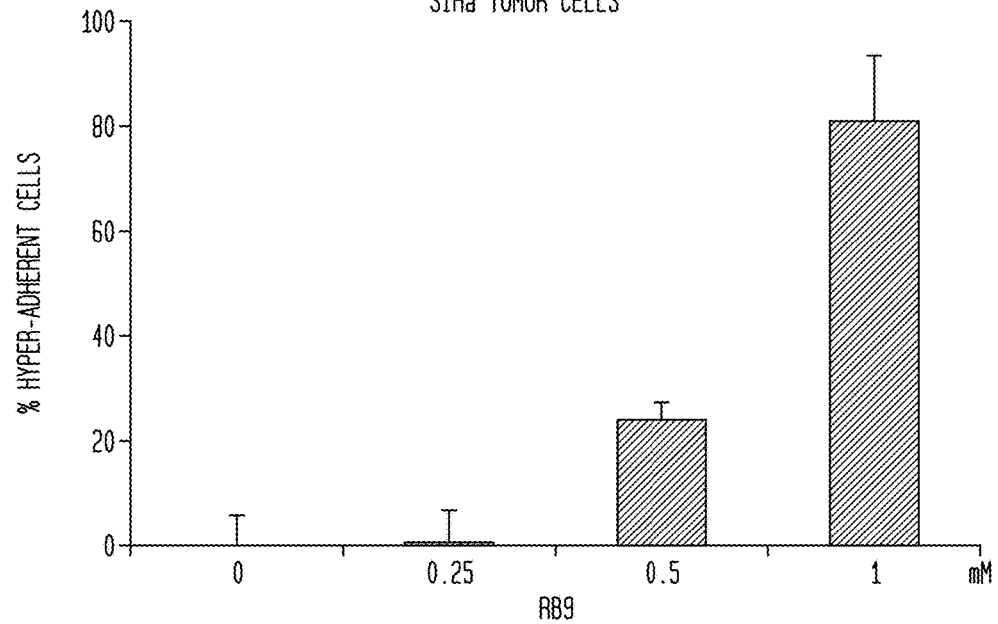
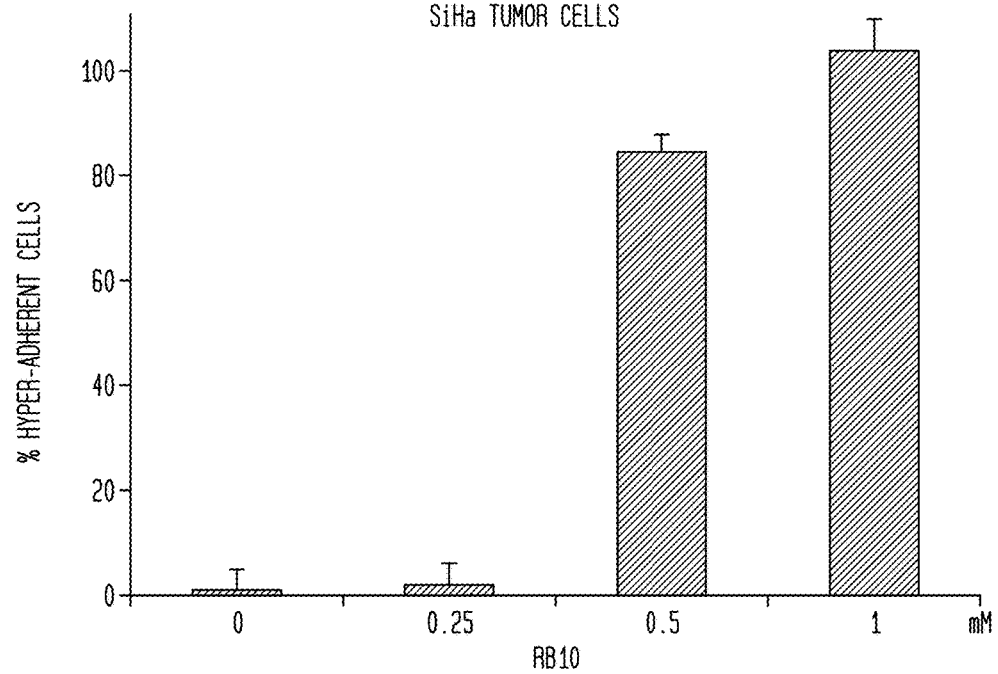

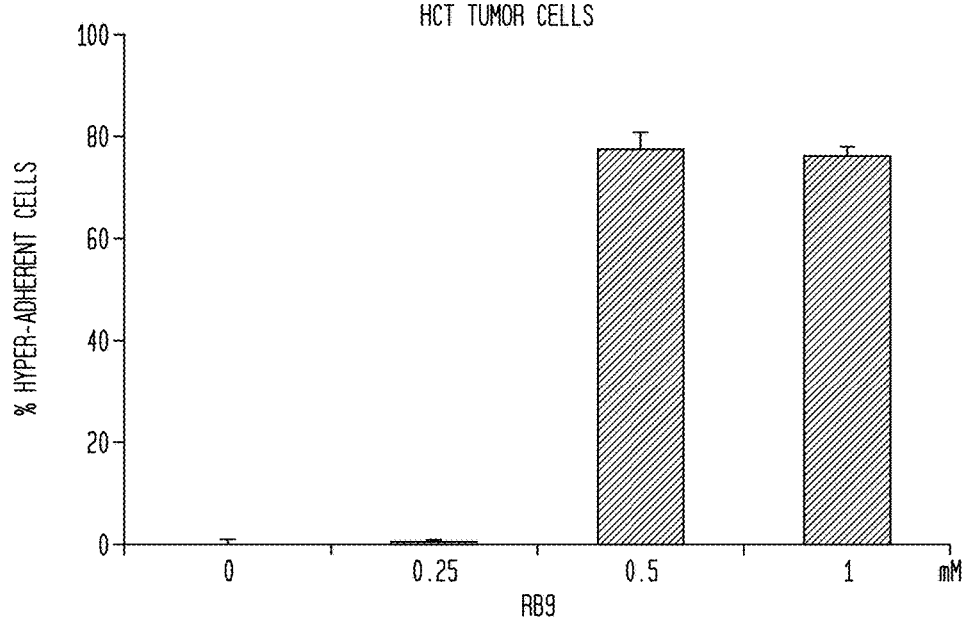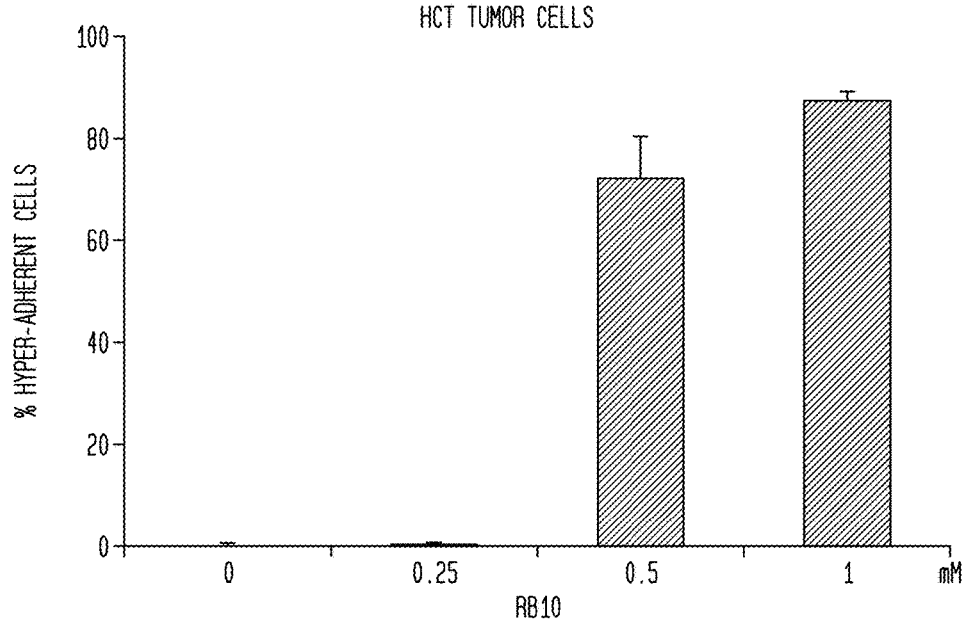

MELANOMA NODULES IN SUCCESSFULLY TREATED MICE

HL-60 LEUKEMIA RB9
CELL NUMBER $y = -5E-05x^2 - 0.0062x + 99.698$
$R^2 = 0.9925$

EC50 ~ 930 μM

HL-60 LEUKEMIA RB9
MTT $y = -2E-05x^2 - 0.0377x + 100.04$
$R^2 = 0.9999$

EC50 ~ 920 μM

OVCAR-3 RB9
CELL NUMBER $y = -5E-05x^2 + 0.0225x + 97.95$
$R^2 = 0.9234$

OVCAR-3 RB9
MTT

CONTROL

H2O2

RB10

PLASMA DEGRADATION OF PEPTIDE RB9

MIGRATION OF 5 × 10⁵ B16F10-Nex2 MELANOMA CELLS IN CONTROL

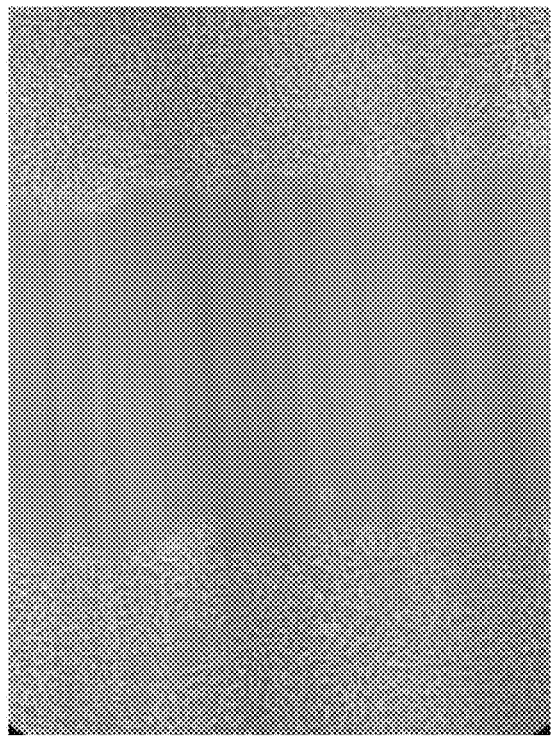
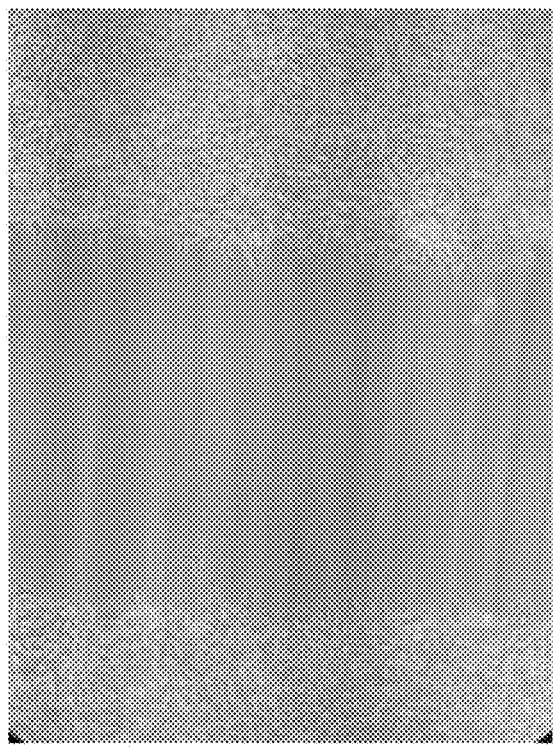
FIG. 13B
100% MIGRATION INHIBITION OF $10^6$ B16F10-Nex2 MELANOMA CELLS BY RB10 500 μM RB10 DOSE-DEPENDENT MIGRATION INHIBITION
MURINE MELANOMA B16F10-Nex2

RB10  500 μM  12 h INCUBATION
GROWTH INHIBITION (39%) OF B16F10-Nex2 MELANOMA CELLS

B16F10-Nex2 MIGRATION

B16F10-Nex2 MIGRATION

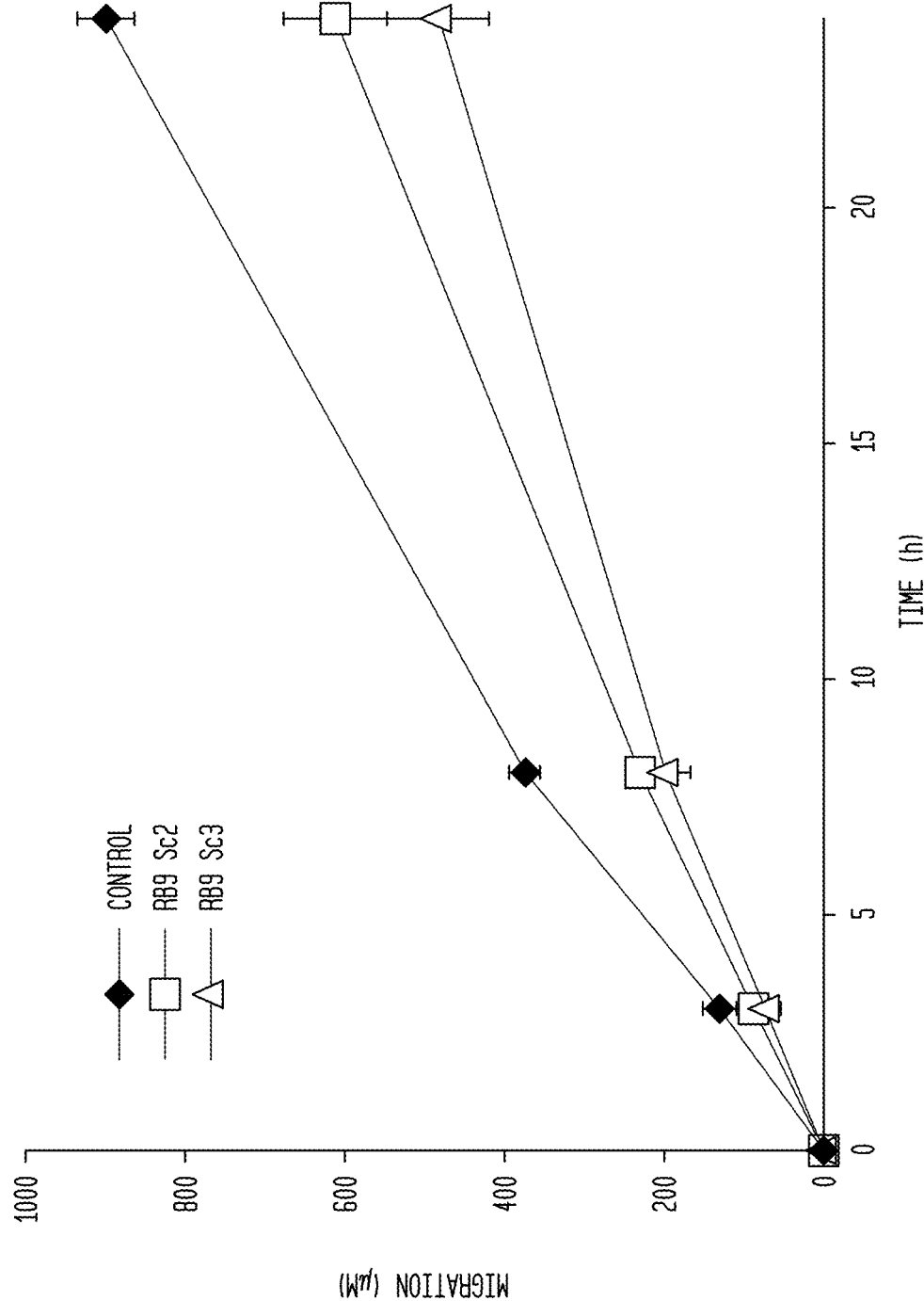

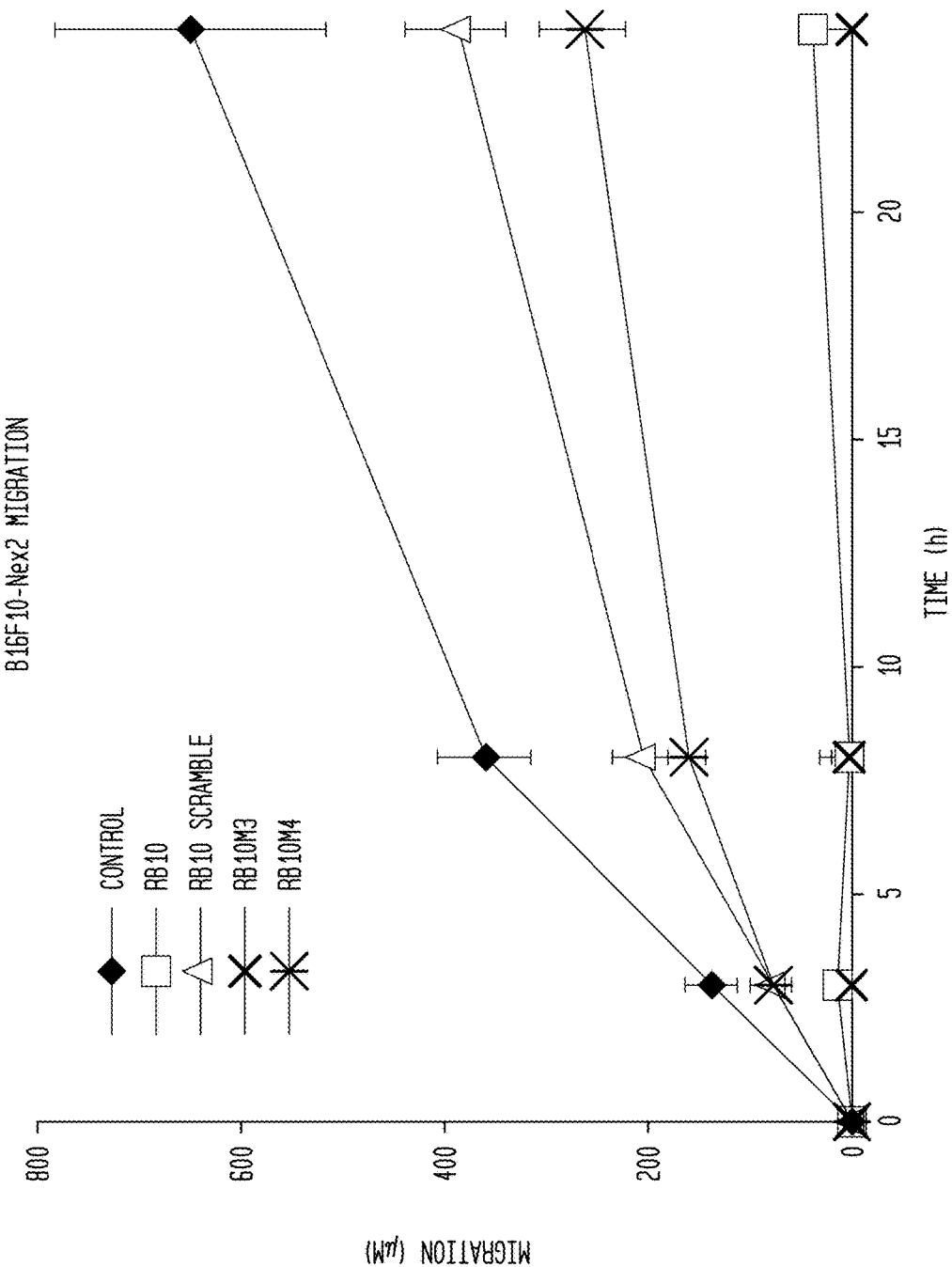

B16F10-Nex2 MIGRATION -RB10 A1 (C1A)

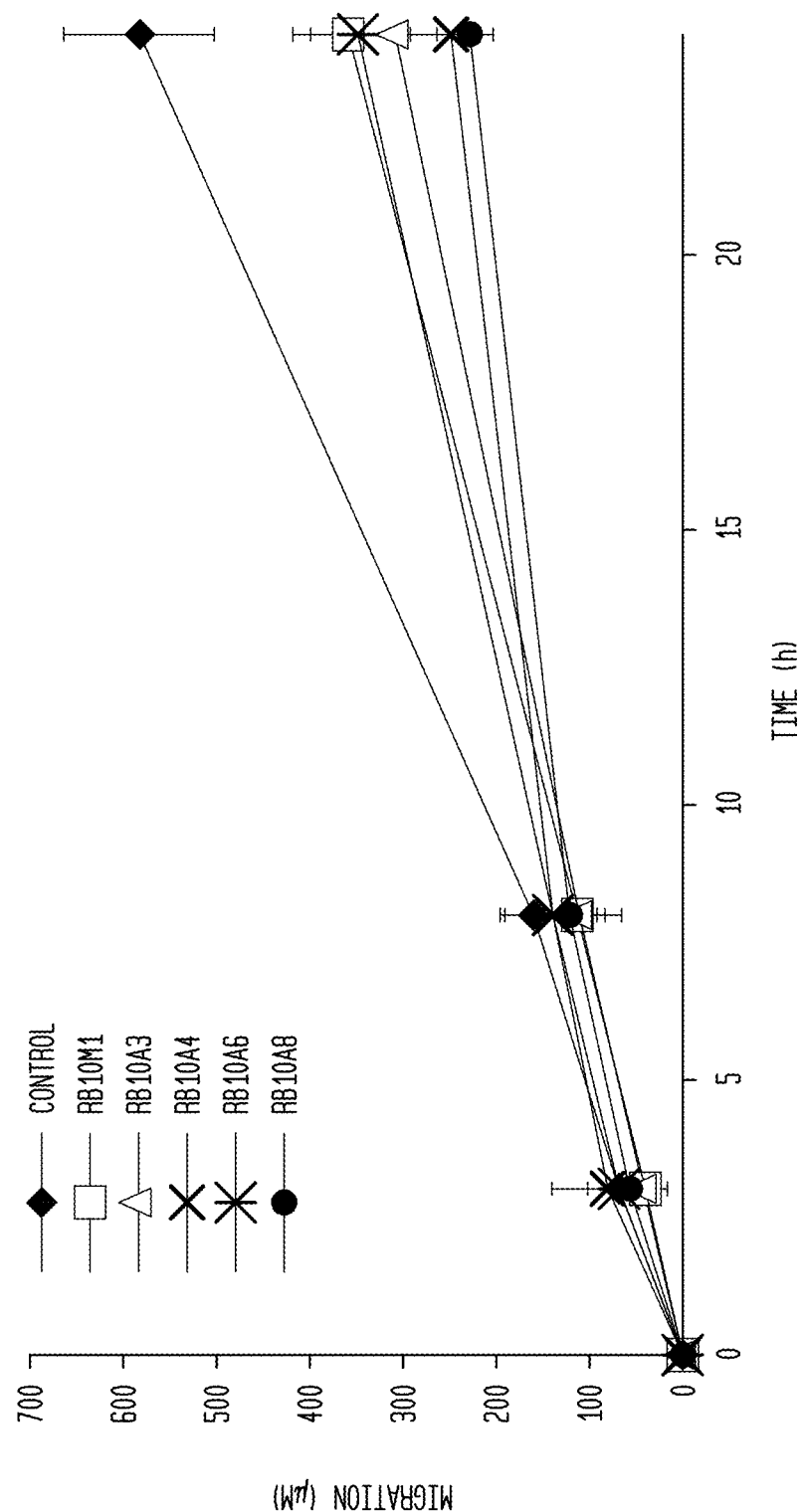

A2058 MELANOMA CELLS

U87 CELL MIGRATION

HCT MIGRATION

SiHa CELL MIGRATION

OVCAR-3 CELL MIGRATION

SKBR-3 CELL MIGRATION

U87 CELL MIGRATION

U87 CELL MIGRATION

SiHa CELL MIGRATION

HeLa CELL MIGRATION

FIBROBLASTS 3T3 MIGRATION

FIBROBLASTS RP MIGRATION

FIBROBLASTS T75 MIGRATION

RB9 INHIBITS B16F10-Nex2 INVASION (TRANSWELL ASSAY)

HEMOLYSIS

SEQUENCE LISTING

<160> NUMBER OF SEQ ID NOS: 36

<210> SEQ ID NO 1
<211> LENGTH: 10
<212> TYPE: PRT

```
<213> ORGANISM: Artificial Sequence
<220> FEATURE:
<223> OTHER INFORMATION: Sequence of CDR H1 from RebMab 200 (huMX35),
      obtainable by a known method

<400> SEQUENCE: 1

Gly Tyr Thr Phe Thr Gly Tyr Asn Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Sequence of CDR H2 from RebMab 200 (huMX35),
      obtainable by a known method

<400> SEQUENCE: 2

Ala Ile Tyr Pro Gly Asn Gly Asn Thr Ser Tyr Lys Gln Lys Phe Arg
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Sequence of CDR H3 from RebMab 200 (huMX35),
      obtainable by a known method

<400> SEQUENCE: 3

Cys Ala Arg Gly Glu Thr Ala Arg Ala Thr Phe Ala Tyr Trp Gly Gln
1               5                   10                  15

Gly

<210> SEQ ID NO 4
<211> LENGTH: 11
<212> TYPE: PRT
<213> ORGANISM: Artificial Sequence
<220> FEATURE:
<223> OTHER INFORMATION: Sequence of CDR L1 from RebMab 200 (huMX35),
      obtainable by a known method

<400> SEQUENCE: 4

Ser Ala Ser Gln Asp Ile Gly Asn Phe Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Sequence of CDR L2 from RebMab 200 (huMX35),
      obtainable by a known method

<400> SEQUENCE: 5

Tyr Thr Ser Ser Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Sequence of CDR L3 from RebMab 200 (huMX35),
      obtainable by a known method
```

```
<400> SEQUENCE: 6

Gln Gln Tyr Ser Lys Leu Pro Leu Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Amidated sequence of CDR H2 from RebMab 200
      (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 7

Ala Ile Tyr Pro Gly Asn Gly Asn Thr Ser Tyr Lys Gln Lys Phe Arg
1               5                   10                  15

Gly

<210> SEQ ID NO 8
<211> LENGTH: 18
<212> TYPE: PRT
<213> ORGANISM: Artificial Sequence
<220> FEATURE:
<223> OTHER INFORMATION: Amidated and modified sequence of CDR H3 from
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide
<220> FEATURE:
<221> NAME/KEY: MISC_FEATURE
<222> LOCATION: (18)..(18)
<223> OTHER INFORMATION: Amidation

<400> SEQUENCE: 8

Cys Ala Arg Gly Glu Thr Ala Arg Ala Thr Phe Ala Tyr Trp Gly Gln
1               5                   10                  15

Gly Cys

<210> SEQ ID NO 9
<211> LENGTH: 17
<212> TYPE: PRT
<213> ORGANISM: Artificial Sequence
<220> FEATURE:
<223> OTHER INFORMATION: Amidated sequence of CDR H3 from RebMab 200
      (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 9

Cys Ala Arg Gly Glu Thr Ala Arg Ala Thr Phe Ala Tyr Trp Gly Gln
1               5                   10                  15

Gly

<210> SEQ ID NO 10
<211> LENGTH: 10
<212> TYPE: PRT
<213> ORGANISM: Artificial Sequence
<220> FEATURE:
<223> OTHER INFORMATION: Amidated sequence of CDR H1 from RebMab 200
      (huMX35), obtainable by a known method
<220> FEATURE:
<221> NAME/KEY: MISC_FEATURE
```

```
<222> LOCATION: (10)..(10)
<223> OTHER INFORMATION: Amidation

<400> SEQUENCE: 10

Gly Tyr Thr Phe Thr Gly Tyr Asn Ile His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Amidated sequence of CDR L1 of RebMab 200
      (huMX35), obtainable by a known method
<220> FEATURE:
<221> NAME/KEY: MISC_FEATURE
<222> LOCATION: (11)..(11)
<223> OTHER INFORMATION: Amidation

<400> SEQUENCE: 11

Ser Ala Ser Gln Asp Ile Gly Asn Phe Leu Asn
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Amidated sequence of CDR L2 of RebMab 200
      (huMX35), obtainable by a known method
<220> FEATURE:
<221> NAME/KEY: MISC_FEATURE
<222> LOCATION: (7)..(7)
<223> OTHER INFORMATION: Amidation

<400> SEQUENCE: 12

Tyr Thr Ser Ser Leu Tyr Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Amidated sequence of CDR L3 of RebMab 200
      (huMX35), obtainable by a known method
<220> FEATURE:
<221> NAME/KEY: MISC_FEATURE
<222> LOCATION: (9)..(9)
<223> OTHER INFORMATION: Amidation

<400> SEQUENCE: 13

Gln Gln Tyr Ser Lys Leu Pro Leu Thr
1               5

<210> SEQ ID NO 14
<211> LENGTH: 18
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide bond
<220> FEATURE:
<221> NAME/KEY: MODIFIED_BASE
<222> LOCATION: (2)..(17)
<223> OTHER INFORMATION: (2) and (17) are d-alanine and (8) is
      d-citrulline
```

```
<220> FEATURE:
<221> NAME/KEY: MISC_FEATURE
<222> LOCATION: (18)..(18)
<223> OTHER INFORMATION: Amidation

<400> SEQUENCE: 14

Cys Ala Arg Gly Glu Thr Ala Arg Ala Thr Phe Ala Tyr Trp Gly Gln
1               5                   10                  15

Ala Cys

<210> SEQ ID NO 15
<211> LENGTH: 18
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide bond
<220> FEATURE:
<221> NAME/KEY: MODIFIED_BASE
<222> LOCATION: (2)..(17)
<223> OTHER INFORMATION: (2) and (17) are d-alanine, (8) is
      d-citrulline, and (11) is d-phenylalanine
<220> FEATURE:
<221> NAME/KEY: MISC_FEATURE
<222> LOCATION: (18)..(18)
<223> OTHER INFORMATION: Amidation

<400> SEQUENCE: 15

Cys Ala Arg Gly Glu Thr Ala Arg Ala Thr Phe Ala Tyr Trp Gly Gln
1               5                   10                  15

Ala Cys

<210> SEQ ID NO 16
<211> LENGTH: 14
<212> TYPE: PRT
<213> ORGANISM: Artificial Sequence
<220> FEATURE:
<223> OTHER INFORMATION: Amidated and modified sequence derived from CDR
      H3 of RebMab 200 (huMX35), obtainable by a known method
<220> FEATURE:
<221> NAME/KEY: MISC_FEATURE
<222> LOCATION: (1)..(14)
<223> OTHER INFORMATION: Disulfide bond
<220> FEATURE:
<221> NAME/KEY: MODIFIED_BASE
<222> LOCATION: (2)..(2)
<223> OTHER INFORMATION: d-alanine
<220> FEATURE:
<221> NAME/KEY: MISC_FEATURE
<222> LOCATION: (18)..(18)
<223> OTHER INFORMATION: Amidation

<400> SEQUENCE: 16

Cys Ala Arg Gly Glu Thr Ala Arg Ala Thr Phe Ala Tyr Cys
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide bond
```

```
<220> FEATURE:
<221> NAME/KEY: MODIFIED_BASE
<222> LOCATION: (8)..(8)
<223> OTHER INFORMATION: d-citrulline
<220> FEATURE:
<221> NAME/KEY: MISC_FEATURE
<222> LOCATION: (18)..(18)
<223> OTHER INFORMATION: Amidation

<400> SEQUENCE: 17

Cys Ala Arg Gly Glu Thr Ala Arg Ala Thr Phe Ala Tyr Trp Gly Gln
1               5                   10                  15

Gly Cys

<210> SEQ ID NO 18
<211> LENGTH: 18
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide bond
<220> FEATURE:
<221> NAME/KEY: MODIFIED_BASE
<222> LOCATION: (2)..(2)
<223> OTHER INFORMATION: d-alanine
<220> FEATURE:
<221> NAME/KEY: MISC_FEATURE
<222> LOCATION: (18)..(18)
<223> OTHER INFORMATION: Amidation

<400> SEQUENCE: 18

Cys Ala Arg Gly Glu Thr Ala Arg Ala Thr Phe Ala Tyr Trp Gly Gln
1               5                   10                  15

Gly Cys

<210> SEQ ID NO 19
<211> LENGTH: 18
<212> TYPE: PRT
<213> ORGANISM: Artificial Sequence
<220> FEATURE:
<223> OTHER INFORMATION: Amidated and scrambled sequence of CDR H3 from
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide bond
<220> FEATURE:
<221> NAME/KEY: MISC_FEATURE
<222> LOCATION: (18)..(18)
<223> OTHER INFORMATION: Amidation

<400> SEQUENCE: 19

Cys Gly Thr Phe Glu Tyr Arg Ala Gln Ala Gly Trp Ala Gly Arg Thr
1               5                   10                  15

Ala Cys

<210> SEQ ID NO 20
<211> LENGTH: 18
<212> TYPE: PRT
<213> ORGANISM: Artificial Sequence
<220> FEATURE:
<223> OTHER INFORMATION: Amidated and scrambled sequence of CDR H3 from
      RebMab 200 (huMX35), obtainable by a known method
<220> FEATURE:
<221> NAME/KEY: MISC_FEATURE
<222> LOCATION: (3)..(15)
```

```
<223> OTHER INFORMATION: Disulfide bond
<220> FEATURE:
<221> NAME/KEY: MISC_FEATURE
<222> LOCATION: (18)..(18)
<223> OTHER INFORMATION: Amidation

<400> SEQUENCE: 20

Tyr Trp Cys Arg Ala Ala Phe Thr Thr Glu Ala Gly Arg Ala Cys Gln
1               5                   10                  15

Gly Gly

<210> SEQ ID NO 21
<211> LENGTH: 18
<212> TYPE: PRT
<213> ORGANISM: Artificial Sequence
<220> FEATURE:
<223> OTHER INFORMATION: Amidated and scrambled sequence of CDR H3 from
      RebMab 200 (huMX35), obtainable by a known method
<220> FEATURE:
<221> NAME/KEY: MISC_FEATURE
<222> LOCATION: (1)..(18)
<223> OTHER INFORMATION: Disulfide bond
<220> FEATURE:
<221> NAME/KEY: MISC_FEATURE
<222> LOCATION: (18)..(18)
<223> OTHER INFORMATION: Amidation

<400> SEQUENCE: 21

Cys Phe Thr Ala Arg Ala Gly Trp Tyr Ala Thr Glu Ala Arg Gly Gly
1               5                   10                  15

Gln Cys

<210> SEQ ID NO 22
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 22

Ala Ala Arg Gly Glu Thr Ala Arg Ala Thr Phe Ala Tyr Trp Gly Gln
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 23

Cys Ala Ala Gly Glu Thr Ala Arg Ala Thr Phe Ala Tyr Trp Gly Gln
1               5                   10                  15

Gly

<210> SEQ ID NO 24
```

```
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 24

Cys Ala Arg Ala Glu Thr Ala Arg Ala Thr Phe Ala Tyr Trp Gly Gln
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 25

Cys Ala Arg Gly Ala Thr Ala Arg Ala Thr Phe Ala Tyr Trp Gly Gln
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 26

Cys Ala Arg Gly Glu Ala Ala Arg Ala Thr Phe Ala Tyr Trp Gly Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 27

Cys Ala Arg Gly Glu Thr Ala Ala Ala Thr Phe Ala Tyr Trp Gly Gln
1               5                   10                  15

Gly
```

```
<210> SEQ ID NO 28
<211> LENGTH: 8
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MISC_FEATURE
<222> LOCATION: (8)..(8)
<223> OTHER INFORMATION: Amidation

<400> SEQUENCE: 28

Thr Phe Ala Tyr Trp Gly Gln Gly
1               5

<210> SEQ ID NO 29
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MODIFIED_BASE
<222> LOCATION: (8)..(17)
<223> OTHER INFORMATION: (8) is d-citrulline, (11) is d-phenylalanine
      and (17) is d-alanine
<220> FEATURE:
<221> NAME/KEY: MISC_FEATURE
<222> LOCATION: (17)..(17)
<223> OTHER INFORMATION: Amidation

<400> SEQUENCE: 29

Cys Ala Arg Gly Glu Thr Ala Arg Ala Thr Phe Ala Tyr Trp Gly Gln
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MODIFIED_BASE
<222> LOCATION: (3)..(17)
<223> OTHER INFORMATION: (3) and (8) are d-arginine, (11) is
      d-phenylalanine and (17) is d-alanine
<220> FEATURE:
<221> NAME/KEY: MISC_FEATURE
<222> LOCATION: (17)..(17)
<223> OTHER INFORMATION: Amidation

<400> SEQUENCE: 30

Cys Ala Arg Gly Glu Thr Ala Arg Ala Thr Phe Ala Tyr Trp Gly Gln
1               5                   10                  15

Ala

<210> SEQ ID NO 31
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MODIFIED_BASE
<222> LOCATION: (2)..(2)
<223> OTHER INFORMATION: d-alanine
```

```
<220> FEATURE:
<221> NAME/KEY: MISC_FEATURE
<222> LOCATION: (17)..(17)
<223> OTHER INFORMATION: Amidation

<400> SEQUENCE: 31

Cys Ala Arg Gly Glu Thr Ala Arg Ala Thr Phe Ala Tyr Trp Gly Gln
1               5                   10                  15
Gly

<210> SEQ ID NO 32
<211> LENGTH: 17
<212> TYPE: PRT
<213> ORGANISM: Artificial Sequence
<220> FEATURE:
<223> OTHER INFORMATION: Amidated and modified sequence of CDR H3 of
      RebMab 200 (huMX35), obtainable by a known method
<220> FEATURE:
<221> NAME/KEY: MODIFIED_BASE
<222> LOCATION: (2)..(17)
<223> OTHER INFORMATION: (2) is d-alanine, (8) is d-citrulline and (17)
      is d-alanine
<220> FEATURE:
<221> NAME/KEY: MISC_FEATURE
<222> LOCATION: (17)..(17)
<223> OTHER INFORMATION: Amidation

<400> SEQUENCE: 32

Cys Ala Arg Gly Glu Thr Ala Arg Ala Thr Phe Ala Tyr Trp Gly Gln
1               5                   10                  15
Ala

<210> SEQ ID NO 33
<211> LENGTH: 17
<212> TYPE: PRT
<213> ORGANISM: Artificial Sequence
<220> FEATURE:
<223> OTHER INFORMATION: Amidated and scrambled sequence of CDR H3 from
      RebMab 200 (huMX35), obtainable by a known method
<220> FEATURE:
<221> NAME/KEY: MISC_FEATURE
<222> LOCATION: (17)..(17)
<223> OTHER INFORMATION: Amidation

<400> SEQUENCE: 33

Cys Gly Thr Phe Glu Tyr Arg Ala Gln Ala Gly Trp Ala Gly Arg Thr
1               5                   10                  15
Ala

<210> SEQ ID NO 34
<211> LENGTH: 9
<212> TYPE: PRT
<213> ORGANISM: Artificial Sequence
<220> FEATURE:
<223> OTHER INFORMATION: Amidated and modified sequence of CDR H3 from
      RebMab 200 (huMX35), obtainable by a known method
<220> FEATURE:
<221> NAME/KEY: MISC_FEATURE
<222> LOCATION: (1)..(9)
<223> OTHER INFORMATION: peptide motif
<220> FEATURE:
<221> NAME/KEY: MISC_FEATURE
<222> LOCATION: (1)..(9)
<223> OTHER INFORMATION: peptide

<400> SEQUENCE: 34

Cys Asp Cys Arg Gly Asp Cys Phe Cys
1               5
```

```
<210> SEQ ID NO 35
<211> LENGTH: 20
<212> TYPE: PRT
<213> ORGANISM: Artificial Sequence
<220> FEATURE:
<223> OTHER INFORMATION: Amidated and modified sequence of CDR H3 from
      RebMab 200 (huMX35), obtainable by a known method
<220> FEATURE:
<221> NAME/KEY: MISC_FEATURE
<222> LOCATION: (1)..(20)
<223> OTHER INFORMATION: peptide

<400> SEQUENCE: 35

Gln Arg Leu Met Glu Asp Ile Glu Leu Pro Arg Trp Gly Glu Leu Trp
1               5                   10                  15

Glu Asp Asp Phe
            20

<210> SEQ ID NO 36
<211> LENGTH: 4
<212> TYPE: PRT
<213> ORGANISM: Artificial Sequence
<220> FEATURE:
<223> OTHER INFORMATION: Internal short peptide of Seq. 28

<400> SEQUENCE: 36

Thr Phe Ala Tyr
1
```

ANTITUMOR PEPTIDE DERIVED FROM A COMPLEMENTARITY DETERMINING REGION OF A HUMANIZED MONOCLONAL ANTIBODY TO NAP12B TRANSPORTER

CROSS-REFERENCE TO RELATED APPLICATION

The present application is a divisional of U.S. patent application Ser. No. 13/991,688, filed Jun. 5, 2013, now U.S. Pat. No. 9,193,797, which is a national phase entry under 35 U.S.C. § 371 of International Application No. PCT/IB2011/003053, filed Dec. 14, 2011, published in English, which claims the benefit of the filing date of U.S. Provisional Patent Application No. 61/422,856, filed on Dec. 14, 2010, all of which are incorporated herein by reference.

SEQUENCE LISTING

The instant application contains a Sequence Listing which has been submitted in ASCII format via EFS-Web and is hereby incorporated by reference in its entirety. Said ASCII copy, submitted Apr. 6, 2015, in U.S. application Ser. No. 13/991,688, and transferred to the present application, was created on Apr. 6, 2015, is named Revised Sequence Listing 4 6 15.TXT and is 15,554 bytes in size.

FIELD OF INVENTION

The present subject matter relates to biologically active peptides. In particular, the present subject matter provides novel antitumor peptides derived from a complementarity determining region of a humanized monoclonal antibody to NaPi2B transporter, and to pharmaceutical compositions and methods for inhibiting or treating a tumor or cancer. The present subject matter further concerns screening methods for identifying antitumor compounds, e.g., antitumor peptides.

BACKGROUND OF THE INVENTION

Worldwide, several carcinomas (cancers) stand out as leading killers, with millions of people dying from cancer every year.

This disease is characterized by the proliferation of abnormal or neoplastic cells derived from a normal tissue, forming a tumor mass, the invasion of adjacent tissues by these abnormal cells, and the generation of malignant cells which eventually spread via the blood or lymphatic system to regional lymph nodes and to distant sites (metastasis). With very few exceptions, metastatic disease from a carcinoma is fatal.

Due to the recurrence rates and side effects of current cancer treatment, there is a great need for new therapeutic agents capable of inhibiting neoplastic cell growth. In this scenario, immunoglobulin (Ig) molecules (both IgM and IgG) have been recently reported as sources of bioactive peptides that may display differential anti-microbial, anti-viral and anti-tumor activities in vitro and in vivo (Polonelli et al. PLoS One. 3(6):e2371, 2008; Magliani et al., Curr Med Chem. 6(18):2305-23, 2009). Such internal distribution of bioactive amino acid sequences parallels that of other peptide sequences expressed in receptors of native immunity (Litman et al., Nat. Rev. Immunol., 5: 866-879, 2005). There is, however, no structural similarity among them. Bioactive peptides with sizes ranging from 10aa to 20aa were obtained from the complementarity determining region (CDR) hypervariable domains, from sequences including framework and CDR amino acids, and even from Ig constant regions. To be tested, synthetic preparations of peptides were used which were generally amidated in the C-terminal amino acid. While bioactivity is generally independent of antibody specificity, CDR3 from $V_H$ may share antigen binding properties of the original antibody. This is especially true when the antigen is a peptide sequence and less so when it is a carbohydrate. Heavy chain CDR3 peptides that act as the original antibody are called "microantibodies (=microAbs)".

The conformation of $V_H$ CDR3 (H3) peptides was reviewed by Morea et al. (J. Mol. Biol., 275: 269-294, 1998). Unlike the canonical structures of the other five CDRs (H1, H2, L1, L2, L3), the H3 loops have various sizes flanked by $C^{92}$ and $G^{104}$ according to Kabat et al. (Sequences of proteins of immunological interest, 5th edition, Public Health Service, N.I.H., Washington, D.C., 1991) numbering in extended sequences of 10 to 22 amino acids.

An example of a bioactive $V_H$ CDR3 identified in a monoclonal antibody (mAb) is described hereinafter. Using anti-B16F10 melanoma mAb A4 (Dobroff et al., Hybrid. Hybridomics 21: 321-331, 2002), all six CDRs were tested in the form of synthetic peptides for cytotoxicity. Linear and cyclic extended H3 peptides bound to tumor cells, competed with mAb A4 for binding and they were cytotoxic in cells expressing protocadherin β-13, but not in HL-60 leukemia cells that do not express it (Dobroff et al., Translat. Onc., 3: 204-217, 2010). The advantage of using microAbs is in their small size making it easy to conduct the structure-function analysis and their accessibility to complex reaction sites.

Internal peptide sequences in immunoglobulins (e.g. monoclonal antibodies) belong to constant and variable regions. The CDRs, or the antigen recognizing sequences, although regarded as hypervariable domains, can be individually shared by different immunoglobulins or antibodies. Such similarity among antibodies can involve all CDRs (one each in a family of Ig molecules) with the exception of $V_H$ CDR 3. This CDR tends to be unique for a given antibody in its original $C^{92}$-$G^{104}$ sequence.

Mattes et al obtained, in 1987, a monoclonal murine IgG1 named MAb MX35, by immunizing mice with a mixture of four fresh ovarian carcinoma specimens. It showed reactivity with approximately 90% of human ovarian epithelial cancers and a limited number of normal tissues as determined by immunohistochemistry (Mattes et al., Cancer Res. 47: 6741-6750, 1987). MX35 MAb has been shown to also react with lung and renal carcinoma cell lines but not with most other carcinoma cell lines as well as cell lines derived from melanomas, astrocytomas, sarcomas, teratocarcinomas, choriocarcinomas and hematopoietic tumors. It reacted with 5/5 specimens of fresh ovarian carcinoma ascites cells by immunofluorescence, with 3/6 benign cysts and 18/18 solid tissue carcinomas by immunoperoxidase staining of frozen sections (Mattes et al., Cancer Res. 47: 6741-6750, 1987).

Subsequently, the localization and biodistribution of radiolabed murine antibody was studied in patients with ovarian carcinoma in phase I clinical trials. F(ab') of MAb MX35 has been shown to localize to micrometastatic ovarian carcinoma deposits in the peritoneal cavity (Finstad et al., Clin Cancer Res. 3(8):1433-1442, 1997). MAb MX35 and fragments thereof labeled with alpha-particle-emitting nuclide $^{211}$astatine (At-a) showed high efficacy in treating micrometastatic tumor growth in a nude mouse model of human ovarian cancer (Elgqvist et al., J Nucl Med. 46 (11): 1907-15, 2005). Also, the MX35 MAb has shown efficient selective tumor localization in vivo as indicated by PET imaging and histology. It also targeted tumors in patients with ovarian cancer with no severe adverse events reported (Hultbom et al., Cancer Biother Radiopharm 21: 373-381, 2006).

More recently, a humanized version of MX35 (called huMX35 or RebMab200) was obtained and is described in an international patent application filed on Jan. 29, 2009 (PCT/US2009/000576).

Throughout this specification, various scientific publications and patents or published patent applications are referenced. The disclosure of all these publications in their entireties is hereby incorporated by reference into this specification in order to more fully describe the state of the art to which the present subject matter pertains. Citation or identification of any reference in this section or any other part of this application shall not be construed as an admission that such reference is available as prior art herein.

SUMMARY OF THE INVENTION

It is an objective of the present subject matter to identify and provide peptides capable of inhibiting the growth of neoplastic cells, such as cancer cells. It has been found that peptides derived from RebMab200 humanized monoclonal antibody (huMX35) affect in vitro growth of several human tumor cell lines and also inhibit in vivo metastatic growth in a syngeneic model. It has been found that the peptides target cancer cells imprinting significant dose-dependent responses, ranging from hyper-adherence to inhibition of cell migration further translated into inhibition of cell invasion and metastasis.

Accordingly, one aspect of the present subject matter is to provide an isolated or synthetic antitumor peptide comprising an amino acid sequence derived from the complementarity determining region of a humanized monoclonal antibody RebMab200, as identified by SEQ ID NO: 3, or a derivative thereof. The derivative of SEQ ID NO: 3 can include an amino acid sequence selected from the group consisting of SEQ ID NOs: 8, 9 and 14-33. The present peptides show antitumor activity even against tumor cells that would not react with mAb MX35, such as melanoma and can be used as an active in a pharmaceutical composition or a method for inhibiting tumor growth or treating a tumor or cancer.

Accordingly, another aspect of the present subject matter is to provide a pharmaceutical composition comprising one or more of the antitumor peptides and a pharmaceutically acceptable carrier. Still another aspect of the present subject matter is to provide a method of inhibiting tumor growth or treating a cancer, comprising administering to a subject in need an effective amount of the antitumor peptides.

BRIEF DESCRIPTION OF THE DRAWINGS

FIG. 3A is a graphical representation of the effect of RB9 on cell adhesion in human SiHa cervical tumor cells.

FIG. 3B is a graphical representation of the effect of RB10 on cell adhesion in human SiHa cervical tumor cells.

FIG. 4A is a graphical representation of the effect of RB9 on cell adhesion in human HCT colon tumor cells.

FIG. 4B is a graphical representation of the effect of RB10 on cell adhesion in human HCT colon tumor cells.

FIG. 11A is a graphical representation of HPLC Mass Spectrometry of human plasma untreated.

FIG. 11B is a graphical representation of HPLC Mass Spectrometry of human plasma treated with RB9, at 0 hour.

FIG. 11C is a graphical representation of HPCL Mass Spectrometry of human plasma treated with RB9, at 24 hours.

FIG. 13B is a photographical representation of the migration of B16F10-Nex2 melanoma cells inhibited by the treatment with RB10 500 M, at 0 hour and 24 hours.

FIG. 16C is a graphical representation of the partial inhibition of B16F10-Nex2 cell migration by RB9 Sc2 and Rb9 Sc3.

FIG. 16D is a graphical representation of the complete inhibition of B16F10-Nex2 cell migration by RB10 and RB10 M3 and partial inhibition by RB10 Scramble and RB10 M4.

FIG. 16F is a graphical representation of the partial inhibition of B16F10-Nex2 cell migration by RB10 M1, RB10 A3, RB10 A4, RB10 A6 and RB10 A8.

DETAILED DESCRIPTION

Definitions

Figure 1A:
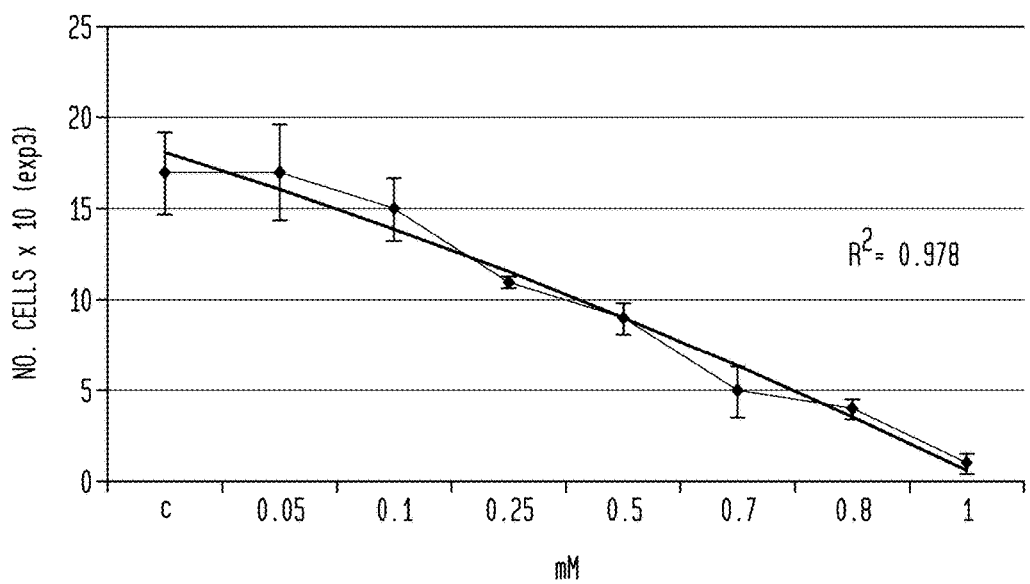
FIG. 1A is a graphical representation of the effect of RB9 on cell adhesion in murine B16F10-Nex2.1.
Figure 1B:
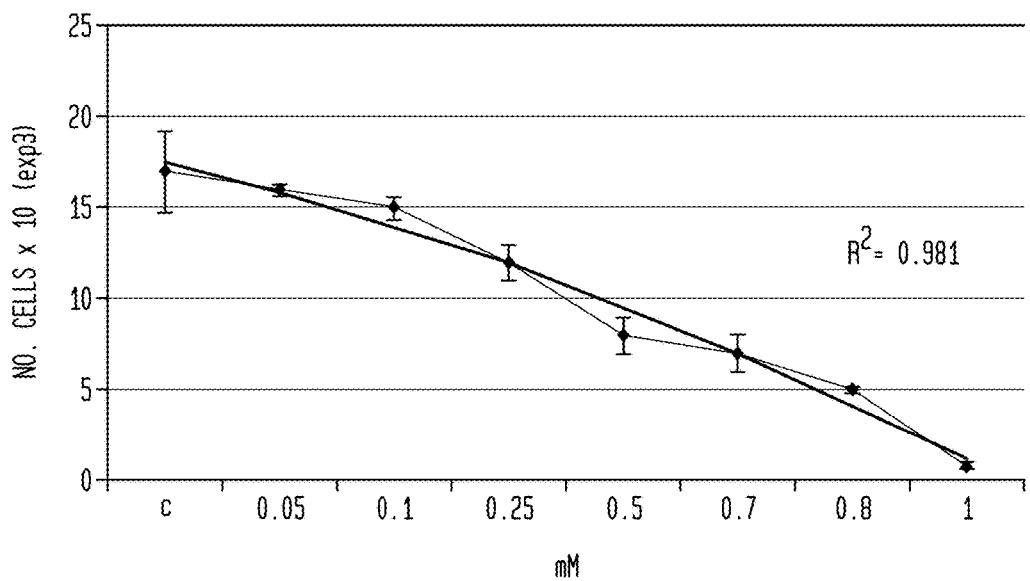
FIG. 1B is a graphical representation of the effect of RB10 on cell adhesion in murine B16F10-Nex2.1.
Figure 1C:
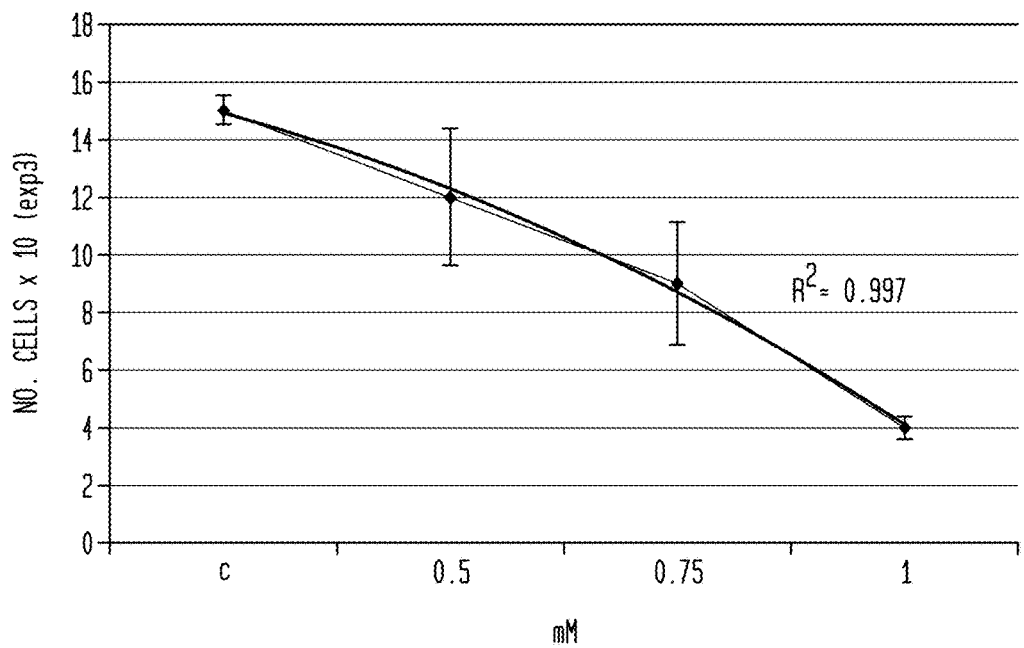
FIG. 1C is a graphical representation of the effect of RB9 on cell adhesion in human U87MG glioblastoma.
Figure 1D:
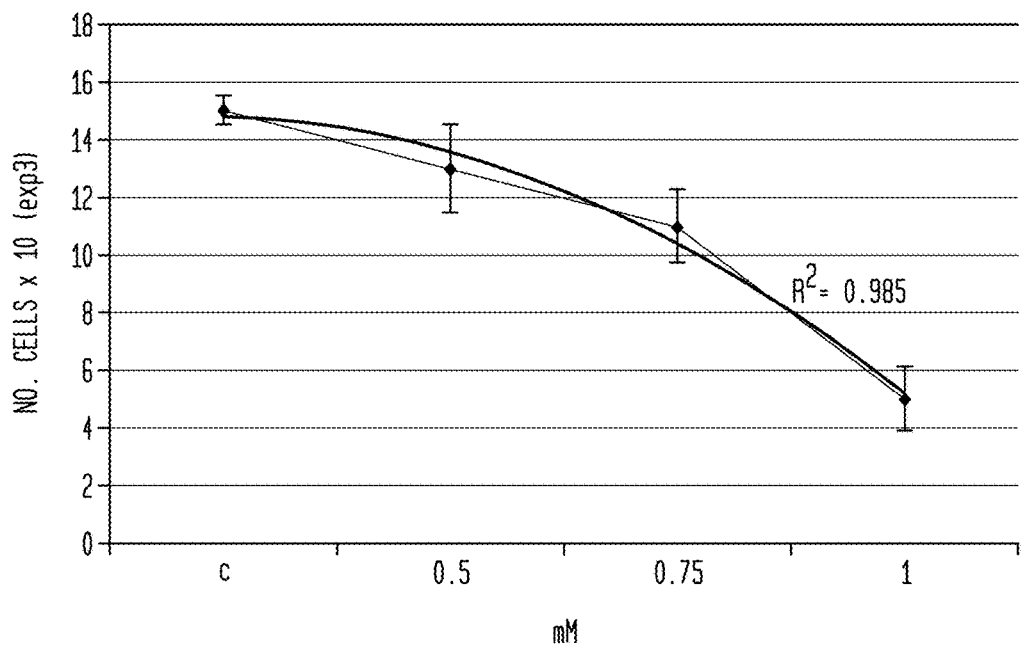
FIG. 1D is a graphical representation of the effect of RB10 on cell adhesion in human U87MG glioblastoma.
Figure 2A:
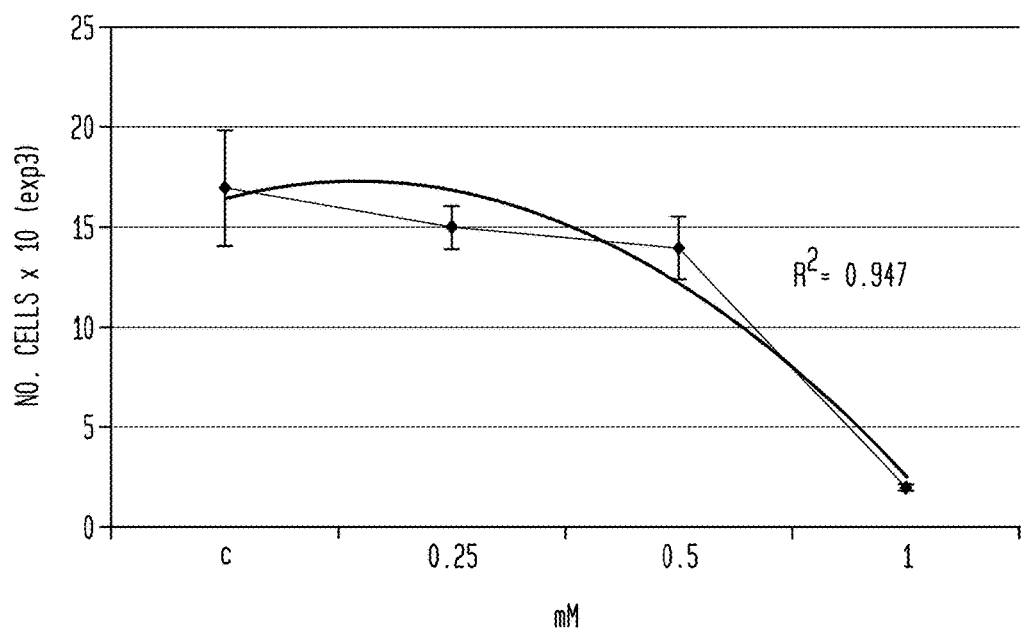
FIG. 2A is a graphical representation of the effect of RB9 on cell adhesion in human SKBR3 breast cancer.
Figure 2B:
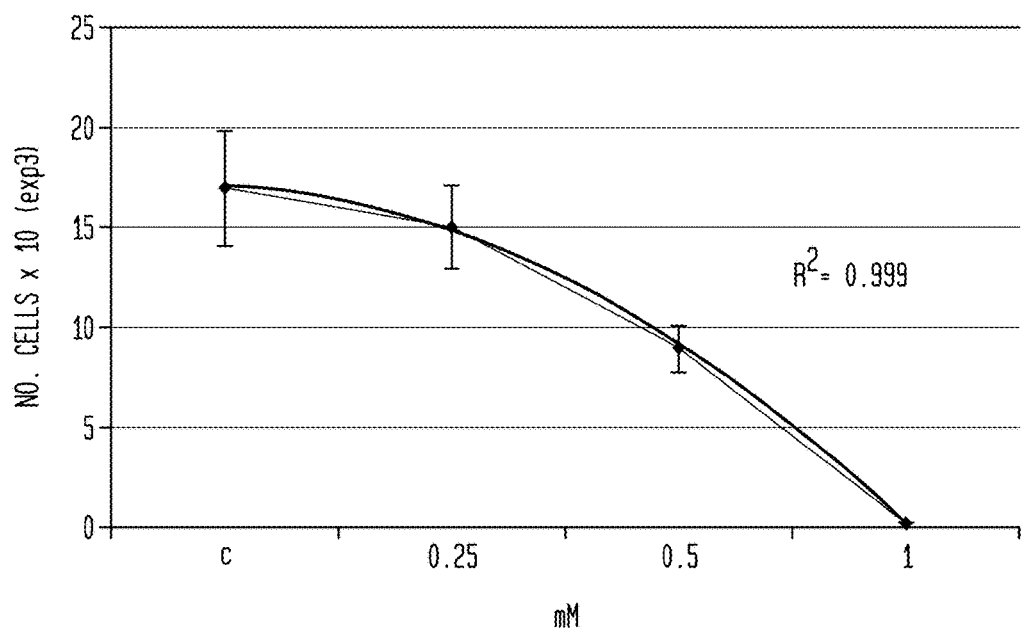
FIG. 2B is a graphical representation of the effect of RB10 on cell adhesion in human SKBR3 breast cancer.
Figure 2C:
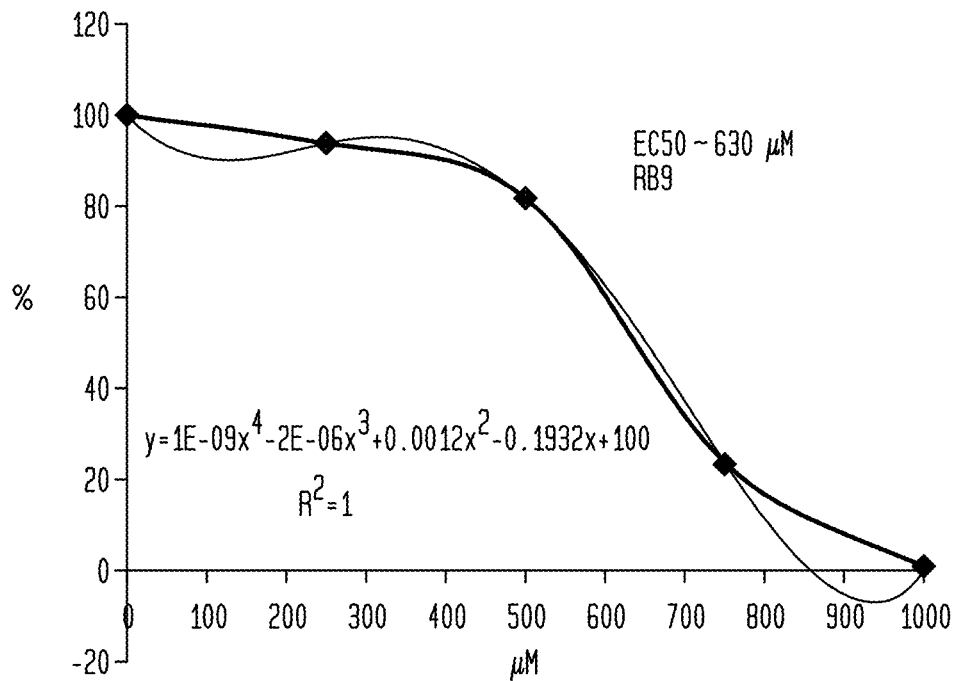
FIG. 2C is a graphical representation of the effect of RB9 on cell adhesion in human A2058 melanoma.
Figure 2D:
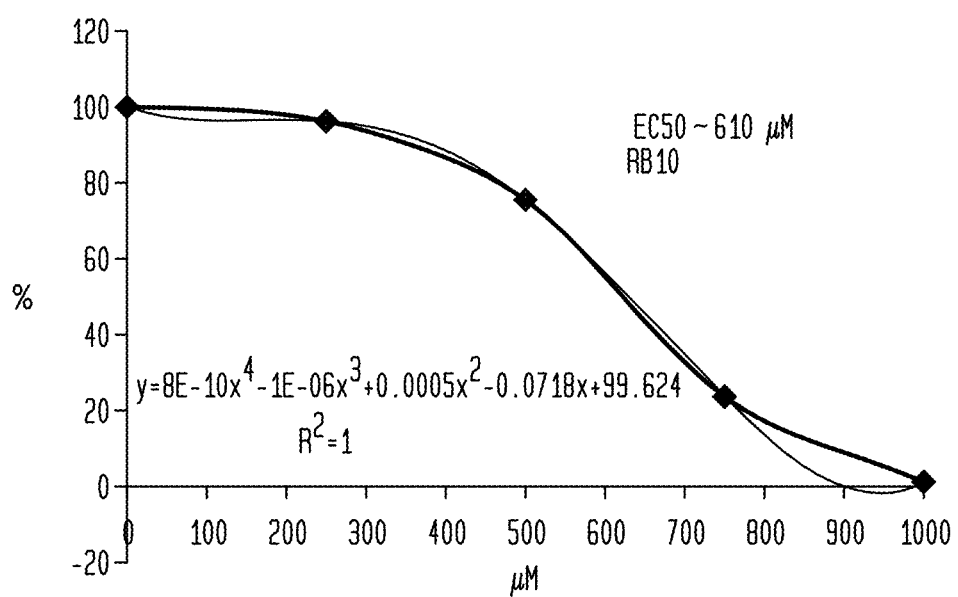
FIG. 2D is a graphical representation of the effect of RB10 on cell adhesion in human A2058 melanoma.

The below definitions serve to provide a clear and consistent understanding of the specification and claims, including the scope to be given such terms.

By the phrase "tumor cell cytotoxicity," different effects are referred to, including growth inhibition, cell cycle arrest, inhibition of cell motility, increase in cell adherence, inhibition of cell invasion through a matrix substrate, receptor induced cell death, interference in the cell metabolism and signaling pathways leading to senescence or death. These effects can be studied either in vitro or in vivo.

The term "peptide" as used herein means a compound that is made up of two or more amino acids joined by covalent bonds which are formed by the elimination of a molecule of H2O from the amino group of one amino acid and the carboxyl group of the next amino acid. For the purposes of the present subject matter, a peptide may be in a linear or cyclic array of amino acid residues, i.e., the ends of the linear peptide or the side chains of amino acids within the peptide may be joined, e.g., by a chemical bond.

The term "isolated" for purposes of the present subject matter refers to a state of biological materials (e.g., nucleic acid, peptide or protein) that have been removed from their original environment (the environment in which it is naturally present), or the state where the materials separately exist from the original environment. For example, a peptide present in the natural state in a plant or an animal is not isolated; however, the same peptide separated from the adjacent amino acids in which it is naturally present, is considered "isolated." The terms "isolated peptides" for the purposes of the present subject matter may include those prepared or synthesized by a known method to be corresponding to the natural peptides.

The phrase "synthetic peptide" for purposes of the present subject matter refers to a peptide prepared by a known chemical reaction of amino acids or by isolation and purification of a biological material as described above.

The phrase "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

The term "derivative(s)" of a peptide used herein refers to a peptide including variations of e.g., modification, substitution, deletion and/or addition in its amino acid sequence, made with regard to a reference peptide, which retains an identifiable relationship to the reference peptide. The modification can include chemical modification by, for example, glycosylation, PEGylation, PEG alkylation, alkylation, acetylation, amidation, glycosyl-phosphadylinositalization, farnesylation, ADP-ribosylation, sulfation, lipid attachment, hydroxylation, and/or phosphorylation. This term is understood as being exchangeable with the term "functional analogue."

As used herein, the terms "administering," "administration," and like terms, refer to any method which, in sound medical practice, delivers the presently provided composition to a subject in such a manner as to provide a therapeutic effect. One aspect of the present subject matter provides for intravenous administration of a therapeutically effective amount of the present composition to a patient in need thereof.

As used herein the term "treating" includes prophylaxis of a tumor or cancer in a patient or a subject having a tendency to develop such tumor or cancer, and the amelioration or elimination of the developed tumor or cancer once it has been established or alleviation of the characteristic symptoms of such cancer.

As used herein the terms "tumor" or "cancer" refer to all types of tumor or cancer. In some embodiments, the term "tumor" refers to ovarian, lung, renal or colon carcinomas, glioblastomas, melanomas, astrocytomas, sarcomas, teratocarcinomas, choriocarcinomas or hematopoietic tumors. Likewise, the term "cancer" refers to ovarian cancer, lung cancer, kidney cancer, skin cancer, brain cancer, uterus cancer, breast cancer, colon cancer, prostate cancer, liver cancer, intestinal cancer, esophagus and stomach cancer, head and neck cancer, or leukemia. The terms "tumor" and "cancer" may be exchangeable with each other.

As used herein, the term "subject" refers to any subject, particularly a mammalian subject, for whom diagnosis, prognosis, or therapy is desired, for example, a human. The term can be used to refer to a "patient."

As used herein, the terms "carrier," "excipient," or "diluents" refer to any component of a pharmaceutical composition that is not the drug substance. Accordingly, the term "pharmaceutically acceptable carrier" refers to a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

The active agent is preferably administered in an effective amount. As used herein, the phrase "effective amount" refers to the quantity of a component which is sufficient to yield a desired therapeutic response without undue adverse side effects (such as toxicity, irritation, or allergic response) commensurate with a reasonable benefit/risk ratio when used in the presently described manner. For example, a "therapeutically effective amount," can be a sufficient amount of the active agent to cause regression of the tumor, or at least partially arrest the tumorigenesis and metastasis at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in, for example, Remington's Pharmaceutical Sciences.

Throughout the application, descriptions of various embodiments use the term "comprising," which will be understood by one of skill in the art that in some specific instances, an embodiment can alternatively be described using the language "consisting essentially of" or "consisting of."

Unless defined otherwise all technical and scientific terms used herein have the same meaning as commonly understood to one of ordinary skill in the art to which the presently described subject matter pertains.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Preparation of Peptides

The presently described bioactive peptides (SEQ ID NOs: 1-6) with sizes ranging less than 30 or 25 amino acids may be isolated or separated from the complementarity determining region (CDR) hypervariable domains of the RebMab 200 (huMX35), which is described in PCT/US2009/000576, with a known method for isolating, separating and purifying bioactive peptides, and they can be further modified. The presently described peptides may also be prepared by chemical synthesis or manufacture using recombinant DNA technology. For example, the peptides can be obtained by methods using azide, acid chloride, acid anhydride, compound acid anhydride, DCC, activated ester, Woodward's reagent K, carbonylimidazole, deoxidixation, DCC/HONB, BOP reagent, etc., as known in the art. Also, they can be prepared by chemical synthesis using an automated peptide synthesizer.

Following such a chemical reaction, the peptides can be separated and purified by a known purification method. An example of such purification methods can include a combination of solvent extraction, distillation, column chromatography, liquid chromatography, recrystallization and the like.

Further, recombinant expression systems in *E. coli* may be used to express the presently described peptides as fusion proteins, with a specific enzymatic cleavage site, for example, enterokinase. Next, the bacteria are broken and centrifuged and the resulting soup contains the fusion protein. The fusion protein can then be loaded on a specific affinity column, for example, a Ni2+ or glutathione column, to be eluted. After elution, the purified fusion protein is subjected to a specific enzymatic cleavage reaction. Then, the peptide is purified from the resultant mixture by HPLC or ion exchange chromatography. Methods involving conventional and analytical chemistry, molecular biological and cell biological techniques are described in detail in many publicly known references, including those listed herein.

The present subject matter provides use of a peptide of smaller than 30 or 25 amino acids for the production of a pharmaceutical composition for the treatment of a subject suffering from cancer. A preferred size of the antitumor peptides for inclusion in a pharmaceutical composition according to the present subject matter is at most 30 or 25 amino acids, preferably at most 20 amino acids, with smaller molecules of 10, 9, 8, 7, 6 or 5 amino acids in length being particularly effective.

Derivatives, Biodistribution and Pharmacokinetics

Derivatives (or functional analogues) of peptides may be prepared by, for example, substitution of an L-amino acid residue with a D-amino acid residue or other non-natural residues. By generating many positional derivatives of an original amino acid sequence and screening for a specific activity, an improved peptide, for example, comprising D-amino acids can be identified and used according to the present subject matter.

The derivatives or functional analogues can be peptidomimetic compounds that functionally or structurally resemble the original peptide taken as the starting point, but that are, for example, composed of non-naturally occurring amino acids or polyamides. With "conservative amino acid substitution", one amino acid residue is substituted with another residue with generally similar properties (size, hydrophobicity, and/or charge), such that the overall functioning of a peptide sequence having such substitution is likely not to be seriously affected. In "non-conservative amino acid substitution", one amino acid residue is substituted with another residue with generally different properties (size, hydrophobicity, and/or charge), such that the overall functioning of a peptide sequence having such substitution could be seriously affected. A derivative can also be provided by systematically altering at least one amino acid of the reference peptide. This can be done, for instance, by an Alanine scanning (Ala-scan) and/or replacement net analysis, in which each amino acid is replaced in turn with one of the 19 other aminoacid (or 21, if selenocysteine and pyrrolysine are included). With these methods, many different peptides may be generated, based on an original amino acid sequence but each containing a variation or substitution of at least one amino acid residue. This way, many positional variants of the original amino acid sequence are synthesized and/or enzymatically prepared.

Peptidomimetics further include pseudopeptides having surrogates for the peptide bonds between the original amino acids (see e.g. U.S. Pat. No. 6,689,753). Such surrogates for peptide bonds include, but are not limited to CH2, CH2CH2, CH=CH, C≡C, CH2NH, COCH2, CH2S, CH2SO2 and NHCO.

In the case of peptides targeting tumor cells directly, a prolonged blood circulation is needed and thus derivatives and/or conjugates are synthesized for increased stability. In one embodiment of the present subject matter, the peptides may be further modified or conjugated to obtain stabilized peptides. The introduction of D-amino acids, or pseudo amino acids, and peptide cyclization are the most common strategies to increase peptide stability (Adessi and Soto, Curr Med Chem. 9(9):963-78, 2002). A common modification is that of C—C cyclic peptides (as carried out in RB10a of SEQ ID NO: 3, giving rise to RB9 of SEQ ID NO: 8) that are also expressed on certain phage display libraries. Peptides can be altered in other ways to prevent degradation by endopeptidases and exopeptidases. These include N-terminal (acetylation, glycosylation) or C-terminal (amidation) modifications and the use of unnatural amino acids (e.g. β-amino and α-trifluoromethyl amino acids) at particularly labile sites within a peptide.

Arap et al. (Science 279: 377-380, 1998) have identified three main peptide motifs that targeted phages into developing tumors in vivo. Phage carrying SEQ ID NO: 34 home to several tumor types, including carcinoma, sarcoma, and melanoma in a highly selective manner, and homing is specifically inhibited by the cognate peptide. Peptides capable of mediating selective localization of phage to brain and kidney blood vessels have been identified and have shown up to 13-fold selectivity for these organs. One of the peptides displayed by the brain-localizing phage was synthesized and shown to specifically inhibit the localization of the homologous phage into the brain (Pasqualini and Ruoslahti, Nature 380: 364-366, 1996; Pasqualini et al., Nat. Biotechnol. 15: 542-546, 1997). These experiments, apart from identifying specific targets on tumor tissues for phage recognition, have also shown that the cognate peptides administered systemically recognize the same targets, implying also sufficient stability in vivo. Practically, when coated onto glutaraldehyde-fixed red blood cells, the peptide caused selective localization of intravenously injected cells into the target tissue.

In one embodiment of the present subject matter, provided are peptide derivatives and/or conjugates for use in clinical trials, which allow greater stability and improved pharmacokinetics. Such derivatives and/or conjugates may be synthesized based on the peptide sequences set forth as SEQ ID NOs: 1-6, particularly SEQ ID NO: 3. Such derivatives and/or conjugates are tested for tumor cell cytotoxicity and tumor cell inhibition of migration and metastasis. Once a derivative is selected based on increased half-life in vivo and anti-tumor activity, it becomes a candidate to be tested in patients. In the case of anti-metastatic peptides, one may expect it to be effective or useful in clinical trials for patients who had their primary tumor excised, or are in the stage of lymph node involvement or have limited tumor development with regional metastases or are undergoing chemotherapy. Selected peptides with antitumor activity in vitro and in vivo need to be evaluated, in parallel, for in vivo biodistribution and peptide pharmacokinetics.

In one embodiment of the present subject matter, the presently described peptides can be evaluated for their biodistribution and their pharmacokinetics. For these studies, the peptides should be appropriately labeled with biotin, radioactivity or another convenient tag. Biotinylated peptides can be recognized by streptavidin on ELISA plates or by binding to Sepharose-streptavidin beads incubated with body fluids and tissue homogenates. Elution of biotinylated peptides tightly bound to streptavidin-coated multiwell plates that can be achieved by means of 70% acetonitrile, 0.5% formic acid, 1 mM biotin aqueous solution, and peptides are identified by LC-MS. For instance, in the case of RebMab200 CDR H3, it can be readily labeled with 1251 as it has a tyrosine (Y) residue on it. Also, the N-terminal cysteine residue can be used for biotinylation using Pierce's reagent. Other suitable methodologies can also be used depending on the structure of the bioactive peptide.

Another approach for evaluation of biodistribution and specific tumor cell binding is the use of bacteriophage M13 as an expression vector. Accordingly, in one embodiment of the present subject matter, the presently described peptides can be evaluated using bacteriophage M13 for their biodistribution and specific target tumor cell binding. The plasmid that generates the phage upon transfection in *Escherichia coli* can be engineered so that the oligonucleotide encoding the peptide is fused to that encoding phage protein. A series of analogous peptides to be expressed by phages can also be constructed using various oligonucleotides. Phage distribution in vivo can be followed by viral titration.

Pharmacokinetics and biodistribution of peptides and the resulting uptake in tumor and normal tissues can be altered by both molecular size and ligand specificity, with molecular size affecting pharmacokinetics and organ uptake in a predictable manner. Increased molecular size can be achieved by conjugation of the peptide with polyethylene glycol (PEGylation) or serum albumin. In one embodiment of the present subject matter, the peptides can be conjugated. As larger proteins (>50 kDa) are not filtered out by the kidneys, PEG can serve to increase the hydrodynamic radius of peptide conjugates and prevent their renal clearance. In both cases it is important to test the activity of the conjugated peptide. Using nucleophilic amino acids (e.g. cysteine or unnatural amino acids), PEG can also be attached within a peptide sequence and, if it does not inhibit peptide function, then endopeptidases might also be excluded from degrading particularly labile internal residues. In one embodiment, the presently described peptides can form a fusion protein.

Non-covalent interactions are also possible. Fusion of a 20-amino-acid sequence to the C-terminal end of an anti-tissue factor Fab enabled non-covalent association with albumin in vivo and increased the half-life of the Fab~40-fold in rabbits (McFarland et al., Cancer Res. 67(1):254-61, 2007). A similar construction could be tested using the Ig-CDR fused at the C-terminal with SEQ ID NO: 35 to be associated with albumin to increase the half-life of the effector peptide. Genetic fusion of peptides to the Fc domain of human gamma immunoglobulin (IgG) is an alternative method to increase peptide molecular size. Fc fusion takes advantage of the IgG protection function of the neonatal Fc receptor (FcRn). Serum albumin, in addition to escaping renal clearance, is also recycled via FcRn by binding to a different surface of the receptor than IgG. The chemical conjugation of peptides to albumin by covalent linkage to the free cysteine at amino acid position 34 of albumin is also effective in extending therapeutic peptide half-life. A range of other strategies are being developed for extending plasma residence time.

Peptides selected for direct tumor cytotoxicity should not be immunogenic, and are thus unable to elicit a strong neutralizing antibody response or to be presented by MHC for cellular immune reactivity or mediating hypersensitivity reactions. Incorporation of D-amino acids in the peptide structure should lessen both the proteolytic cleavage and the immune reactivity of peptides. Other kinds of derivatization should be checked for immunogenicity as well.

Biological Activity

"Biological activity" in the context of the present subject matter is used to refer to the ability of peptides to invoke one or more of the cytotoxic effects listed herein in connection with the definition of a "therapeutically effective amount." In a specific embodiment, "biological activity" is the ability to inhibit neoplastic cell growth or proliferation. A preferred biological activity is inhibition, including slowing or complete stopping, of the growth of a target tumor (e.g., cancer) cell. Another preferred biological activity is cytotoxic activity resulting in the death of the target tumor (e.g., cancer) cell. Yet another preferred biological activity is the increase of cell adherence of the neoplastic cells. The present subject matter, in one aspect, provides a method for identifying one or more peptides; and/or determining the biological activity of one or more peptides, comprising, for instance, screening a peptide to determine the activity of the peptide; analyzing the result; and/or identifying one or more peptides having antitumor activity. The efficacy of the peptides against a particular tumor type may be determined either in vitro or in vivo, e.g., by submitting cells derived from the tumor to the presence or absence of the peptide in vitro or by treating a mouse challenged with a tumor and monitoring the tumor overtime, as described e.g. in Polonelli et al. (PLoS One. 3(6):e2371, 2008) and Dobroff et al. (Translat. Onc., 3: 204-217, 2010). In some embodiments, the antitumor peptides are those derived from RebMab200, particularly those derived from RebMab200 CDRs, particularly from CDR H3 (SEQ ID NO: 3), as set forth in SEQ ID NOs: 8, 9 and 14-33. Preferably, the peptides are those as set forth in SEQ ID NO: 3 (RB10a), SEQ ID NO: 8 (RB9), SEQ ID NO: 9 (RB10), SEQ ID NO: 16 (RB9 M3), SEQ ID NO: 24 (RB10A4), SEQ ID NO: 26 (RB10 A6) and SEQ ID NO: 31 (RB10 M3).

Inhibition of cell growth refers significant reduction of target cells, especially cancer cells, either in vitro or in vivo. Further information can be found in The Molecular Basis of Cancer, Mendelsohn and Israel, eds., Chapter 1, entitled "Cell cycle regulation, oncogens, and antineoplastic drugs" by Murakami et al., (WB Saunders: Philadelphia, 1995), especially p. 13.

The cell adherence of a cell line is said to be "increased" by a peptide treatment if an augment of the cell attachment is observed after cell cultivation and incubation with different concentrations of the peptide, in comparison with a negative control.

In one embodiment, a dose-dependent effect is observed: i.e. at a lower dose of the peptide, cells would be detached with trypsin/EDTA at rates inversely proportional to the peptide concentration.

In addition to, or instead of, testing the peptide for efficacy against a particular tumor cell type in vitro, the clinician can test the antitumor effects of the peptide in vivo. For in vivo tests, cells derived from a tumor type are injected into laboratory animals such as mice. The animals are then monitored to determine whether tumors arise at the site of injection, or elsewhere in the animal. Laboratory animals that are treated with a peptide after tumor cell inoculation typically will not develop tumors or will significantly reduce tumor formation.

Pharmaceutical Compositions

A composition containing an effective amount of the peptides described herein can be administered to a subject requiring treatment. The composition can be administered parenterally, intravenously, topically, orally, buccally, nasally, rectally, subcutaneously, intramuscularly, or intraperitoneally.

The composition of the treatment may be formulated to be compatible with the route of administration. The composition can be formulated as a tablet, capsule, solution, powder, inhalant, lotion, tincture, troche, suppository, or transdermal patch.

A solution for parenteral, intradermal, or subcutaneous administration may comprise, for example: a sterile diluent such as water, saline, glycerin, fixed oils, polyethylene glycols, propylene glycol, or other synthetic solvents; an antibacterial agents such as benzyl alcohol or methyl parabens; an antioxidant such as ascorbic acid or sodium bisulfite; a chelating agent; a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as mannitol, sorbitol, and sodium chloride, can be used to maintain isotonicity in the composition.

Sterility can be insured by filter sterilization of the solution. Alternatively, the solution can be produced from components that were individually filter-sterilized. A filter-sterilized component can be vacuum dried or freeze dried to produce a sterile powder. Such a powder can be rehydrated prior to injection with a sterile carrier solution.

Oral compositions include, for example: tablets; capsules; troches; suspensions; and solutions. The compositions may be fashioned with an inert diluent or an edible carrier. Capsules can be formulated by combining an appropriate diluent with a peptide or formulation thereof and filling the capsule with the mixture. Common diluents are starches such as powdered cellulose, or sugars such as sucrose, fructose, or mannitol. Tablets may be made by wet or dry granulation, by compression or by other known methods. In addition to the desired peptide/compound, compositions for tablets can include, for example: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature. Biodegradable polymers such as poly-D,L-lactide-co-glycolide or polyglycolide, can be used as a matrix to delay the release of the composition.

For administration by inhalation, the compounds may be delivered, for example, in the form of an aerosol spray from pressured container dispenser, which contains a suitable propellant, e.g., a gas, or by other known methods. For example, administration can also be transmucosal, e.g., with a nasal spray or suppository, or by transdermal means, e.g., as a salve, ointment, gel, or cream. Such modes of administration can use formulations comprising, for example, bile salts, and fusidic acid derivatives.

Sustained-release preparations may also be prepared. Suitable examples of sustained-release preparations include semi-permeable matrices of solid hydrophobic polymers containing the peptide, which matrices are in the form of shaped articles, e.g., films, or microcapsules. Examples of sustained-release matrices include polyesters, hydrogels (for example, poly(2-hydroxyethyl-methacrylate), or poly(vinylalcohol), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

Also provided is the use of an antitumor peptide, preferably one derived from RebMab200, for the production of a pharmaceutical composition for the treatment of cancer, preferably a metastatic carcinoma.

Mode of Administration and Method of Treatment

The peptides described herein can be administered, for example, by bolus injection, by continuous infusion, for example, so as to prolong contact with the epidural region or by other known methods. The peptide can be infused for any amount of time. Dosage and timing of administration can be modified according to the needs of the particular subject, e.g., within the framework of standard clinical protocols for treating pain. The peptide can also be delivered by intrathecal routes, and into the bloodstream. In addition, implantable or body-mountable pumps can be used to deliver the peptide described herein at a controlled rate. Alternatively, prolonged administration can be achieved by art-known depot or sustained release formulations.

Single or multiple administrations of the peptide compositions can be carried out with dose levels and pattern being selected by the treating physician. In any event, the pharmaceutical formulations should provide a quantity of peptide sufficient to effectively treat the patient. Administration should begin at the first indication of undesirable cellular proliferation or shortly after diagnosis, and continue until symptoms are substantially abated and for a period thereafter. In well established cases of cancer, loading doses followed by maintenance doses will be required.

In addition, provided is a method of treating or inhibiting tumor growth, comprising administering to a subject in need of such treatment an effective amount of at least one antitumor peptide or a derivative or a functional analogue thereof comprising or consisting of the amino acid sequences represented by SEQ ID NOs: 1-33 together with a pharmaceutically acceptable diluent to the subject. A preferred size of an antitumor peptide for inclusion in a pharmaceutical composition according to the present subject Smatter is at most 30 amino acids, preferably at most 20 amino acids, although smaller molecules of 19, 18, 17, 16, 15, 14, 13, 12, 11, 10, 9, 8, 7, 6 or 5 amino acids in length can be particularly effective.

Other therapeutic regimens may be combined with the administration of the antitumor peptides of the present subject matter. For example, the patient to be treated with such antitumor peptides may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service, ed., M. C. Perry, Williams & Wilkins, Baltimore, Md. (1992). The chemotherapeutic agent may precede, or follow administration of the antitumor agent of the present subject matter, or may be given simultaneously therewith.

It may be desirable to administer antibodies also against tumor associated antigens, such as antibodies which bind to the ErbB2, EGFR, ErbB3, ErbB4, or vascular endothelial factor (VEGF). Alternatively, or in addition, two or more antibodies binding the same or two or more different cancer-associated antigens may be co-administered to the patient. Sometimes, it may be beneficial to also administer one or more cytokines to the patient. In a preferred embodiment, the anti-cancer agents herein are co-administered with a growth inhibitory agent. For example, the growth inhibitory agent may be administered first, followed by the administration of an antitumor peptide of the present subject matter. Simultaneous administration or administration of the antitumor peptide first is also contemplated. Suitable dosages for the growth inhibitory agent are those presently used and may be lowered due to the combined action (synergy) of the growth inhibitory agent and the peptides herein.

Dosage

An appropriate dosage for treatment must be determined. Determination of the amount or dose required to treat an individual subject is routine to one skilled in the art, e.g., a physician, pharmacist, or researcher.

For the prevention or treatment of disease, the appropriate dosage of an antitumor peptide herein will depend on the type of disease to be treated, as defined above, the severity and course of the disease, whether the agent is administered for preventive or therapeutic purposes, previous therapy, the patient's clinical history and response to the agent, and the discretion of the attending physician. The peptide is suitably administered to the patient at one time or over a series of treatments. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in Toxicokinetics and New Drug Development, Yacobi et al., eds., Pergamon Press, New York 1989, pp. 42-96.

The toxicity and therapeutic efficacy of the peptide and/or peptide formulations may also be determined Routine protocols are available for determining the LD50 (the lethal dose to 50% of the population) and the ED50 (the dose therapeutically effective in 50% of the population) in non-human animals. The therapeutic index is measured as the ratio of the LD50/ED50. Suitable ratios include, for example, ratios greater than about 2, 5, 10, 50, or 100. Compounds, formulations, and methods of administration with high therapeutic indices can be determined, as such treatments have little toxicity at dosages which provide high efficacy. Compounds with toxic or undesirable side effects can be used, if means are available to deliver the compound to the affected tissue, while minimizing damage to unaffected tissue, e.g., endothelial tissue. In one embodiment, the presently described peptides show ED50 value of about 920 to 930 µM (see FIG. 7).

In formulating a dosage range for use in humans, the effective dose of a peptide preparation can be estimated from studies with laboratory animals, e.g., as described below. For example, therapeutically effective dosages in cell culture assays include, for example, about 0.1 mM to 1 mM, preferably 0.25 mM to 1 mM of the peptide, and ranges there-between. A dose can be formulated in an animal in order to achieve a circulating plasma concentration of inhibitor that falls in this range. An exemplary dose produces a plasma concentration which exceeds the IC50 (i.e., the concentration of the test compound which achieves a half-maximal inhibition of a symptom) as determined in cell culture assays. The circulating plasma concentration can be determined, for example, by obtaining a blood sample, and by analyzing the sample using an antibody based specific ELISA assay or with high performance liquid chromatography or mass spectroscopy.

Alternatively, the dose can be estimated from tests in an animal model, as described below. Alleviation of symptoms is observed when mice receive a peptide or pharmaceutical composition at a dose of at least about from 1 µg/kg up to 10 mg/kg. For example, the dose may be of 6 mg/kg for a free, underivatized or unconjugated peptide, susceptible to plasma hydrolysis and renal clearance. The interrelationship of dosages for animals and humans (based on milligrams per meter squared of body surface) is described by, for example, Freireich et al., Cancer Chemother. Rep. 1966, 50, 219. Body surface area may be approximately determined from height and weight of the patient. See, e.g., Scientific Tables, Geigy Pharmaceuticals, Ardley, New York, 1970, 537. An effective dose for treating human patients cannot be estimated at present because it will depend on the stability of the peptide derivative used and its pharmacokinetics. The peptide can be administered with a frequency or continuously in order to maintain a local concentration effective to reduce pain in the subject.

Depending on the method of administration, the appropriate dose can vary, e.g., from about 1 µg/kg/day to about 10 mg/kg/day. Also, considering the low immunogenic nature of small peptides, dosing up to 100 mg/kg with small peptides, and in some cases when need for treatment is determined to be acute considering the condition of the subject in need of treatment, of up to 200 mg/kg, 500 mg/kg or even 1 g/kg will be possible.

The dose for a patient can be optimized while the patient is under care of a physician, pharmacist, or researcher. For example, a relatively low dose of the peptides described can be administered initially. The patient can be monitored for symptoms and sensation of pain as described below. The dose can be increased until an appropriate response is obtained. In addition, the specific dose level for any particular subject can vary depending on the age, body weight, general health, gender, and diet of the subject, the time of administration, the route of administration, the rate of excretion, and other drugs provided in combination.

The following examples are provided by way of illustration and are not intended to limit the scope of the claims.

EXAMPLES

Material and Methods
Preparation of Tumor Cell Lines and Cell Culture.
Murine B16F10-Nex2.1 melanoma cells were cloned at the Experimental Oncology Unit, Federal University of Sao Paulo (UNIFESP). Human melanoma (A2058), human colon carcinoma (HCT-8), human breast carcinoma (MCF-7, MDA and SKBR3), human cervical carcinoma (SiHa) and ovary carcinoma (OVCAR-3) cells were provided by Ludwig Institute for Cancer Research, Sao Paulo, Brazil. All cell lines were cultured at 37° C., under humid atmosphere and 5% $CO_2$, in RPMI-1640 medium with 10 mM N-2-hydroxy-ethyl-piperazine-N-2-ethanesulphonic acid (HEPES), 24 mM sodium bicarbonate, 40 mg/L gentamycin, pH 7.2 and 10% FCS. HeLa cells (human cervical carcinoma) were provided by Dr. Hugo P. Monteiro, Department of Biochemistry, UNIFESP, and U87-MG cells (glioblastoma) were provided by Dr. Osvaldo K. Okamoto, USP. HeLa and U87-MG cells were maintained in DMEM medium supplemented as indicated above.

Tumor Cell Growth In Vitro and In Vivo
Details of the in vitro tumor cell growth, cytotoxicity tests, determination of viable cells and in vivo protection experiments with B16F10 cells in a mouse metastatic model are described in Polonelli et al. (PLoS One. 3(6):e2371, 2008) and Dobroff et al. (Translat. Onc., 3: 204-217, 2010).

Cell Migration Assay
For the migration studies, $5 \times 10^5$ or $10^6$ cells were distributed on 6-well plates and let them to adhere for 2 hours at 37° C./5% $CO_2$. The culture medium was changed and the peptide was added at 500 µM overnight. The cell monolayer was "wounded" with a P1000 tip and incubated for 24 hours. Images of untreated cells (control) and peptide treated cells were captured with a JENOPTIK camera. Cell numbers (nuclei) were determined using the Pixcavator software version 5.0.

Example 1

Identification and Preparation of the Peptides

The RebMab 200 (huMX35) sequence of the variable region (PCT/US2009/000576) was studied for the CDR domains and the corresponding peptides were selected for peptide synthesis.

Seven (7) peptides were synthesized with high (>95%) purity (purchased from Peptide 2.0 Inc. Chantilly, Va., USA).

| RB8 | AIYPGNGDTSYKQKFRG-NH$_2$ | (H2) | (SEQ ID NO: 7) |
|---|---|---|---|
| RB9 | CARGETARATFAYWGQGC-NH$_2$ | (H3) | (SEQ ID NO: 8) |
| RB10 | CARGETARATFAYWGQG-NH$_2$ | (H3) | (SEQ ID NO: 9) |
| RB10a | CARGETARATFAYWGQG | (H3) | (SEQ ID NO: 3) |
| RB11 | GYTFTGYNIH-NH$_2$ | (H1) | (SEQ ID NO: 10) |
| RB12 | SASQDIGNFLN-NH$_2$ | (L1) | (SEQ ID NO: 11) |
| RB13 | YTSSLYS-NH$_2$ | (L2) | (SEQ ID NO: 12) |
| RB14 | QQYSKLPLT-NH$_2$ | (L3) | (SEQ ID NO: 13) |

Five (5) RB9 derivatized peptides were synthesized corresponding to the sequences below. D-Isomeric amino acids, D-Alanine (dA), D-Citrulline (dCit), D-Phenylalanine (dF), and D-Arginine (dR) were introduced both in RB9 and RB10 derivatized peptides.

| RB9 M1 | C(dA)RGETA(dCit)ATFAYWGQ(dA)C-NH$_2$ | (SEQ ID NO: 14) |
|---|---|---|
| RB9 M2 | C(dA)RGETA(dCit)AT(dF)AYWGQ(dA)C-NH$_2$ | (SEQ ID NO: 15) |
| RB9 M3 | C(dA)RGETARATFAYC-NH$_2$ | (SEQ ID NO: 16) |
| RB9 M4 | CARGETA(dCit)ATFAYWGQGC-NH$_2$ | (SEQ ID NO: 17) |
| RB9 M5 | C(dA)RGETARATFAYWGQGC-NH$_2$ | (SEQ ID NO: 18) |

Three (3) RB9 scramble peptides were synthesized corresponding to the following sequences:

| RB9 Scramble | CGTFEYRAQAGWAGRTAC-NH$_2$ | (SEQ ID NO: 19) |
|---|---|---|
| RB9 Sc2 | YWCRAAFTTEAGRACQGG-NH$_2$ | (SEQ ID NO: 20) |
| RB9 Sc3 | CFIARAGWYATEARGGQC-NH$_2$ | (SEQ ID NO: 21) |

Six (6) other peptides were synthesized corresponding to the alanine scanning series of RB10 with the following sequences:

| RB10 A1 | AARGETARATFAYWGQG-NH$_2$ | (SEQ ID NO: 22) |
|---|---|---|
| RB10 A3 | CAAGETARATFAYWGQG-NH$_2$ | (SEQ ID NO: 23) |
| RB10 A4 | CARAETARATFAYWGQG-NH$_2$ | (SEQ ID NO: 24) |
| RB10 A5 | CARGATARATFAYWGQG-NH$_2$ | (SEQ ID NO: 25) |
| RB10 A6 | CARGEAARATFAYWGQG-NH$_2$ | (SEQ ID NO: 26) |
| RB10 A8 | CARGETAAATFAYWGQG-NH$_2$ | (SEQ ID NO: 27) |

SEQ ID NO: 36 (excluding the fragment WGQG) SEQ ID NO: 28 with the following sequence was also synthesized:

| RB10 C-t | TFAYWGQG-NH$_2$ | (SEQ ID NO: 28) |
|---|---|---|

Four (4) RB10 derivatized peptides were synthesized corresponding to the sequences:

| RB10 M1 | CARGETA(dCit)AT(dF)AYWGQ(dA)-NH$_2$ | (SEQ ID NO: 29) |
|---|---|---|
| RB10 M2 | CA(dR)GETA(dR)AT(dF)AYWGQ(dA)-NH$_2$ | (SEQ ID NO: 30) |
| RB10 M3 | C(dA)RGETARATFAYWGQG-NH$_2$ | (SEQ ID NO: 31) |
| RB10 M4 | C(dA)RGETA(dCit)ATFAYWGQ(dA)-NH$_2$ | (SEQ ID NO: 32) |

One (1) RB10 scramble peptide was synthesized corresponding to the sequence:

| RB10 Scramble | CGTFEYRAQAGWAGRTA-NH$_2$ | (SEQ ID NO: 33) |
|---|---|---|

Briefly, no antitumor activity was found for RebMab 200 CDRs L1, L2, L3 and H1. Amidated RebMab 200 CDR H2 (SEQ ID NO: 7) shares up to sixteen (16) identical amino acids with similar H2 fragments from several murine antibodies of various specificities. It showed, however, no antitumor effect in contrast with strong activity previously described for the CDR H2 from mAb C7 (IgM) which has a different specificity and killed melanoma cells by apoptosis and angiogenesis inhibition (Polonelli et al., PLoS One. 3(6): e2371).

The CDR H3 of RebMab 200 (SEQ ID NO: 3) in an extended form that contains the conserved sequence WGXG, shares up to 82% identical amino acids with H3 sequences from a few other antibodies. However, the Kabat's based H3 sequence GETARATFAY shows partial (8-9/10) or full identity (9/9) with a number of proteins from diverse sources, mainly from prokaryotic organisms, with very few references to Ig sequences. Surprisingly, the extended H3 sequence of RebMab 200 showed antitumor effects even against tumor cells that would not react with mAb MX35 (e.g. melanoma), which suggests that it does not act as a microantibody and probably uses another cell surface receptor for binding to tumor cells.

Example 2

Cell Adherence Assay

Treatment of tumor cells with peptides RB9, RB10, and RB10a (SEQ ID NOs: 8, 9 and 3, respectively) rendered the cells showing dose dependent increase of adherence to the substrate (96-well plates, RPMI with 10% FCS culture medium). At a peptide concentration of 1 mM, most tumor cells displayed hyper-adherence and could not be suspended even by long term treatment with trypsin/EDTA. At a lower dose, cells would be detached with trypsin/EDTA at rates inversely proportional to the peptide concentration. Conceivably, peptides RB9 and RB10 affected the cytoskeleton dynamics of cells, thus signaling increased cell adhesion. Such response was seen in murine B16F10-Nex2.1 melanoma, human U87MG glioblastoma, A5028 melanoma, SKBR3 breast cancer, SiHa cervical and HCT colon cancer cells (FIGS. 1, 2, 3 and 4).

Both suspended and adherent cells were viable as shown by Trypan blue staining and MTT [3-(4,5-Dimethylthiazol-2-yl)-2,5-diphenyltetrazolium bromide; a yellow tetrazole] assay, indicating that the peptides are not directly cytotoxic but strongly stimulate cell adherence in a way that could inhibit migration and invasion of tumor cells. The H1 (RB11, SEQ ID NO: 10), H2 (RBB, SEQ ID NO: 7), L1 (RB12, SEQ ID NO: 11), L2 (RB13, SEQ ID NO: 12), L3 (RB14, SEQ ID NO: 13) peptides showed no antitumor activity and were used as negative controls.

Example 3

Effects of Peptides RB9 and RB10 on Murine Melanoma and Human Glioblastoma Cells B16F10-Nex2.1 cells ($5 \times 10^3$) and U87-MG cells ($1 \times 10^4$) were cultivated in 96-well plates and incubated with different concentrations of RB9 (SEQ ID NO: 8) and RB10 (SEQ ID NO: 9) from 0.01 to 1 mM (i.e., 0.01, 0.05, 0.1, 0.25, 0.7, 0.8 and 1 mM of RB9 and RB10 for B16F10-Nex 2.1 cells; and 0.25, 0.5, 0.75 and 1 mM of RB9 and RB10 for U87-MG cells). After 18 hours incubation, viable cells detached with trypsin/EDTA were counted using Trypan blue exclusion staining. All assays were performed in triplicate in two independent experiments. The results are shown in FIGS. 1A to 1D.

Example 4

Effects of RB9 and RB10 on Human Breast Cancer SKBR3 and Melanoma A2058 Cells SKBR3 cells ($1 \times 10^4$) were cultivated in 96-well plates and incubated with RB9 (SEQ ID NO: 8) and RB10 (SEQ ID NO: 9). After 18 hours incubation, viable cells detached with trypsin/EDTA were counted using Trypan blue exclusion staining. Assays were performed in triplicate in two independent experiments. The A2058 human melanoma cells ($1 \times 10^4$) were incubated for 4 hours at 37° C. in a humidified chamber with 5% $CO_2$. Fresh media containing different peptide concentrations of RB9 and RB10 ranging from 0 to 1 mM (i.e., 0, 0.25, 0.5 and 1 mM) was added to the wells and incubated for 24 hours. The media was then aspirated, cells were detached with 30 µl/well of trypsin-EDTA for five minutes at 37° C. and viable cells were counted in a Neubauer chamber using Trypan blue. As shown in FIGS. 2A-2D, 50% of cells were trypsin-EDTA resistant at 630 and 610 µM RB9 and RB10, respectively.

Example 5

Detection of Peptide-Treated Hyper Adherent SiHa Cells

Viable SiHa cells ($1 \times 10^4$)/well were distributed on a 96-well culture plate and incubated for 4 hours at 37° C. in a humidified chamber with 5% $CO_2$. Fresh medium containing different peptide concentrations of RB9 (SEQ ID NO: 8) and RB10 (SEQ ID NO: 9) ranging from 0 to 1 mM (i.e., 0, 0.25, 0.5 and 1 mM) was added to the wells and incubated for 24 hours. The medium was then aspirated; cells were detached with 30 µl/well of trypsin-EDTA for five minutes at 37° C. and gently washed with PBS. Hyperadherent cells were incubated for 4 hours with 0.5 mg/mL of MTT [3-(4,5-dimethylthiazol-2-yl)-2,5-diphenyltetrazolium bromide] in fresh medium and formazan crystals were solubilized adding 1 volume of 10% SDS solution overnight. Intensity was measured using a plate reader at 570 nm. As shown in FIGS. 3A and 3B, RB10 was more effective than RB9 against SiHa cell line; at 500 µM it caused 80% and 30% respectively, of tumor cells to become resistant to trypsinization.

Example 6

Detection of Peptide-Treated Hyper Adherent HCT Cells

Viable HCT cells ($1 \times 10^4$)/well were distributed on a 96-well culture plate and incubated for 4 hours, following the same protocol of Example 5. As shown in FIGS. 4A and 4B, the effect of RB10 (SEQ ID NO: 9) was similar to RB9 (SEQ ID NO: 8) in HCT cell line, where 80% of cells were resistant to trypsinization at 500 µM peptide.

Example 7

In Vivo Antitumor Effects of RB9 and RB10

Figure 5:
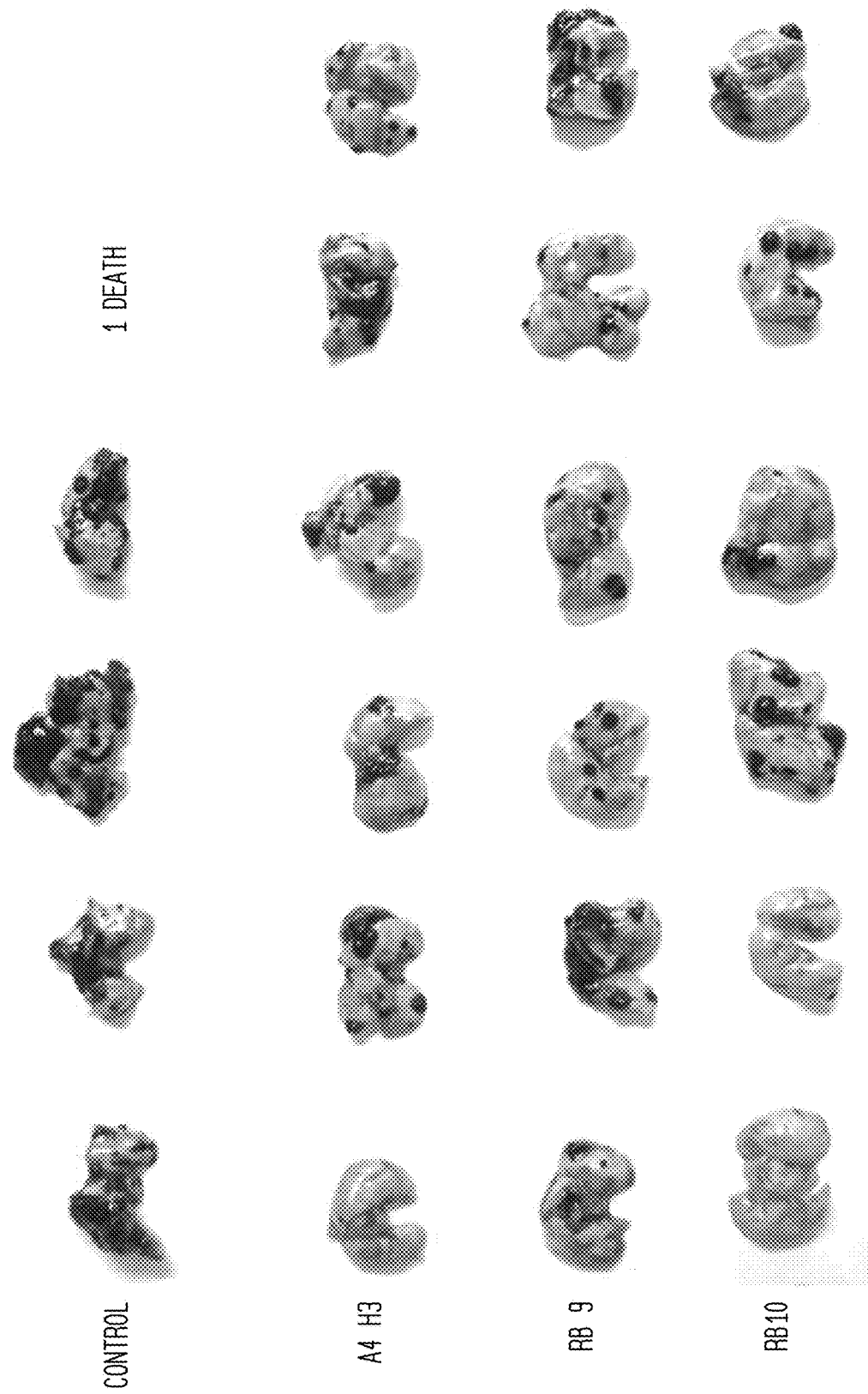
FIG. 5 displays in vivo antitumor effects of RB9 and RB10 on B16F10-Nex2 melanoma cells, which was treated with control, a true microantibody of a cytotoxic antimelanoma mAb (A4 H3), RB9 and RB10.

Peptides RB9 and RB10 along with the apoptotic peptide A4H3, a true microantibody of cytotoxic anti-melanoma mAb (A4) (Dobroff et al., Translat. Onc., 3: 204-217, 2010), were tested for their protective effects against lung colonization by B16F10-Nex2 melanoma cells ($2 \times 10^5$) injected intravenously in C57Bl/6 mice (6 animals/group). Peptides were intraperitoneally administered (250 µg i.p.) on days 1, 3, 5, 7, 9, 11 after tumor cell challenge. Lungs of peptide-treated animals are shown in FIG. 5 after 22 days of tumor challenge. As noticed, peptide treatment was interrupted 10 days before animal sacrifice.

Figure 6:
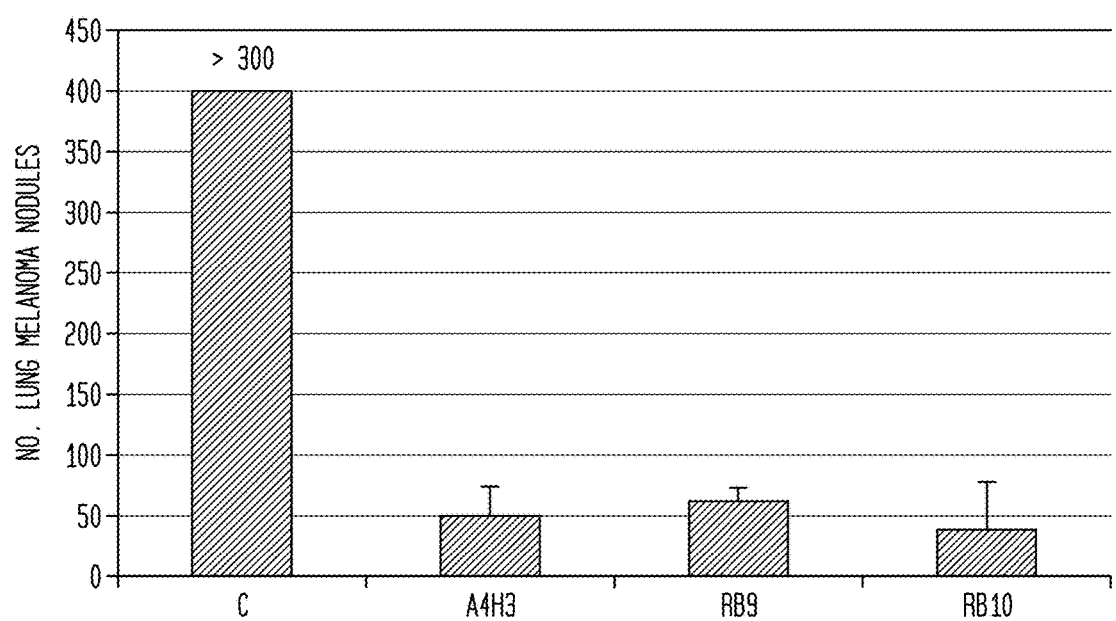
FIG. 6 is a graphical representation of lung melanoma nodules reduced by the treatment of RB9 and RB10 as compared with control and A4 H3.

Peptides RB9 (SEQ ID NO: 8) and RB10 (SEQ ID NO: 9) successfully protected against metastatic melanoma significantly reducing lung colonization. In vivo protection by peptides RB9 and RB10 (and A4H3 control) against lung colonization by B16F10-Nex2 melanoma cells ($2 \times 10^5$) injected intravenously in C57Bl/6 mice (6 animals/group) is shown in FIG. 6. The other 5 CDRs of RebMab200 (SEQ ID NOs: 7, 10, 11, 12, 13) were unprotective in vivo. Peptides were administered in the same way as described above, and the number of lung nodules was determined.

Protection by RB9 and RB10 was seen even when peptide treatment was interrupted 10 days before animal sacrifice, suggesting an early effect on tumor cell migration and invasion. These results point to a broad spectrum of reactivity of these peptides beyond that established for huMX35.

Figure 7A:
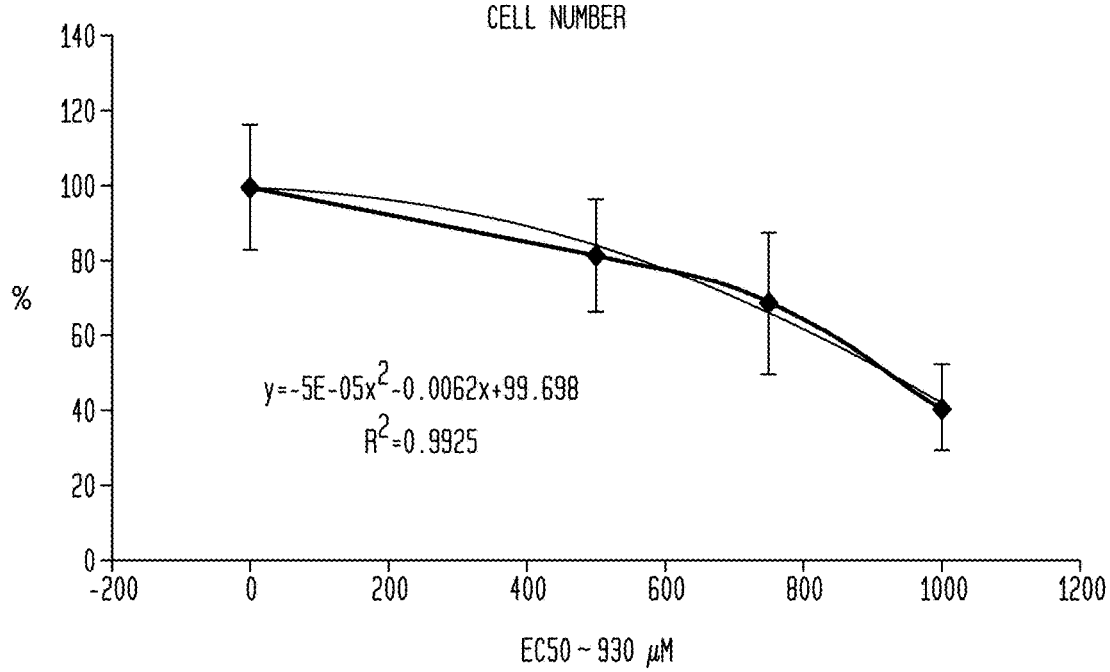
FIG. 7A is a graphical representation of a mild cytotoxicity of RB9 to human leukemia HL-60 cells measured by Trypan blue.
Figure 7B:
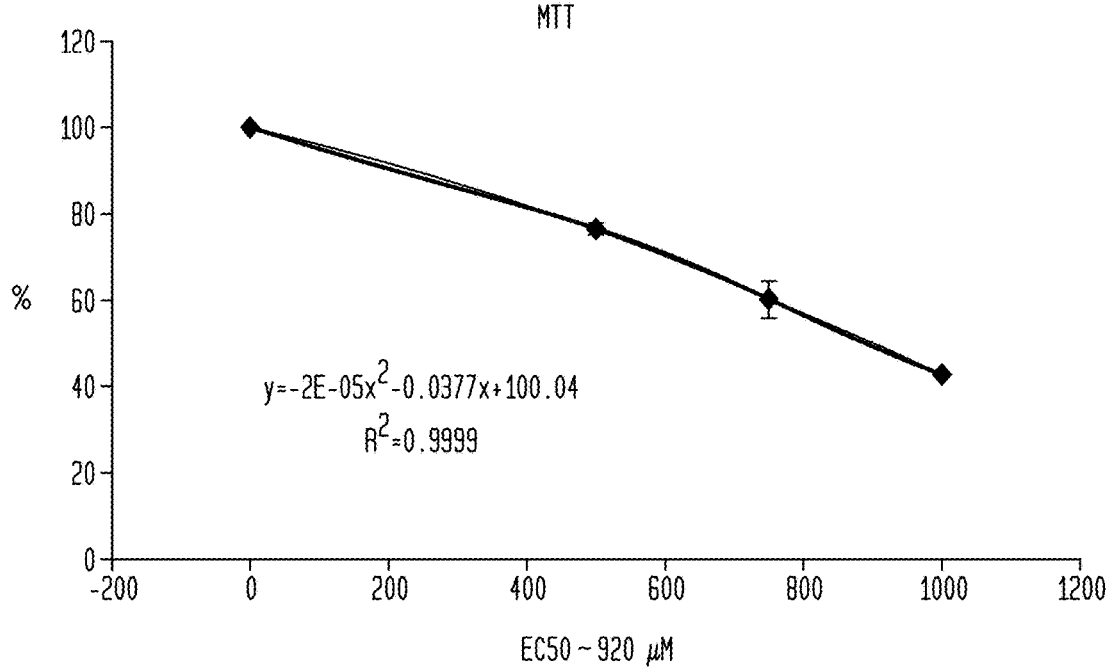
FIG. 7B is a graphical representation of a mild cytotoxicity of RB9 to human leukemia HL-60 cells measured by MTT assay.
Figure 8A:
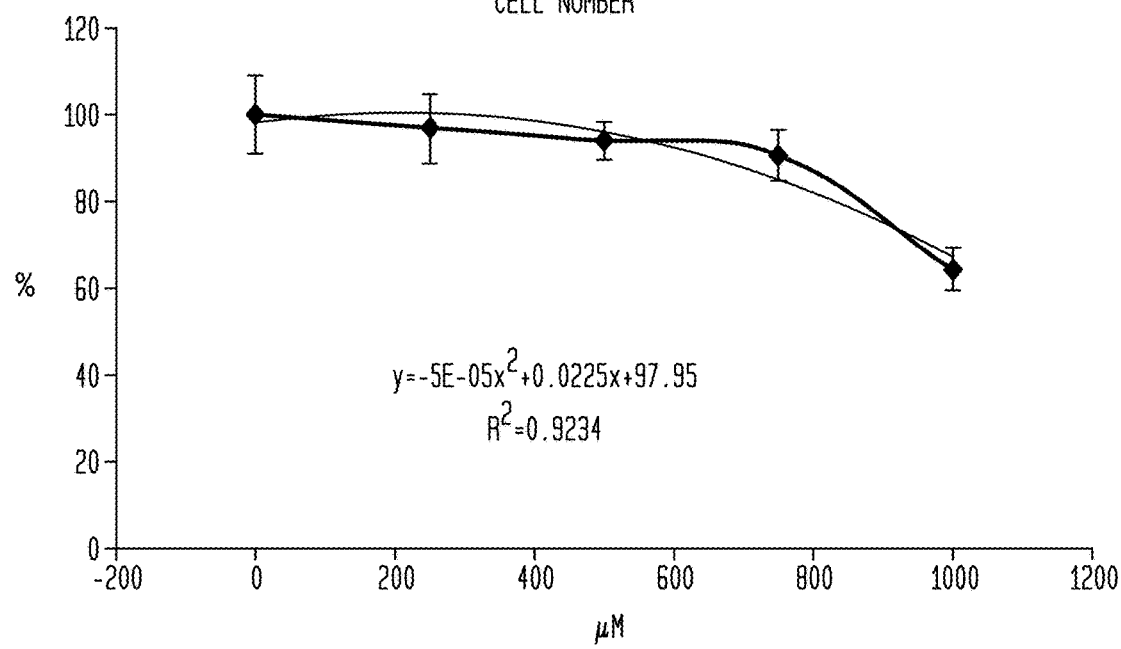
FIG. 8A is a graphical representation of lack of cytotoxicity of RB9 to human OVCAR-3 ovarian tumor cells measured by Trypan blue.
Figure 8B:
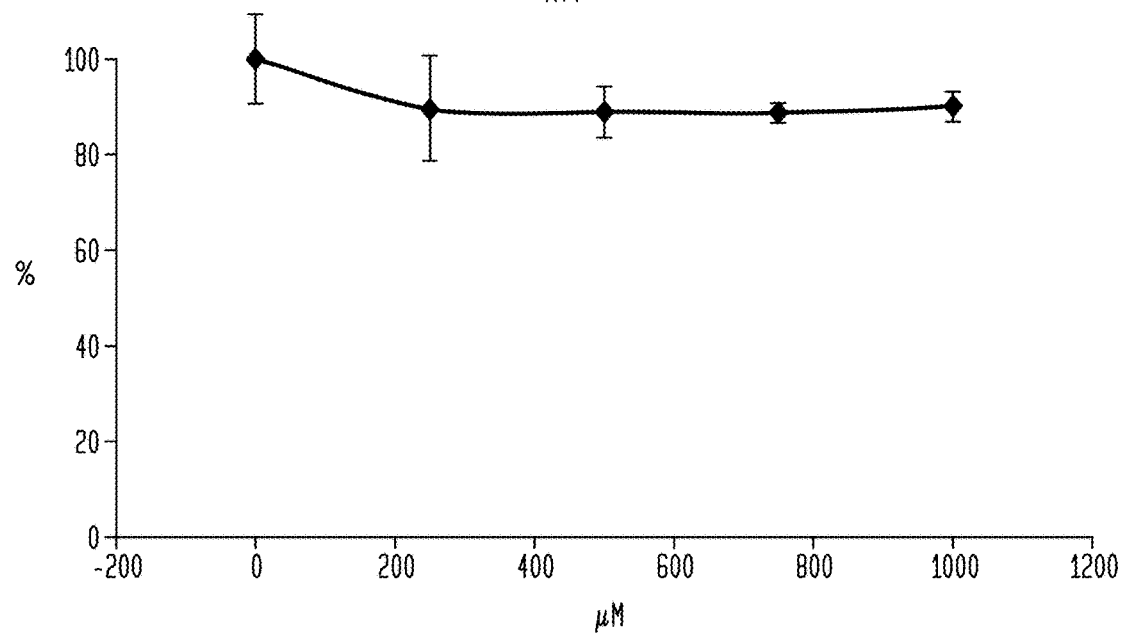
FIG. 8B is a graphical representation of lack of cytotoxicity of RB9 to human OVCAR-3 ovarian tumor cells measured by MTT assay.

Peptides RB9 and RB10 were mildly cytotoxic to human leukemia HL-60 cells growing in suspension (FIG. 7) and were inactive against OVCAR-3 ovarian cancer cells (FIG. 8). Peptide treated ovarian cancer cells were normally detached with trypsin/EDTA, unlike the other tumor cells tested suggesting a lack of effect of both peptides in these cells. Since huMX35 binds to but is not directly cytotoxic to OVCAR-3 ovarian cancer cells (data not shown), this experiment does not provide evidence that RB9 and RB10 could represent microantibodies functionally related to the original mAb. Competition experiments were run using cell ELISA, but RB10 reacted with a secondary antibody (i.e., anti-human IgG from GE Healthcare); thus, a different methodology will be required to answer this question. Nevertheless, peptides RB9 and RB10 reacted with a receptor expressed on tumor cells and strongly affected the cytoskeleton-dependent cell adhesion to the substrate. Such increased adhesion seems to inhibit metastasis, consistent with the inhibition of lung colonization by peptide-treated melanoma cells.

Example 8

Effect of RB9 on Human Leukemia Cells

Viable HL-60 cells ($1 \times 10^4$)/well were distributed on a 96-well culture plate and incubated for 4 hours with different concentrations of RB9 (SEQ ID NO: 8) ranging from 0 to 1 mM for 24 hours. Cell viability was directly measured by counting in a Neubauer chamber with Trypan blue or estimated by the colorimetric MTT assay. As shown in FIGS. 7A and 7B, RB9 reduced 50% the cell viability at 920-930 µM.

Example 9

Effect of RB9 on Ovarian Carcinoma Cells

Viable OVCAR-3 cells ($1 \times 10^4$)/well were distributed on a 96-well culture plate and incubated for 4 hours with different concentrations of RB9 (SEQ ID NO: 8) ranging from 0 to 1 mM for 24 hours. Cells were detached with 30 µl/well of trypsin-EDTA for five minutes at 37° C. and counted in a Neubauer chamber with Trypan blue or estimated by the colorimetric MTT assay. As shown in FIG. 8, RB9 had low effect on this lineage with no significant decrease in viability by the MTT assay. At 1 mM of RB9, most cells were unaffected by the hyper-adherent effect as shown in FIGS. 1-4.

Example 10

Alanine Scanning Series and Cell Adhesion Assay

The peptide RB10 (SEQ ID NO: 9) was engineered to replace each amino acid by alanine using Ala-scan methodology, and thus help evaluate the role of each amino acid on biological effect, specifically on the hyper-adherence observed with 1 mM peptide.

Figure 9:
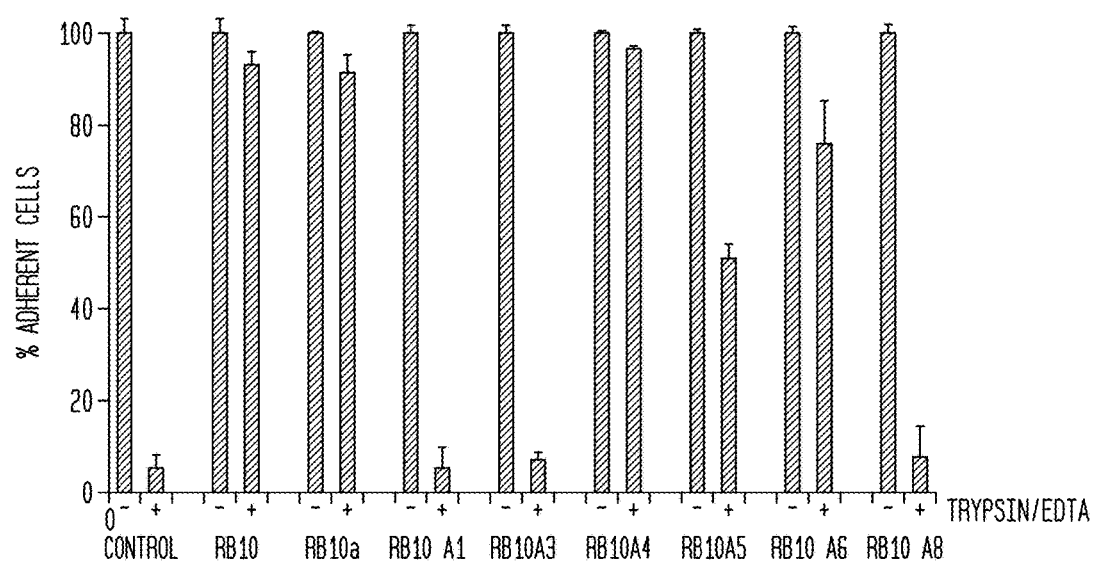
FIG. 9 is a graphical representation of cell adherent effects by RB10 derivatives for alanine scanning series: RB10a, RB10 A1, RB10 A3, RB10 A4, RB10 A5, RB10 A6 and RB10 A8, each at 1 mM concentration, as compared to control and RB10.

For this purpose, viable melanoma B16F10-Nex2 cells ($1 \times 10^4$)/well were distributed on a 96-well culture plate and incubated for 4 hours. Fresh media containing 1 mM of the alanine-scanning series for RB10 was added and incubated for 24 hours. Treated cells were detached with 30 µl/well of trypsin-EDTA for five minutes at 37° C. and gently washed with PBS. Cells were incubated for 4 hours with 0.5 mg/mL of MTT [3-(4,5-Dimethylthiazol-2-yl)-2,5-diphenyltetrazolium bromide] in fresh media and the formazan crystals were solubilized adding 1 volume of a 10% SDS solution overnight. Intensity was measured using a plate reader at 570 nm. As shown in FIG. 9, derivatives RB10 A4 (SEQ ID NO: 24) and RB10 A6 (SEQ ID NO: 26), as well as peptide RB10a (with a carboxylic end) (SEQ ID NO: 3), acted as peptide RB10 (SEQ ID NO: 9) did, inducing high trypsin/EDTA-resistant cell adherence. Alanine-substituted derivatives RB10 A1 (SEQ ID NO: 22), A3 (SEQ ID NO: 23), A8 (SEQ ID NO: 27), and less efficiently A5 (SEQ ID NO: 25), rendered cells that, unlike RB10, were normally detached when treated with 1 mM peptide. The 100% value for each peptide represented the treated cells that had not been trypsinized.

Example 11

Inhibition of Tumor Cell Invasion

Figure 20:
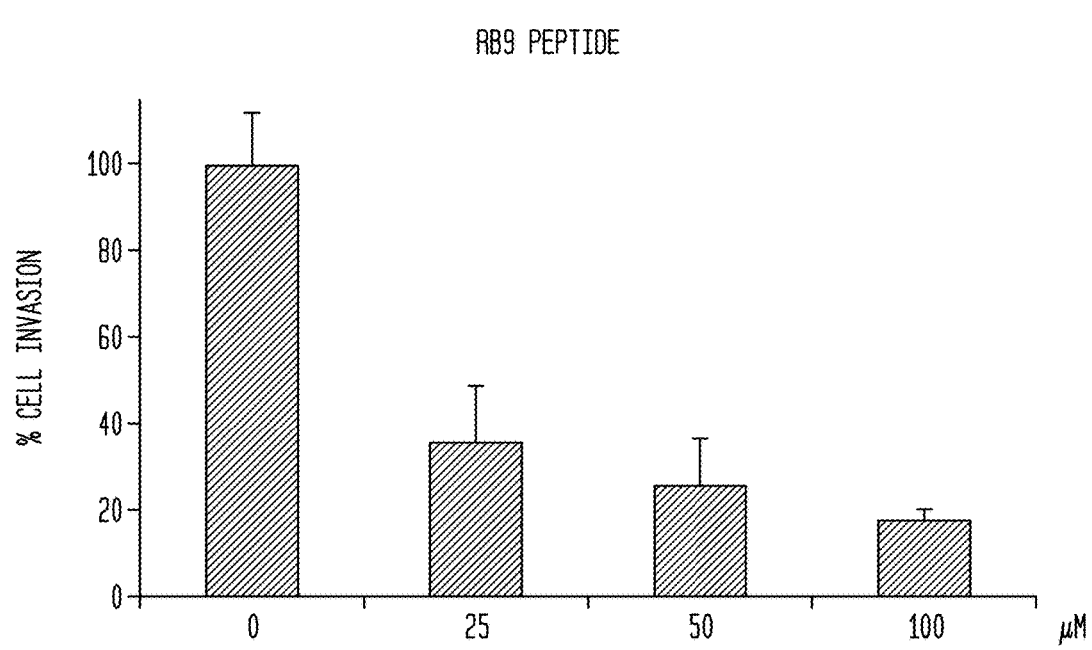
FIG. 20 is a graphical representation of RB9 dose-dependent inhibition of murine B16F10-Nex2 melanoma cells invasion through Matrigel.

A suspension of $2 \times 10^5$ B16F10-Nex2 cells in 500 µl of RPMI was incubated with 0.5 mM of RB9 and added to the upper chamber of an 8-µm Transwell (Becton-Dickinson) pre-coated with Matrigel (Becton-Dickinson). As a chemoattractant, 10% FCS in RPMI was used in the transwell lower chamber. After 24 hours at 37° C. in humidified atmosphere with 5% $CO_2$, non-invasive cells were excluded with a swab, and cells that crossed the membrane were fixed with methanol and stained with Giemsa. Cells were counted in each transwell membrane, and the numbers of invasive cells are expressed as percentages. The RB9 (SEQ ID NO: 8) peptide was able to inhibit tumor cell invasion of Matrigel in a transwell system Inhibition of B16F10-Nex2 cell invasion by RB9 was dose dependent with 60% inhibition at 25 M of RB9 (FIG. 20).

Example 12

Enhanced Superoxide Anion Production Shown in Dihydroethidium (DHE) Assay

The protective effect was shown in a metastatic syngeneic model of murine melanoma when administered intraperitoneally and the remarkable hyper-adherence of treated cells shown in in vitro tests suggests that RB9 (SEQ ID NO: 8) and RB10 (SEQ ID NO: 9) peptides interfere with cell migration and invasion by affecting cytoskeleton dynamics of the cells. Based on the internal interactions of components, such as, actin and peroxides in tumor cells, even leading to apoptosis, the production of anion superoxide in tumor cells treated with RB10 was examined by dihydroethidium (DHE) assay.

B16F10-Nex2 cells were treated with 1 mM RB10 for 18 hours or 5 mM $H_2O_2$ for 20 minutes. Treated cells with peptide or $H_2O_2$ and untreated cells were then incubated with DHE. Conversion of DHE to ethidium by oxidation was observed using fluorescence microscopy (Magnification 600×).

Figure 10A:
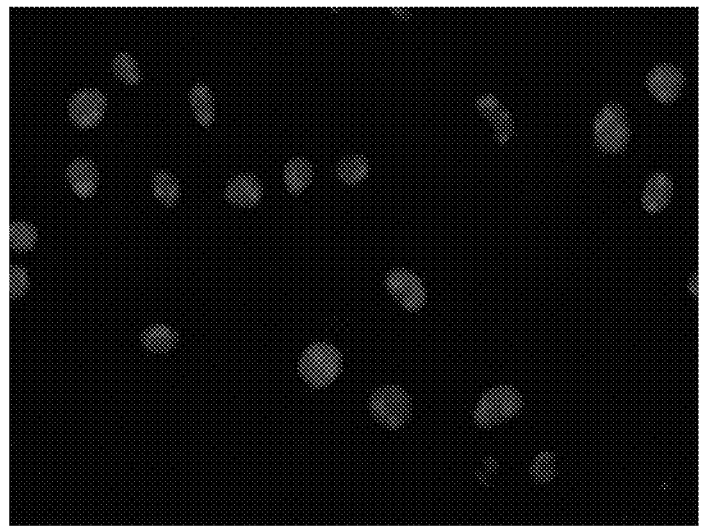
FIG. 10A is a photographical representation of in vitro production of anion superoxide in untreated B16F10-NEx2 tumor cells (control).
Figure 10B:
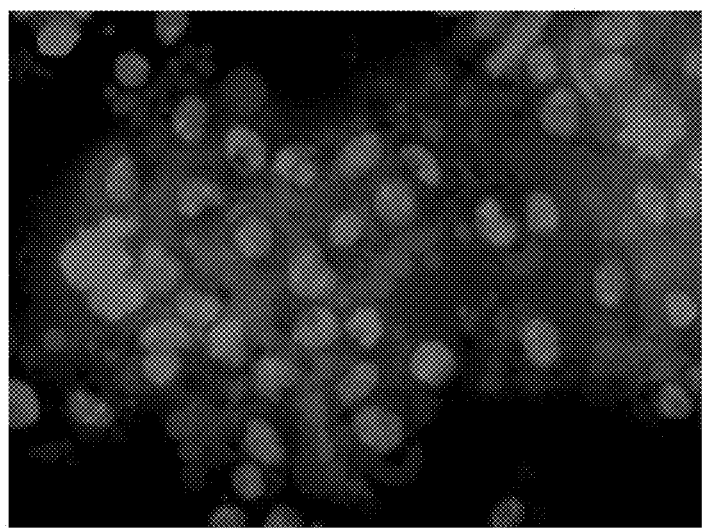
FIG. 10B is a photographical representation of in vitro production of anion superoxide in B16F10-NEx2 tumor cells treated with H2O2 (positive).
Figure 10C:
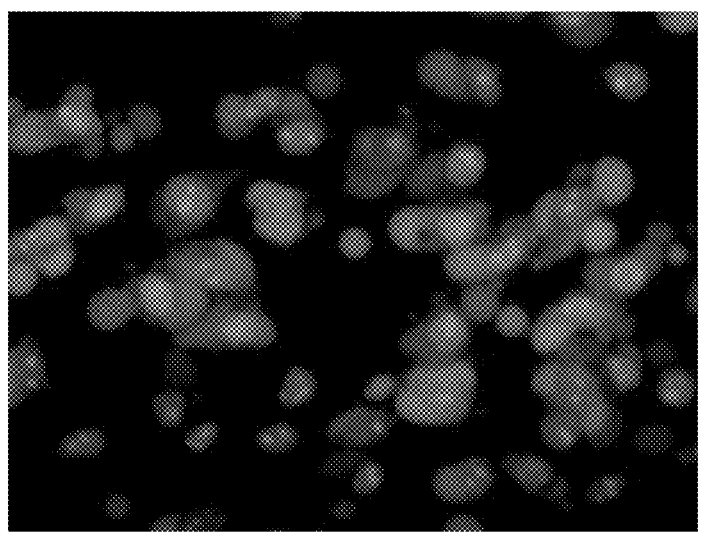
FIG. 10C is a photographical representation of in vitro production of anion superoxide in B16F10-NEx2 tumor cells treated with RB10.

The reaction with dihydroethidium was positive in these cells (FIG. 10).

Example 13

Peptide Stability—Peptide RB9 Degradation by Human Plasma

Peptides have variable half lives in the plasma due to the proteolytic activity and the renal filtration, which are relevant aspects in the pharmacokinetics of drug candidates. To study these aspects, peptide RB9 (2 mg) (SEQ ID NO: 8), which is more soluble than RB10 (SEQ ID NO: 9), was dissolved in 200 µL of MilliQ water and incubated with 1 mL of human plasma at 37° C. and the kinetics of degradation was followed up to 24 hours when the whole peptide was degraded.

Figure 11A:
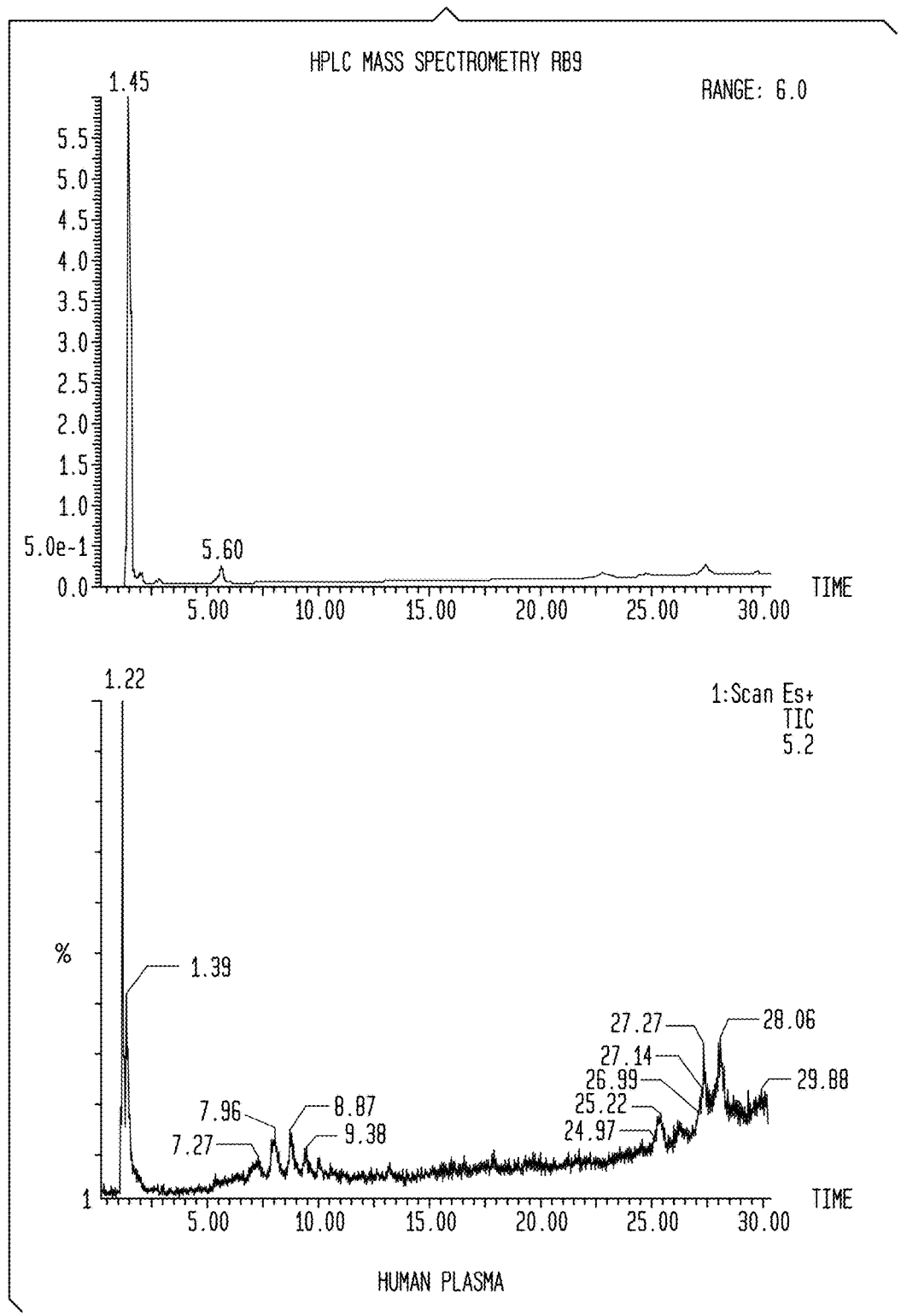
FIGS. 11A-11C are graphical representation of HPLC Mass Spectrometry for RB9 half life.
Figure 11B:
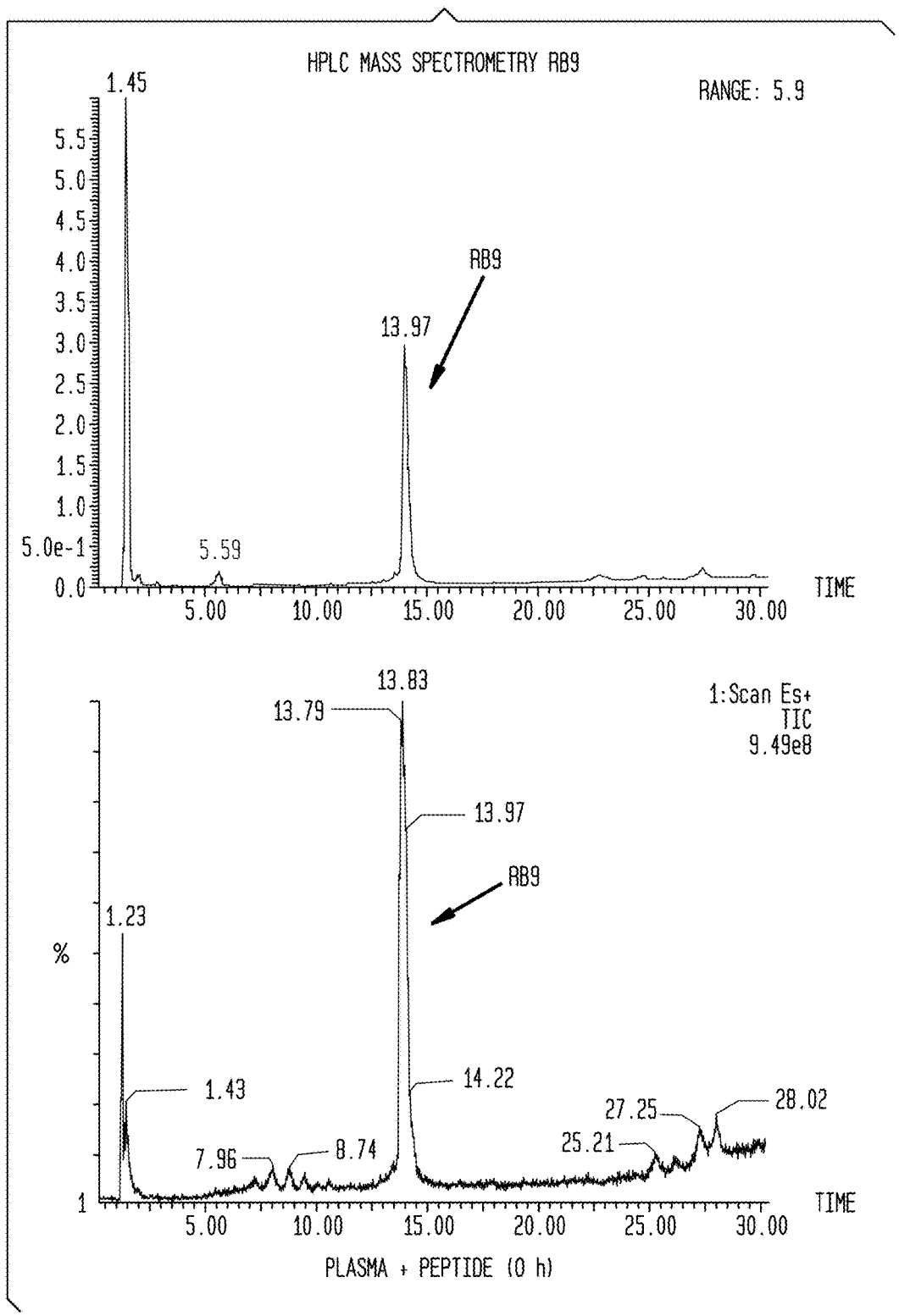
Figure 11C:
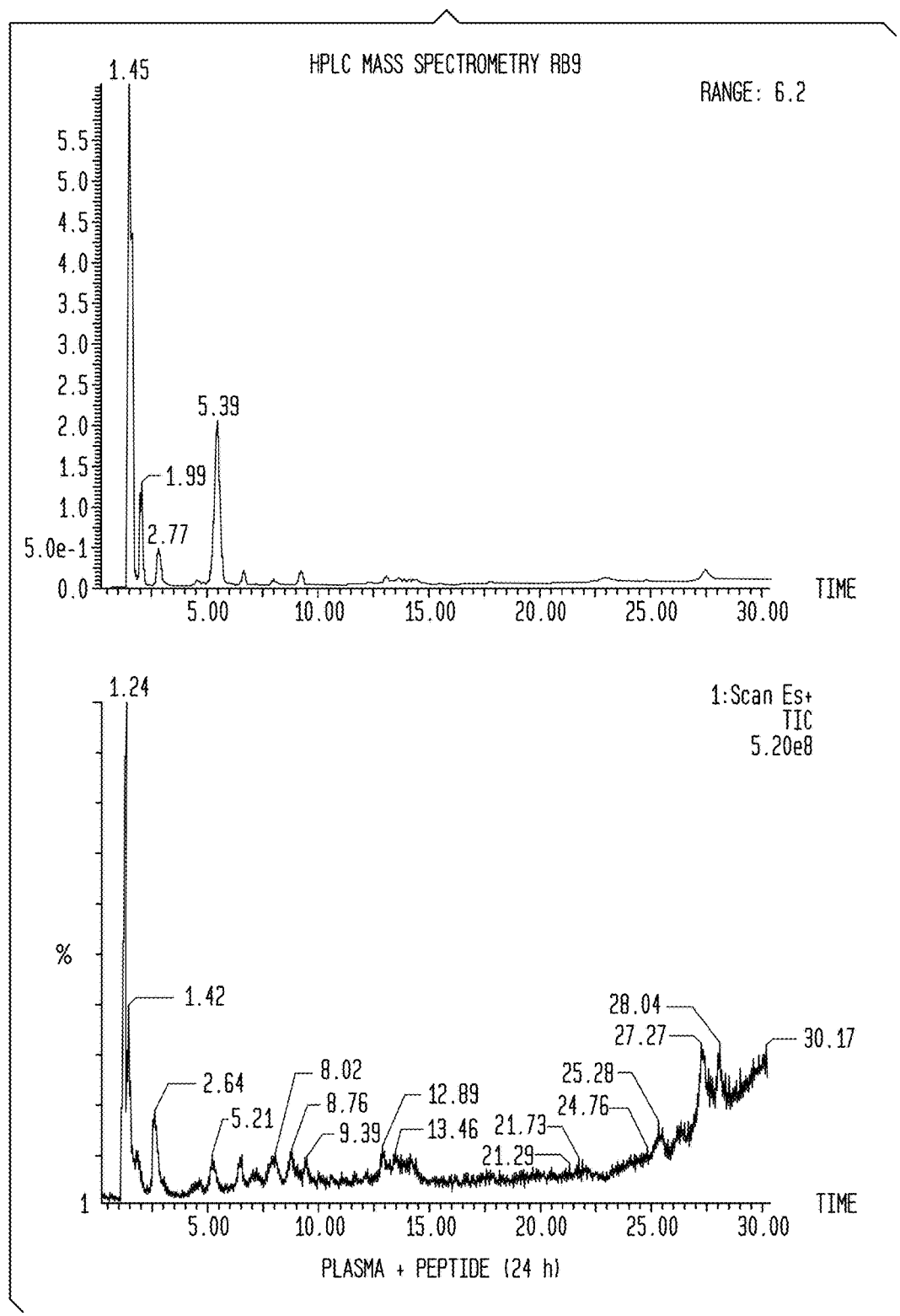

To analyze the peptide in HPLC and Mass Spectrum, an aliquot of 200 µL was transferred to a new Eppendorf tube and proteins were precipitated with 20 µL trifluoroacetic acid for 5 minutes at 4° C. After centrifugation for 10 minutes at 14,000 rpm, the supernatant was analyzed in an LC/ESI-MS (Waters). FIGS. 11A-11C show the HPLC and Mass spectrum peptide peak (0 hour) and its total degradation after 24 hours.

Figure 12:
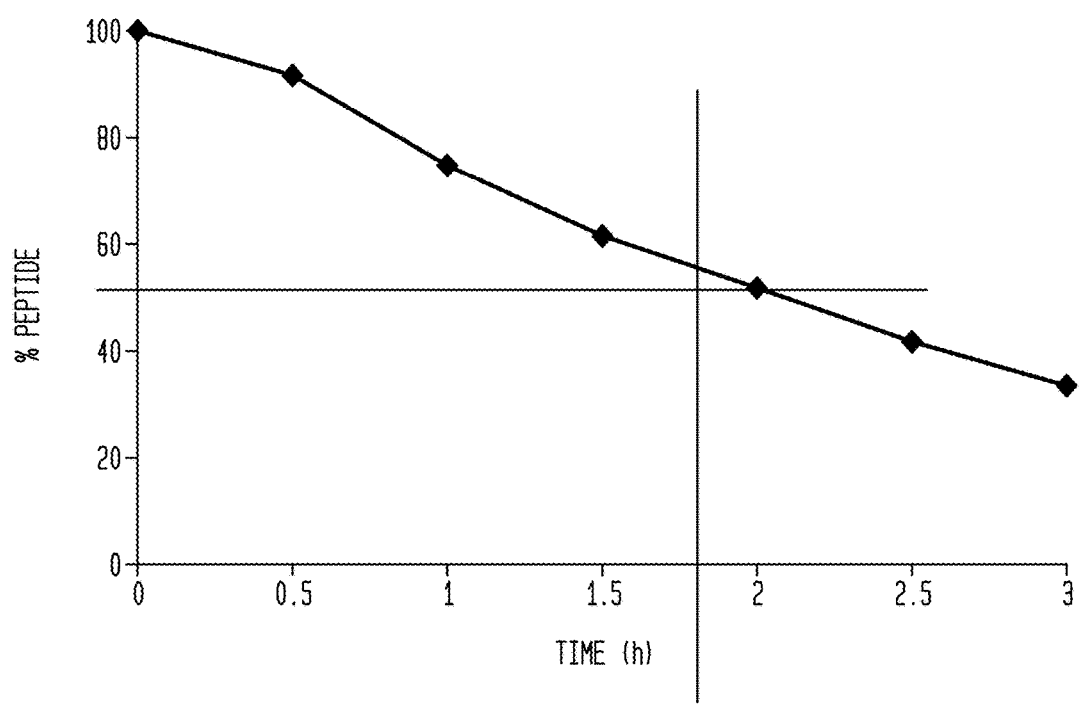
FIG. 12 is a graphical representation of 50% degradation of peptide RB9 in human plasma after 2 hours.

Regarding assays for determining time-lapse plasma degradation of RB9 peptide, peptide degradation by human plasma was monitored in HPLC and Mass spectra every 30 minutes as described above (FIG. 12). About 50% RB9 was cleaved after 2 hours of incubation at 37° C.

For comparison, RB8 was equally incubated in plasma. The half life thereof was less than 1 hour. The same method can be used to monitor peptide resistance to plasma proteolysis after derivatization procedures. The half life of RB9 is comparable with the half lives of other CDR-derived peptides studied before (Polonelli et al., PLoS One. 3(6): e2371, 2008), which, nevertheless, allowed sufficient exposure in the tumor cells to have in vivo protective effects in the mouse metastatic model.

Example 14

Tumor Cell Migration—Wound Healing Assay

Viable B16F10-Nex2 cells (5×105)/well were distributed on a 6-well culture plate and incubated overnight at 37° C. in a humidified chamber with 5% CO2. A P1000 tip was used for wounding the cell monolayer and the image was immediately captured (0 hour) using a camera (Jenoptik) with the software Progres 2.8. After 24 hours a new image of the same field was obtained and recorded (24 hours).

Figure 13A:
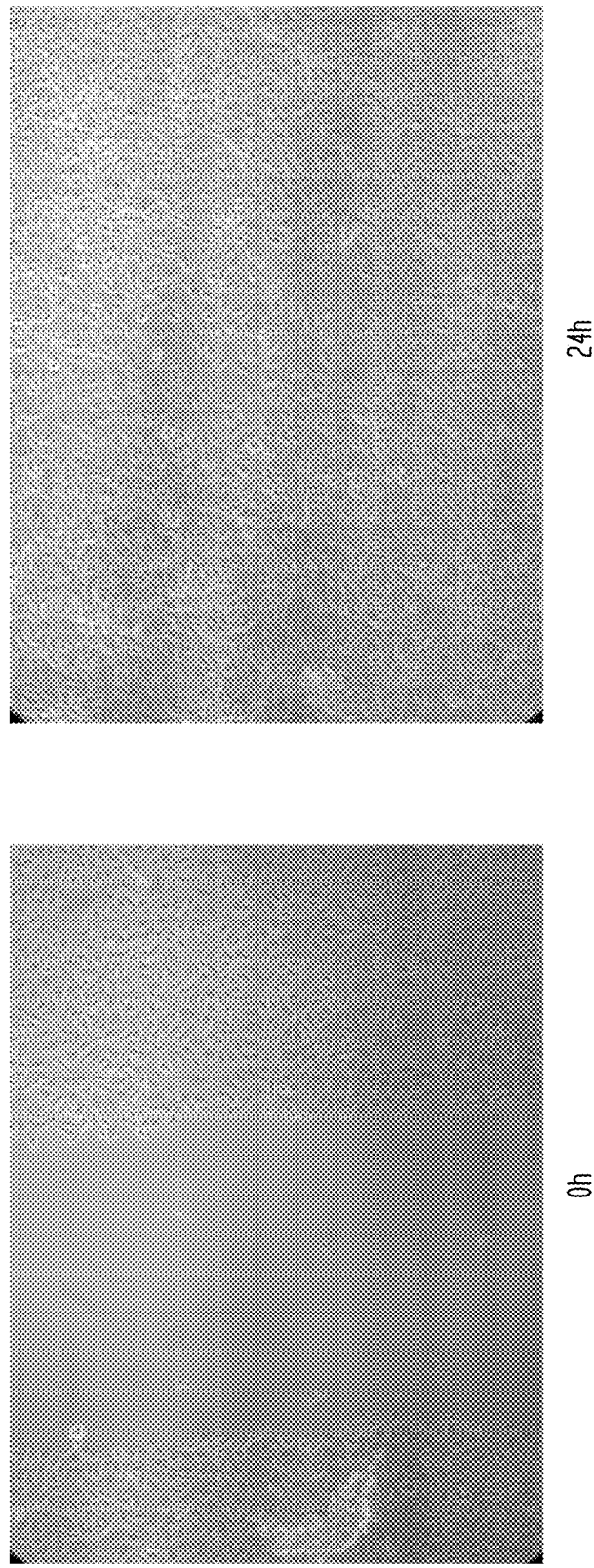
FIG. 13A is a photographical representation of the migration of B16F10-Nex2 melanoma cells in control, at 0 hour (left) and 24 hours (right).

Untreated control B16F10-Nex2 cells migrated to reconstitute the monolayer after 24 hours (FIG. 13A). Upon treatment with peptide RB10 (SEQ ID NO: 9) at a concentration of 500 µM, there occurred 100% inhibition of migration of 1×106 tumor cells (FIG. 13B).

Figure 16A:
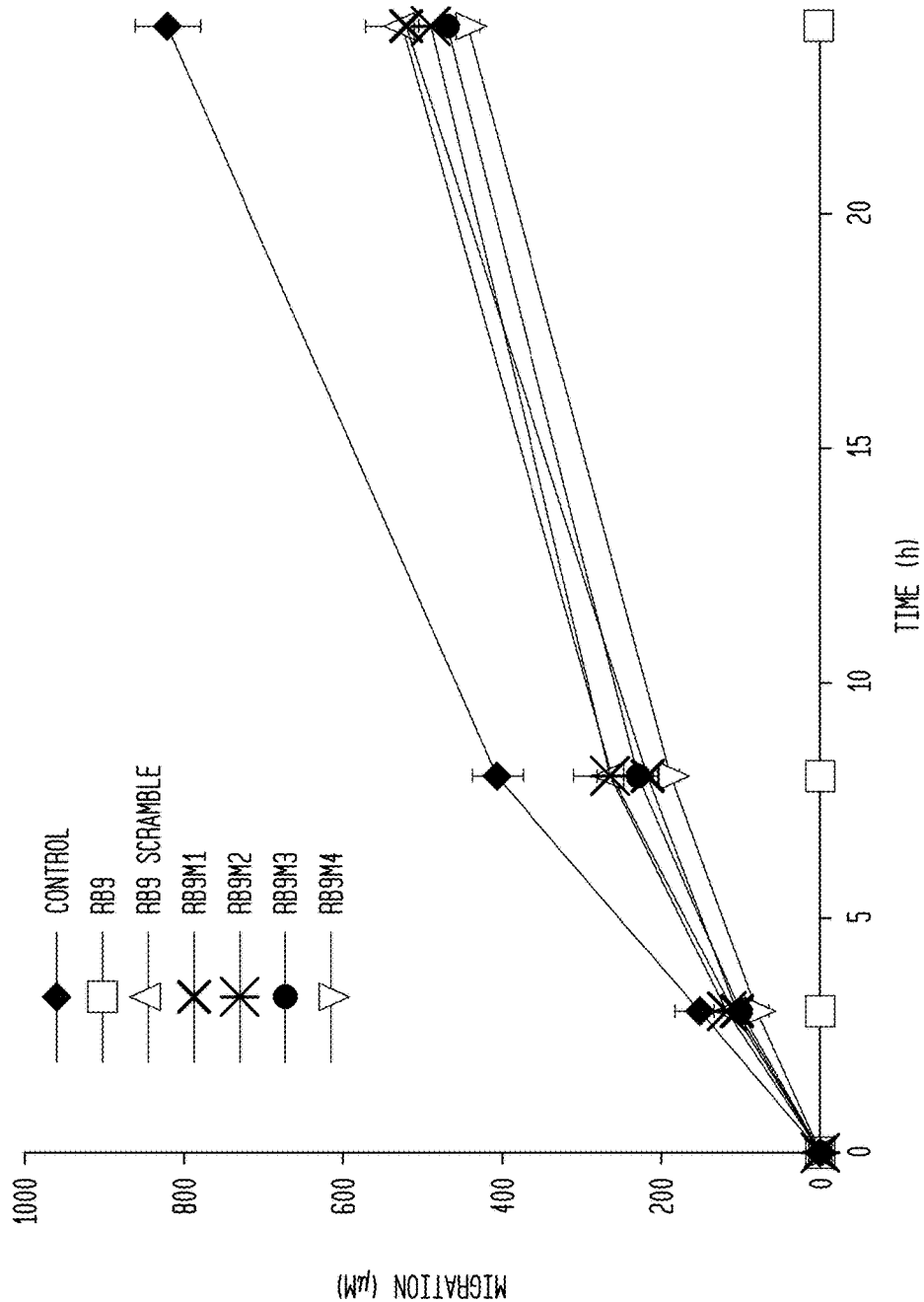
FIG. 16A is a graphical representation of the complete inhibition of B16F10-Nex2 cell migration by RB9 and partial inhibition by RB9 Scramble, RB9M1, RB9 M2, RB9 M3 and RB9 M4.
Figure 16B:
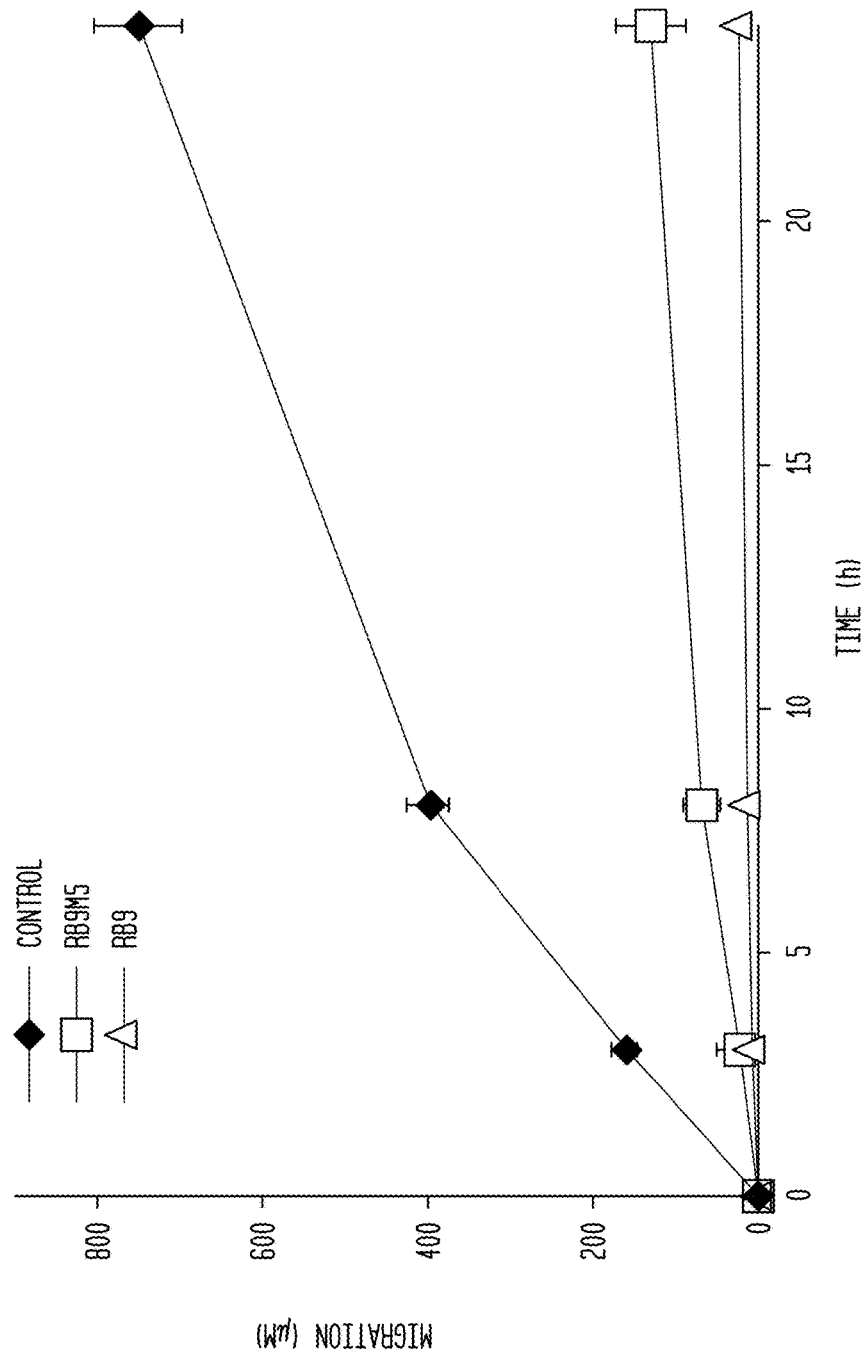
FIG. 16B is a graphical representation of the complete inhibition of B16F10-Nex2 cell migration by RB9 and partial inhibition by RB9 M5.
Figure 16E:
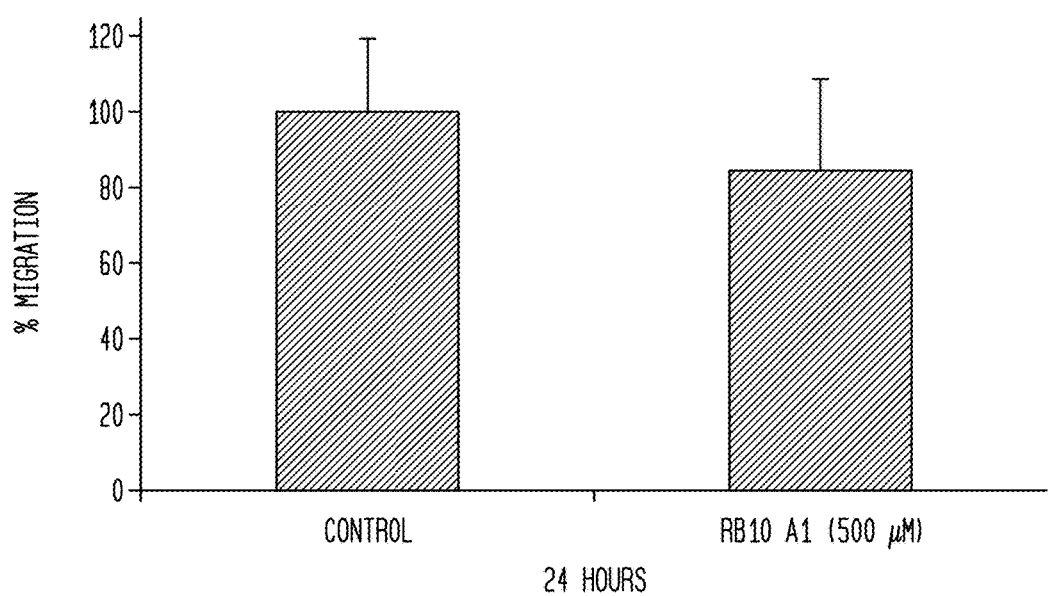
FIG. 16E is a graphical representation of the non-inhibition of B16F10-Nex2 cell migration by RB10 A1.
Figure 17A:
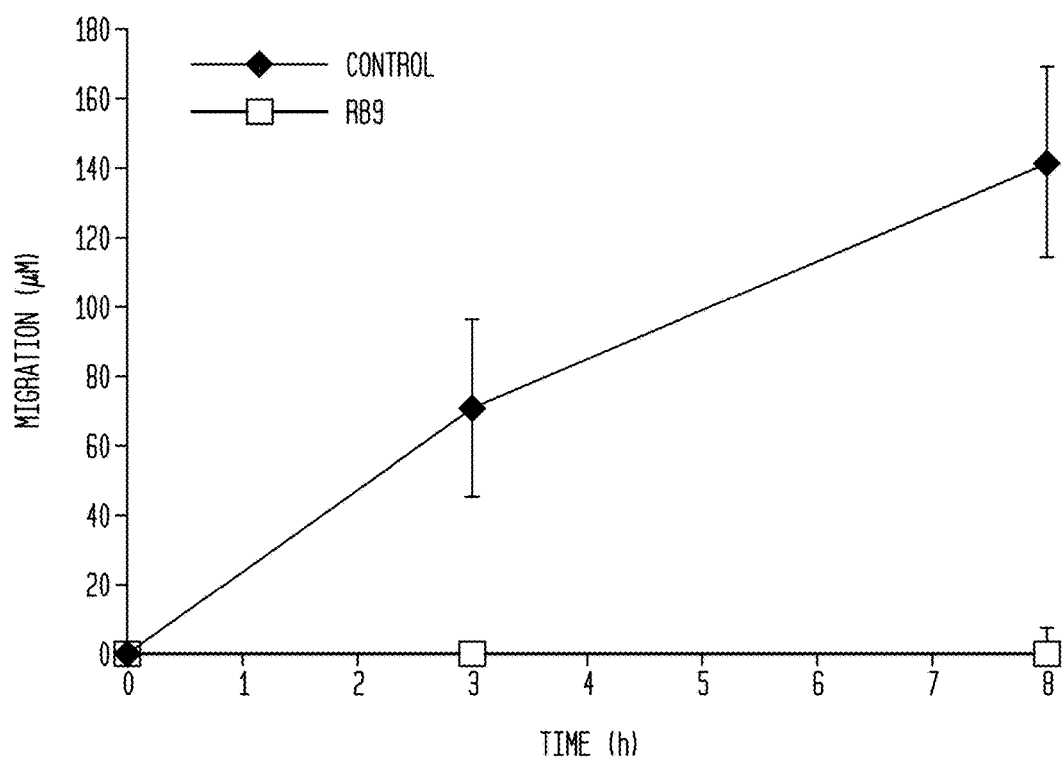
FIG. 17A is a graphical representation of the complete inhibition of the human melanoma A2058 cell migration by RB9.
Figure 17B:
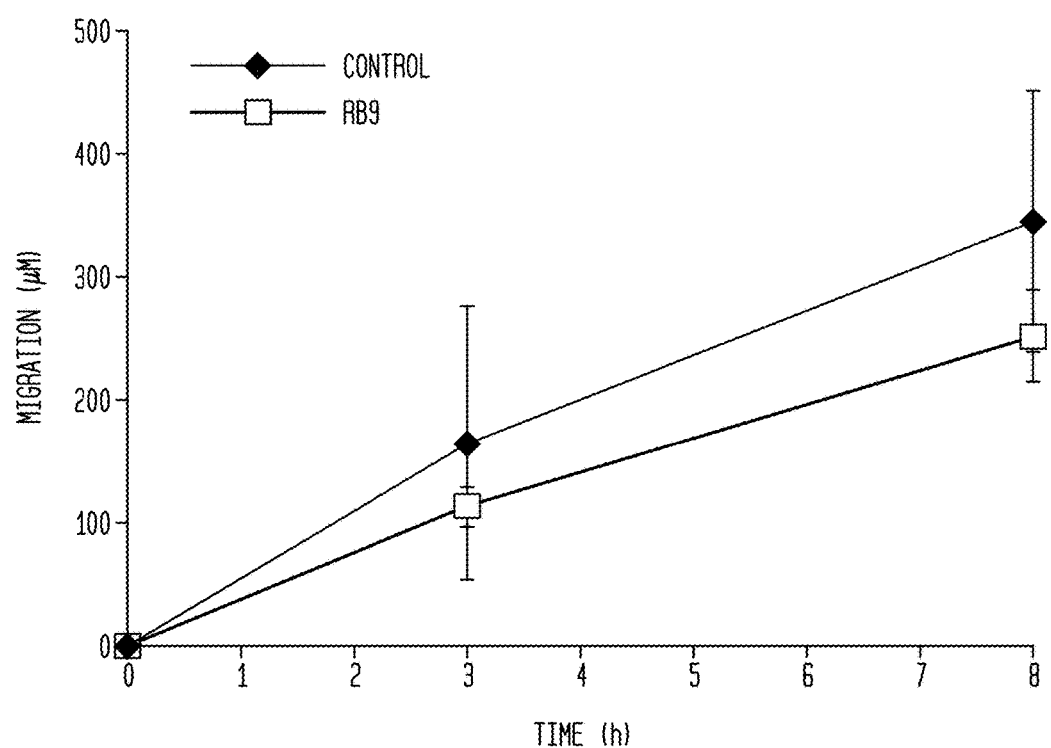
FIG. 17B is a graphical representation of the partial inhibition of the human glioblastoma U87 cell migration by RB9.
Figure 17C:
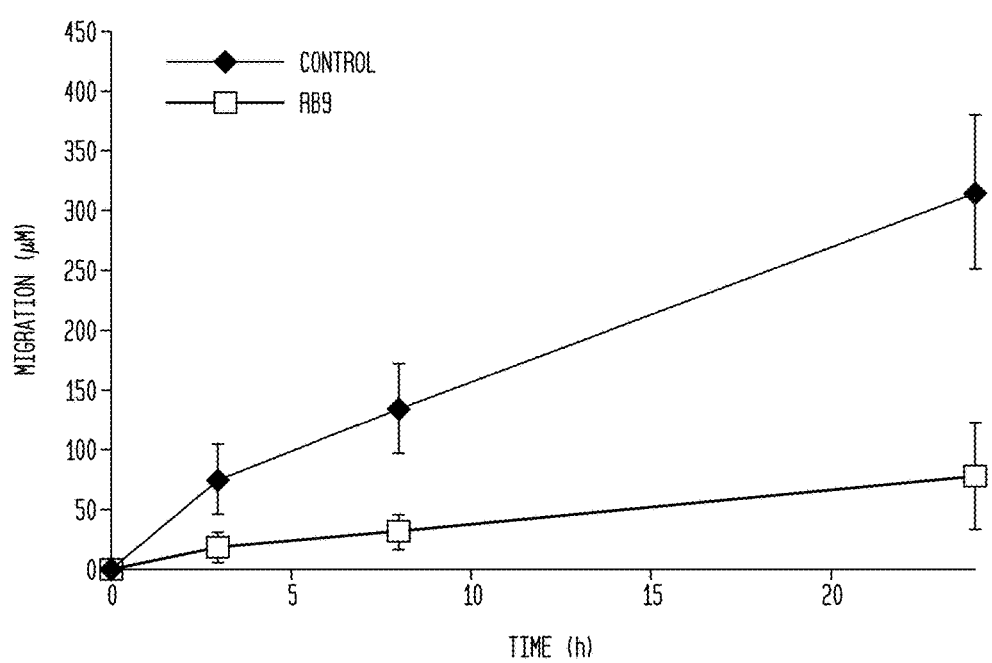
FIG. 17C is a graphical representation of the partial inhibition of the human colon cancer HCT cell migration by RB9.
Figure 17D:
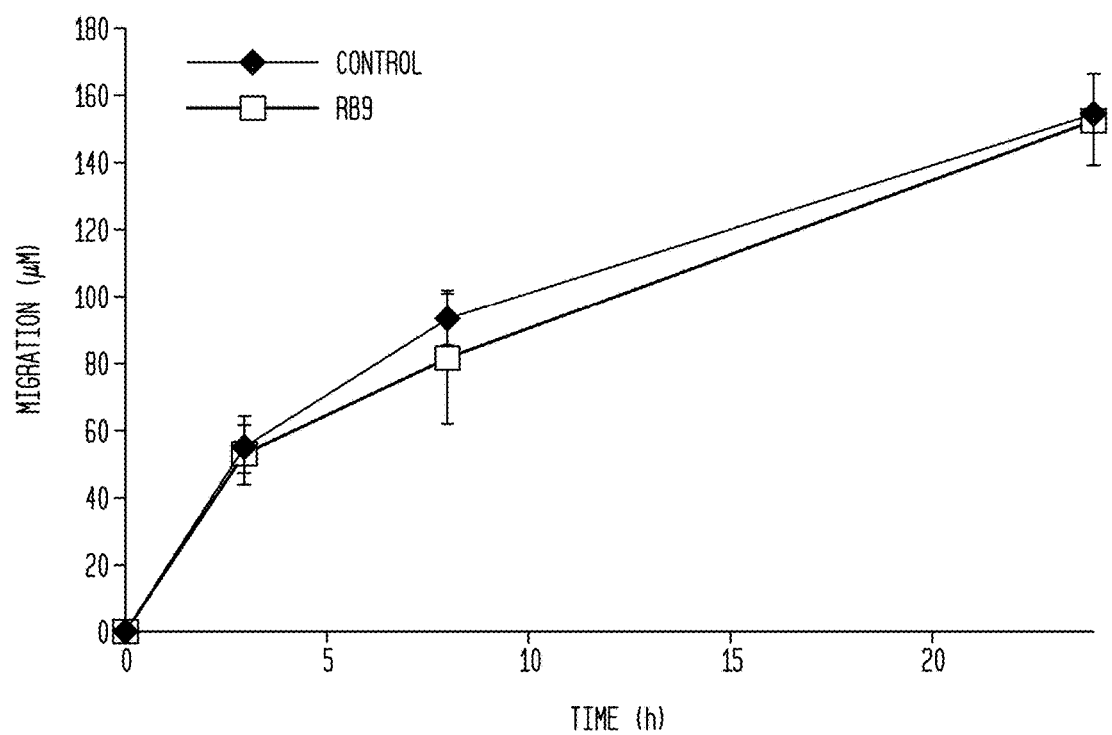
FIG. 17D is a graphical representation of the non-inhibition of the human cervix cancer SiHa cell migration by RB9.
Figure 17E:
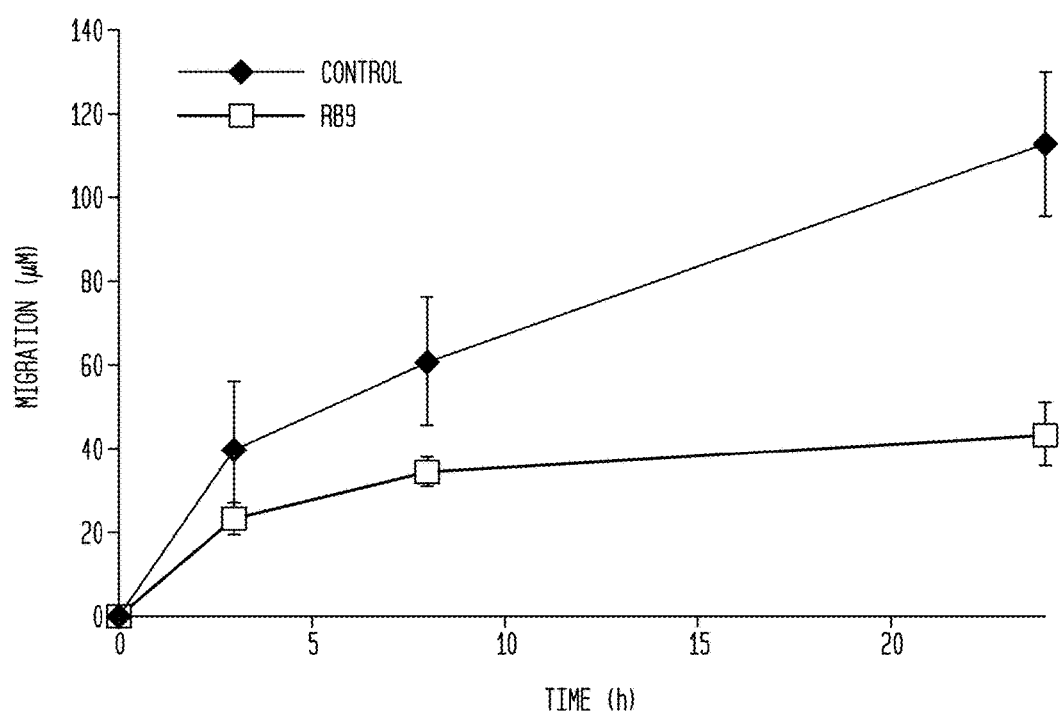
FIG. 17E is a graphical representation of the partial inhibition of the human ovary cancer OVCAR-3 cell migration by RB9.
Figure 17F:
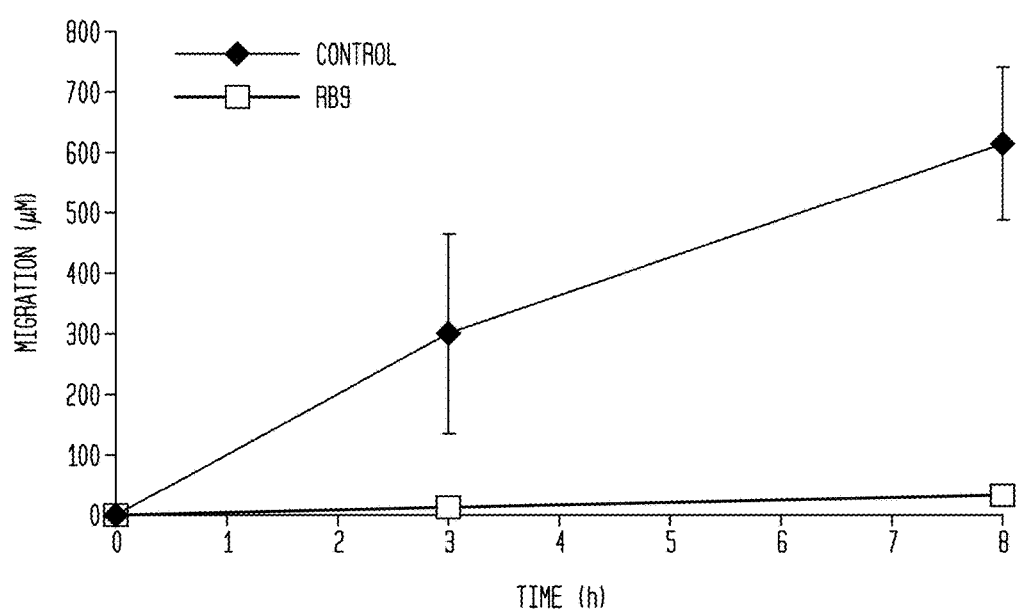
FIG. 17F is a graphical representation of the complete inhibition of the human breast cancer SKBr-3 cell migration by RB9.
Figure 18A:
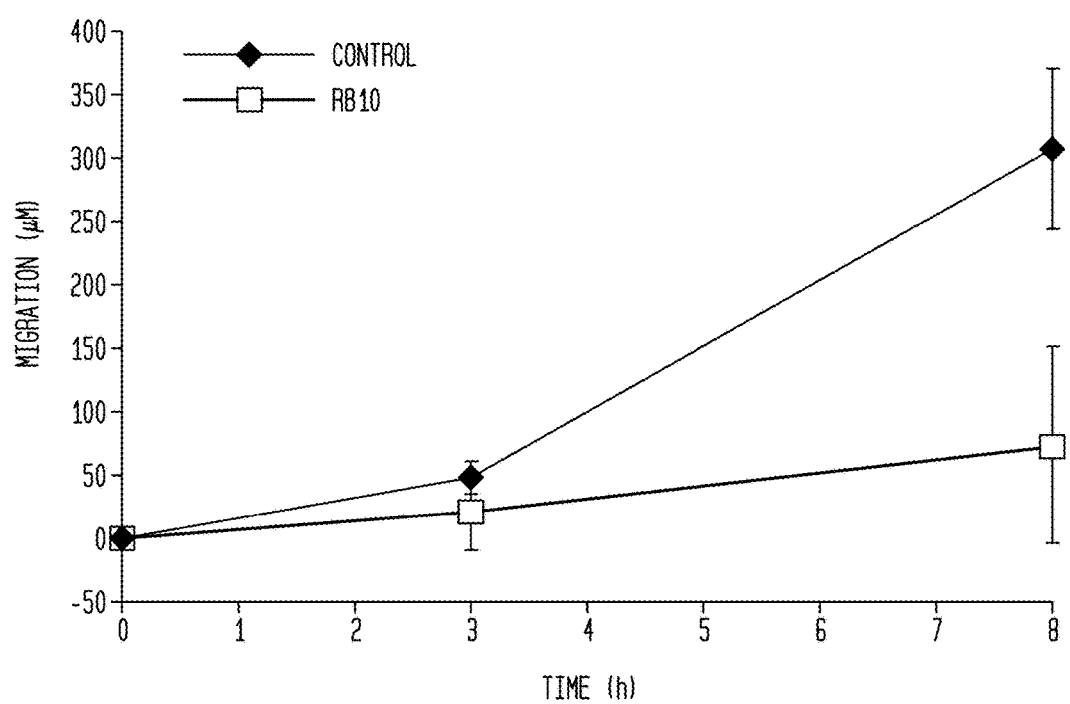
FIG. 18A is a graphical representation of the partial inhibition of the human glioblastoma U87 cell migration by RB10.
Figure 18B:
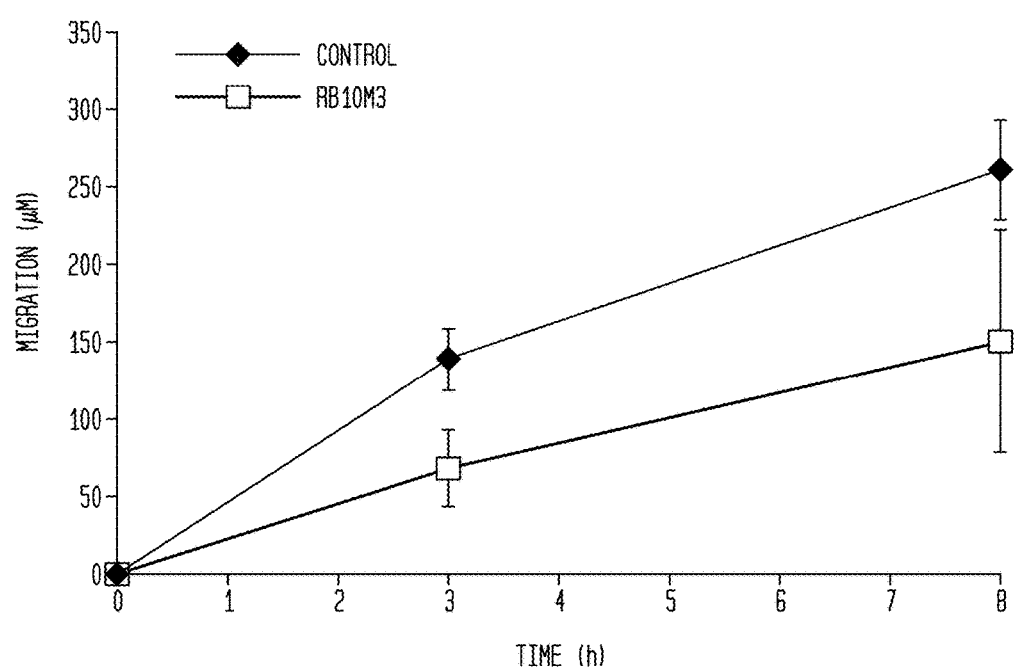
FIG. 18B is a graphical representation of the partial inhibition of the human glioblastoma U87 cell migration by RB10 M3.
Figure 18C:
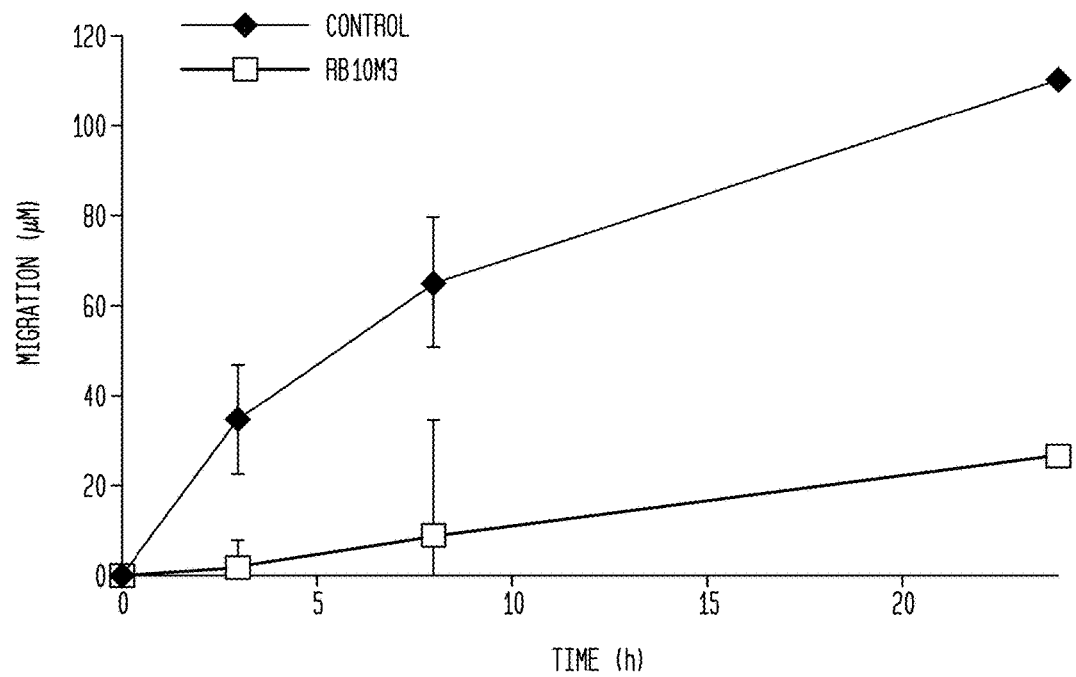
FIG. 18C is a graphical representation of the almost complete inhibition of the human cervix cancer SiHa cell migration by RB10 M3.
Figure 18D:
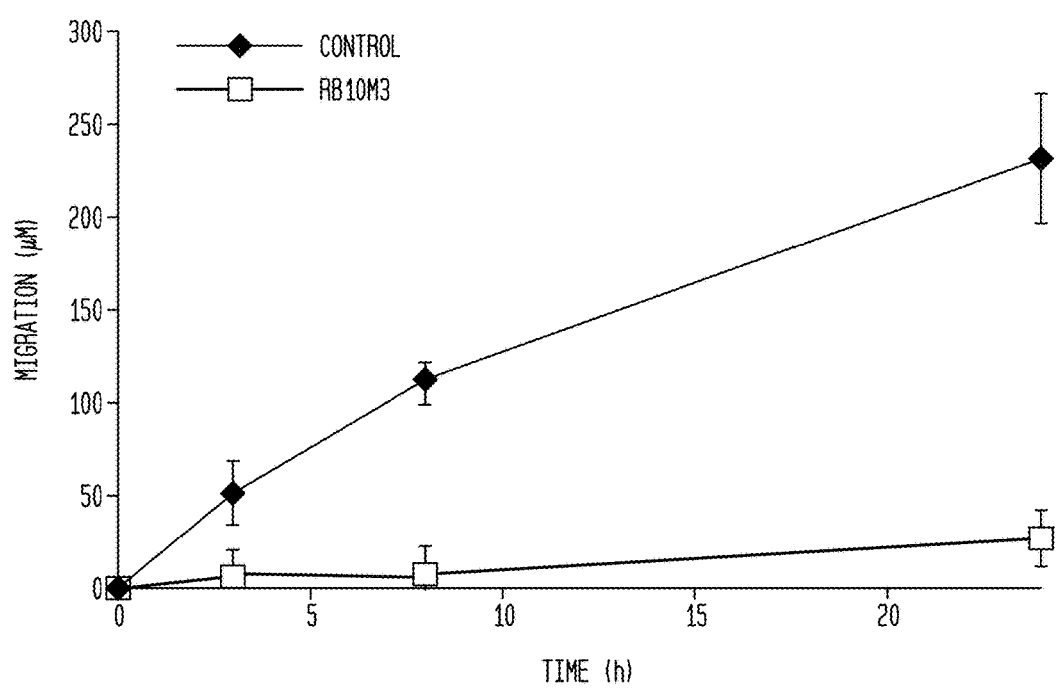
FIG. 18D is a graphical representation of the almost complete inhibition of the human cervix cancer HeLa cell migration by RB10 M3.

Total inhibition of migration of B16F10-Nex2 melanoma cells was observed with RB9 (SEQ ID NO: 8) and RB10 at 500 M, or with RB10M3 (dAla2Ala substitution, SEQ ID NO: 16). Other substitutions as in the alanine-scanning series and other derivatizations and scramble peptides showed partial migration inhibition or no effect (FIG. 16). This response points to a marked specificity of the H3 peptides for migration inhibition of B16F10-Nex2 cells.

Peptide RB9 completely inhibited migration of A2058 human melanoma, HCT colon carcinoma and SKBr3 breast cancer cells. It half inhibited Ovcar-3 cell migration and poorly so U87 glioblastoma tumor cells. It showed no effect on SiHa cervix cancer cells (FIG. 17).

Peptide RB10 or RB10M3 (SEQ ID NO: 31) showed partial migration inhibition of U87 glioblastoma cells and complete or almost complete inhibition of HeLa and SiHa cervix cancer cells (FIG. 18).

Figure 19A:
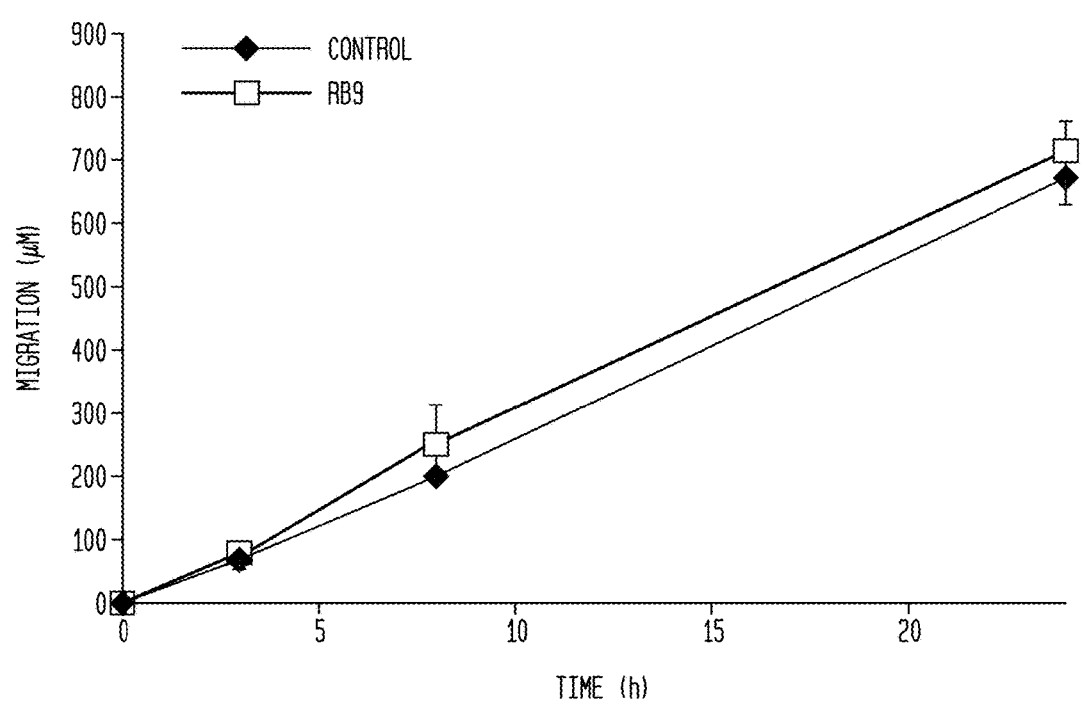
FIG. 19A is a graphical representation of the non-inhibition of 3T3 murine fibroblasts' migration by RB9.
Figure 19B:
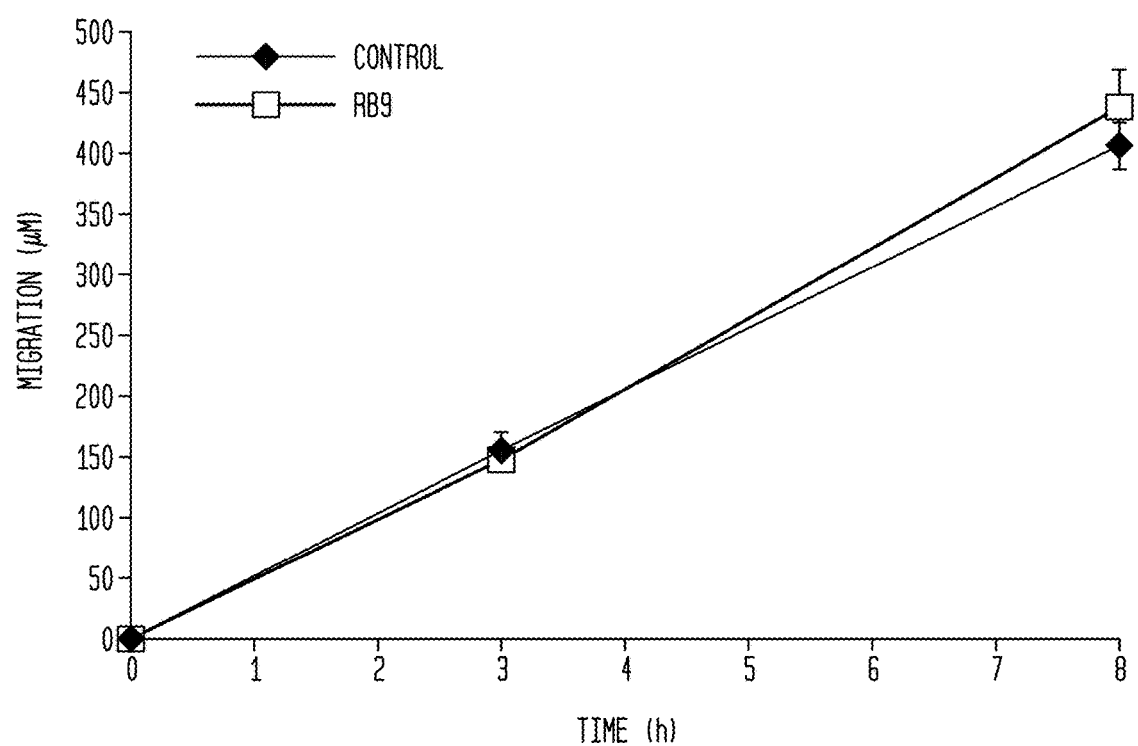
FIG. 19B is a graphical representation of the non-inhibition of FibroRP primary human fibroblasts' migration by RB9.
Figure 19C:
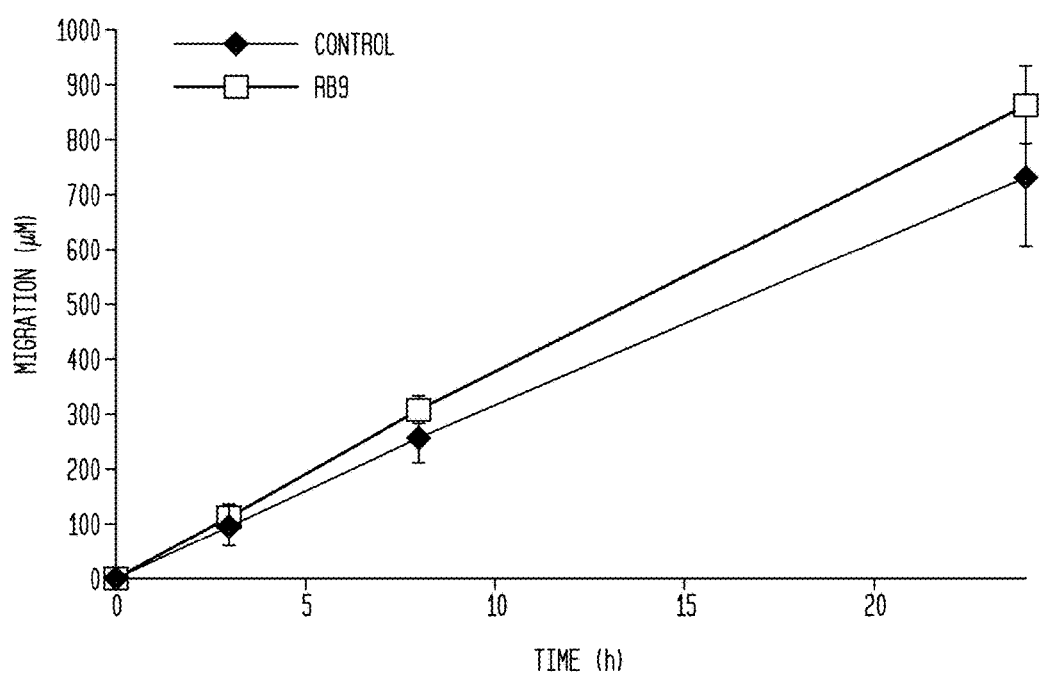
FIG. 19C is a graphical representation of the non-inhibition of T75 primary human fibroblasts' migration by RB9.

Peptide RB9 did not affect the migration of normal non-tumorigenic cells, a murine fibroblast cell line (3T3) and two primary human fibroblasts (FIG. 19).

Example 15

Dose-Dependent Inhibition of Tumor Cell Migration by Peptide RB10

Figure 14:
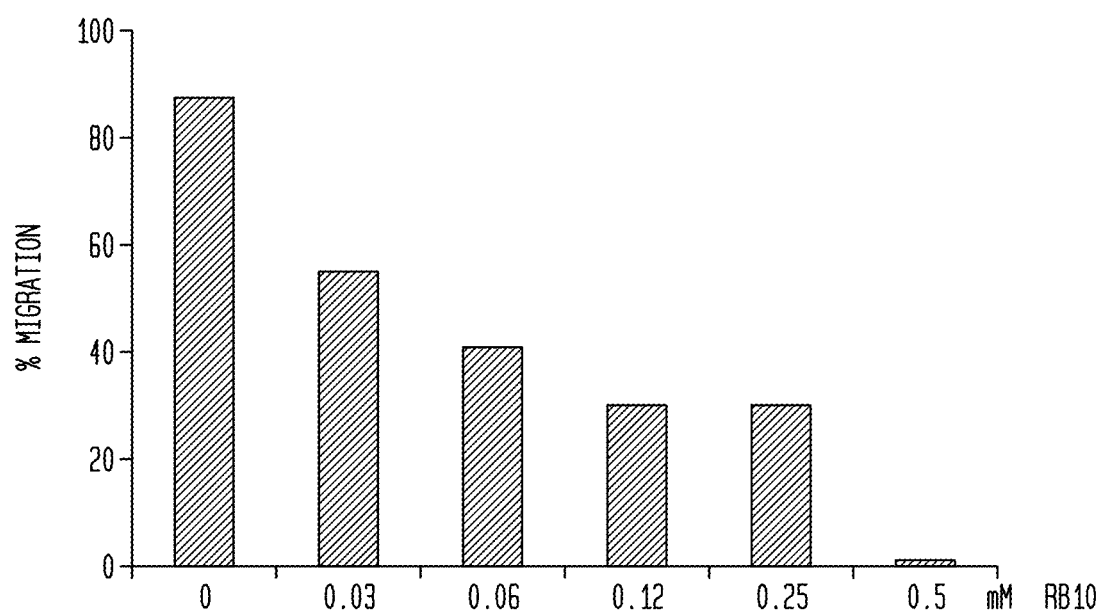
FIG. 14 is a graphical representation of RB10 dose-dependent inhibition of migration in murine B16F10-Nex2 melanoma cells.

Viable B16F10-Nex2 cells (3×10$^5$)/well were distributed in a 12-well culture plate and incubated for 4 hours at 37° C. in a humidified chamber with 5% $CO_2$. Fresh medium containing RB10 (SEQ ID NO: 9) at different concentrations was added to the wells and incubated again for 4 hours. The monolayer wounding was performed as described above in Example 12, and images obtained accordingly. After 24 hours a new image in the same field was obtained and recorded (24 hours). As shown in FIG. 14, the migration inhibition was dose-dependent and even at low concentration (30 µM) RB10 was able to inhibit migration in more than 30%. At 500 µM it inhibited 100% of cell migration as shown in FIG. 14. Magnification ×100.

Example 16

RB10 Growth Inhibition

Figure 15:
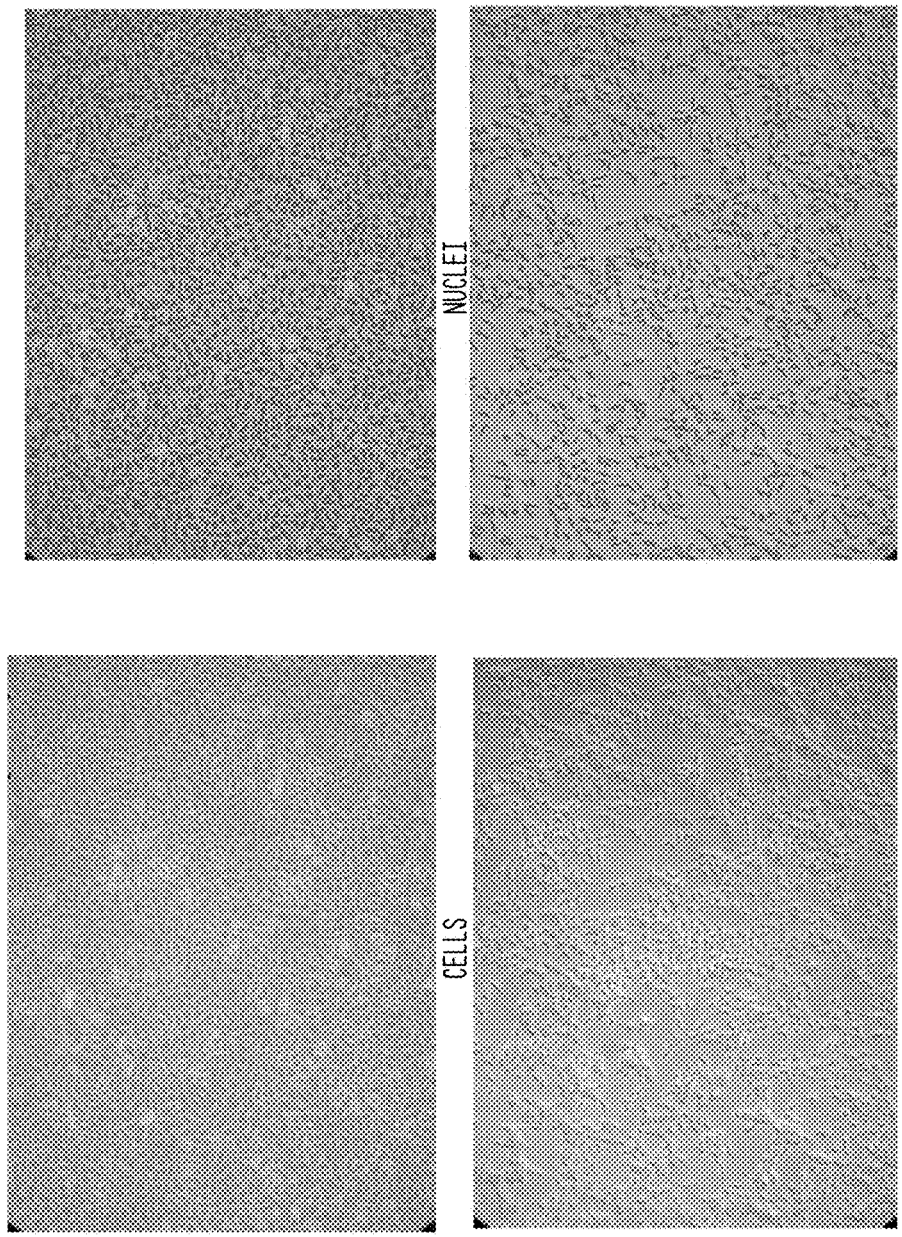
FIG. 15 is a photographical representation of RB10 partial inhibition of growth of murine B16F10-Nex2 melanoma cells, after 12 hours incubation.

Viable B16F10-Nex2 cells (5×10$^5$)/well were distributed on a 6-well culture plate and incubated for 4 hours. Fresh medium containing 0 or 500 µM of RB10 (SEQ ID NO: 10) was added to the wells and incubated for 12 hours. Image was captured using a camera (Jenoptik) with the software Progres 2.8. The number of cells was detected using the software pixcavator (intelligent perception). After 12 hours with 0.5 mM of RB10, melanoma cells had fewer cells by 39% (FIG. 15); these cells were still able to proliferate but not to migrate. These effects of RB10 seem to explain why the peptide is protective against a metastatic model of melanoma but not against the development of a primary tumor in a subcutaneous model, both in susceptible mice. Magnification ×100.

Example 17

In Vivo Peptide Toxicity Evaluation

Figure 21:
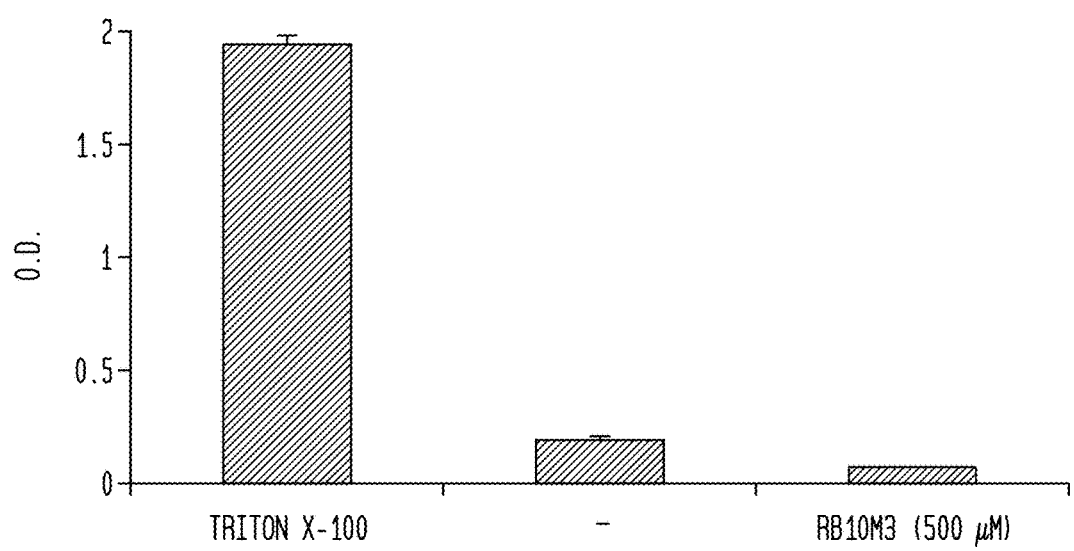
FIG. 21 is a graphical representation of the non-hemolytic effect of RB10 M3.

Mice were injected with RB9 (SEQ ID NO: 8) for seven consecutive days (300 µg via i.p.) and were sacrificed thereafter for histopathology. No signs of toxicity or morphological alterations were observed in the liver, lung, heart, kidney and spleen. Also the peptides were not hemolytic as shown in FIG. 21 for RB10M3 (SEQ ID NO: 31).

It will be appreciated by those skilled in the art to which the present subject matter pertains that various modifications can be made without departing from the essential nature thereof. It is intended to encompass all such modification within the scope of the appended claims.

The invention claimed is:

1. A method of treating a tumor or cancer or of inhibiting tumor or cancer growth comprising administering to a subject in need thereof an effective amount of a pharmaceutical composition, wherein the composition comprises an antitumor peptide selected from the group consisting of SEQ ID NOS: 3, 8, 9, 14, 15, 16, 17, 18, 19, 20, 21, 22, 23, 24, 25, 26, 27, 28, 29, 30, 31, 32, and 33, and a pharmaceutically acceptable carrier or diluent.

2. The method of claim 1, wherein the peptide of SEQ ID NO:8 is cyclic.

3. The method of claim 1, wherein the tumor is one selected from the group consisting of melanoma, colon carcinoma, lung carcinoma, renal carcinoma, breast carcinoma, head and neck cancer, gastric and intestinal cancer, prostate cancer, liver cancer and glioblastoma.

4. A method of manufacture of a pharmaceutical composition for treating a tumor or cancer or for inhibiting tumor or cancer growth in a subject, comprising the steps of:

i) providing an antitumor peptide selected from the group consisting of SEQ ID NOS: 3, 8, 9, 14, 15, 16, 17, 18, 19, 20, 21, 22, 23, 24, 25, 26, 27, 28, 29, 30, 31, 32, and 33;

ii) mixing said antitumor peptide with an excipient, diluent or carrier or mixture thereof, iii) subjecting the resulting mixture to sterilization; and iv) formulating the composition as a tablet, capsule, solution, suspension, powder, inhalant, lotion, tincture, troche, suppository, or transdermal patch.

5. The method of claim 4, wherein the cancer is one selected from the group consisting of melanoma, colon cancer, lung cancer, renal cancer, breast cancer, brain cancer, head and neck cancer, gastric and intestinal cancer, prostate cancer, liver cancer and glioblastoma.

* * * * *